US011332443B2

(12) United States Patent
Cutler et al.

(10) Patent No.: US 11,332,443 B2
(45) Date of Patent: *May 17, 2022

(54) DERIVATIVES OF HALO QUINABACTIN

(71) Applicants: THE REGENTS OF THE UNIVERSITY OF CALIFORNIA, Oakland, CA (US); SYNGENTA PARTICIPATIONS AG, Basel (CH)

(72) Inventors: Sean R. Cutler, Riverside, CA (US); Sebastian V. Wendeborn, Basel (CH); Olivier Loiseleur, Basel (CH); Mathilde D. Lachia, Basel (CH); Davide Sabbadin, Basel (CH)

(73) Assignees: THE REGENTS OF THE UNIVERSITY OF CALIFORNIA, Oakland, CA (US); SYNGENTA PARTICIPATIONS AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/755,408

(22) PCT Filed: Aug. 19, 2016

(86) PCT No.: PCT/US2016/047780
§ 371 (c)(1),
(2) Date: Feb. 26, 2018

(87) PCT Pub. No.: WO2017/034982
PCT Pub. Date: Mar. 2, 2017

(65) Prior Publication Data
US 2018/0312470 A1 Nov. 1, 2018

Related U.S. Application Data

(60) Provisional application No. 62/291,726, filed on Feb. 5, 2016, provisional application No. 62/210,858, filed on Aug. 27, 2015.

(51) Int. Cl.
*C07D 215/38* (2006.01)
*A01N 43/42* (2006.01)
*C07D 401/12* (2006.01)
*C07D 409/12* (2006.01)
*C07D 405/12* (2006.01)
*C07D 417/12* (2006.01)

(52) U.S. Cl.
CPC .......... *C07D 215/38* (2013.01); *A01N 43/42* (2013.01); *C07D 401/12* (2013.01); *C07D 405/12* (2013.01); *C07D 409/12* (2013.01); *C07D 417/12* (2013.01)

(58) Field of Classification Search
CPC .. C07D 215/38; C07D 401/12; C07D 405/12; C07D 409/12; C07D 417/12; A01N 43/42
See application file for complete search history.

(56) References Cited

U.S. PATENT DOCUMENTS

| 9,173,395 | B2 | 11/2015 | Frackenpohl et al. |
| 10,065,926 | B2 | 9/2018 | Frackenpohl et al. |
| 2017/0027172 | A1* | 2/2017 | Frackenpohl .......... A01N 43/78 |
| 2018/0020662 | A1 | 1/2018 | Frackenpohl et al. |
| 2018/0199575 | A1 | 7/2018 | Helmke et al. |

FOREIGN PATENT DOCUMENTS

| WO | WO 2013/004652 | 1/2013 |
| WO | WO 2013/148339 | 10/2013 |
| WO | WO-2013148339 A1 * | 10/2013 ............. A01N 43/42 |
| WO | WO 2014/210555 | 12/2014 |
| WO | WO 2015/155154 | 10/2015 |
| WO | WO 2016/022910 | 2/2016 |
| WO | WO 2016/128365 | 8/2016 |
| WO | WO/2017/034982 | 3/2017 |

OTHER PUBLICATIONS

D. A. Williams et al., "2. Drug Design and Relationship of Functional Groups to Pharmacologic Activity," Foye's Principles of Medicinal Chemistry, 5th Edition, Copyright 2002, p. 37-67.*
Soult, Allison, "5.1: Isomers," University of Kentucky, <https://chem.libretexts.org/@go/page/58809>, updated Aug. 13, 2020, pp. 1-4.*
Berge et al., *Journal of Pharmaceutical Science*, 66: 1-19 (1977).
Maehr, *J. Chem. Ed.*, 62: 114-120 (1985).
Okamoto et al. (PNAS, 2013, 110(29), 12132-12137.
Park et al. (2009, Science, vol. 324(5930), 1068-1071).
International Search Report (PCT/US2016/047780) (dated Sep. 29, 2016).
Russian Search Report (RU 2018110612 // PCT/US2016/047780) (dated Nov. 7, 2019).

* cited by examiner

*Primary Examiner* — Monica A Shin
(74) *Attorney, Agent, or Firm* — Morgan, Lewis & Bockius LLP

(57) ABSTRACT

The present invention relates to novel sulfonamide derivatives of formula (I), to processes and intermediates for preparing them, to plant growth regulator compositions comprising them and to methods of using them for controlling the growth of plants, improving plant tolerance to abiotic stress (including environmental and chemical stresses), inhibiting seed germination and/or safening a plant against phytotoxic effects of chemicals.

1 Claim, 41 Drawing Sheets

FIG. 1

Soybean: % change in water use relative to control (blank formulation)

| Compounds | 0 DAA AM | 0DAA PM | 1DAA AM | 1DAA PM | 2 DAA AM | 2 DAA PM | Total 0 to 2 DAA |
|---|---|---|---|---|---|---|---|
| control | 0 | 0 | 0 | 0 | 0 | 0 | 0 |
| quinabactin | -45.1 | -42.-2 | -20.2 | -10.8 | -3 | -2.2 | -17 |
| HQ29 | -43 | -47 | -51 | -45 | -44 | -37 | -45 |
| HQ28 | -40 | -42 | -41 | -34 | -26 | -18 | -33 |
| HQ2 | -50 | -48 | -46 | -38 | -31 | -24 | -38 |
| HQ1 | -51 | -54 | -55 | -49 | -44 | -38 | -48 |
| HQ30 | -48.8 | -53.7 | -48 | -54.6 | -54.8 | -49.4 | -53.4 |
| HQ47 | -17 | -12.8 | -6.1 | -2.8 | -1.1 | 1 | -4.9 |

FIG. 2

Soybean: % change in water use relative to control (blank formulation)

| Compounds | Rate | %WU | | | | | |
|---|---|---|---|---|---|---|---|
| | | 0 DAA AM* | 0 DAA PM | 1 DAA AM | 1 DAA PM | 2 DAA AM | 2 DAA PM | Total 0 to 2 DAA |
| Quinabactin | 31.25uM | -0.3 | -0.3 | 0.2 | -0.1 | -0.9 | -1.3 | -0.7 |
| HQ1 | | -6.3 | -4.7 | -2.3 | -0.8 | -3.2 | -0.7 | -2.8 |
| Quinabactin | 125uM | -15.3 | -5.7 | 1.8 | 2.9 | 2.4 | 1.1 | -0.5 |
| HQ1 | | -38.5 | -33.1 | -10.4 | -6.2 | -3.1 | -2.4 | -12.8 |
| Quinabactin | 500uM | -42.0 | -41.2 | -18.6 | -10.8 | -3.8 | -2.9 | -16.9 |
| HQ1 | | -47.2 | -51.4 | -48.8 | -42.3 | -33.4 | -27.2 | -40.4 |

FIG. 3

Corn: % change in water use relative to control (blank formulation)

| Compounds | 0 DAA AM | 0DAA PM | 1DAA AM | 1DAA PM | 2 DAA AM | 2 DAA PM | Total 0 to 2 DAA |
|---|---|---|---|---|---|---|---|
| control | 0 | 0 | 0 | 0 | 0 | 0 | 0 |
| quinabactin | -21.3 | -23.5 | -17.4 | -15.3 | -11.5 | -11 | -15.9 |
| HQ1 | -30.5 | -34 | -17 | -13.9 | -8.9 | -8.5 | -17 |
| HQ28 | -20.6 | -14.6 | -12.3 | -4.9 | -4.1 | -1.8 | -8.5 |
| HQ29 | -25.3 | -19.1 | -14 | -6.1 | -4.6 | .3.5 | -10.7 |
| HQ30 | -45.1 | -52.8 | -22.3 | -11.3 | -5.3 | -3.4 | -20.8 |
| HQ46 | -3 | -0.5 | 0.4 | 0.7 | 3.3 | 3.5 | 1.4 |
| HQ47 | -13.8 | -7.1 | -6.7 | -2.1 | -4.1 | -1.6 | -4.8 |
| HQ49 | -2.1 | -2.5 | -4.3 | -1.6 | -1.6 | 0.2 | -1.8 |

FIG. 4

Corn: % change in water use relative to control (blank formulation) for one day after application

| Compounds | 0 DAA AM | 0DAA PM |
|---|---|---|
| control | 0 | 0 |
| quinabactin | -14 | -11 |
| HQ33 | -19.7 | -14.1 |
| HQ34 | -7.7 | 2.7 |
| HQ35 | -29 | -24.4 |
| HQ39 | -7.3 | -0.1 |
| HQ48 | -32.8 | -24.7 |
| HQ51 | -4.7 | 1.3 |
| HQ52 | -26 | -20.9 |

| ID | R¹ | structure | ID | R¹ | structure |
|---|---|---|---|---|---|
| A01 | ethyl |  | A12 | ethyl |  |
| A02 | ethyl |  | A13 | ethyl |  |
| A03 | ethyl |  | A14 | ethyl |  |
| A04 | ethyl |  | A15 | ethyl |  |
| A05 | ethyl |  | A16 | ethyl |  |
| A06 | ethyl |  | A17 | ethyl |  |
| A07 | ethyl |  | A18 | ethyl |  |
| A08 | ethyl |  | A19 | ethyl |  |
| A09 | ethyl |  | A20 | ethyl |  |
| A10 | ethyl |  | A21 | ethyl |  |
| A11 | ethyl |  | | | |

| | | | | | |
|---|---|---|---|---|---|
|  | | | | | |
| ID | R¹ |  | ID | R¹ | |
| A22 | ethyl |  | A30 | ethyl |  |
| A23 | ethyl |  | A31 | ethyl |  |
| A24 | ethyl |  | A32 | ethyl |  |
| A25 | ethyl |  | A33 | ethyl |  |
| A26 | ethyl |  | A34 | ethyl |  |
| A27 | ethyl |  | A35 | ethyl |  |
| A28 | ethyl |  | A36 | ethyl |  |
| A29 | ethyl |  | A37 | ethyl |  |
| | | | A38 | ethyl | |

| | | | | | |
|---|---|---|---|---|---|
|  | | | | | |
| ID | R¹ |  | ID | R¹ | |
| A39 | ethyl |  | B02 | isopropyl |  |
| A40 | ethyl |  | B03 | isopropyl |  |
| A41 | ethyl |  | B04 | isopropyl |  |
| A42 | ethyl |  | B05 | isopropyl |  |
| A43 | ethyl |  | B06 | isopropyl |  |
| A44 | ethyl |  | B07 | isopropyl |  |
| A45 | ethyl |  | B08 | isopropyl |  |
| A46 | ethyl |  | B09 | isopropyl |  |
| A47 | ethyl |  | B10 | isopropyl |  |
| | | | B11 | isopropyl |  |
| B01 | isopropyl |  | B12 | isopropyl | |

Fig. 5D

| ID | R¹ | ₂-L-R⁷) |
|----|----|----|
| B13 | isopropyl | HF₂CO-C₆H₄-CH₂-S(O)₂-NH- |
| B14 | isopropyl | 4-F-C₆H₄-CH₂-S(O)₂-NH- |
| B15 | isopropyl | 4-vinyl-C₆H₄-CH₂-S(O)₂-NH- |
| B16 | isopropyl | 4-ethynyl-C₆H₄-CH₂-S(O)₂-NH- |
| B17 | isopropyl | 4-isopropenyl-C₆H₄-CH₂-S(O)₂-NH- |
| B18 | isopropyl | 4-propenyl-C₆H₄-CH₂-S(O)₂-NH- |
| B19 | isopropyl | 4-(MeON=CH)-C₆H₄-CH₂-S(O)₂-NH- |
| B20 | isopropyl | benzothiazol-6-yl-CH₂-S(O)₂-NH- |
| B21 | isopropyl | 2,2-difluoro-benzo[1,3]dioxol-5-yl-CH₂-S(O)₂-NH- |
| B22 | isopropyl | 2,5-diF-C₆H₃-CH₂-S(O)₂-NH- |

| ID | R¹ | |
|----|----|----|
| B23 | isopropyl | 2,3-diF-C₆H₃-CH₂-S(O)₂-NH- |
| B24 | isopropyl | 3,4-diMe-C₆H₃-CH₂-S(O)₂-NH- |
| B25 | isopropyl | 3-F-4-Me-C₆H₃-CH₂-S(O)₂-NH- |
| B26 | isopropyl | 3-Cl-4-Me-C₆H₃-CH₂-S(O)₂-NH- |
| B27 | isopropyl | 3,4-diCl-C₆H₃-CH₂-S(O)₂-NH- |
| B28 | isopropyl | 3-F-4-Cl-C₆H₃-CH₂-S(O)₂-NH- |
| B29 | isopropyl | 2,4-diMe-C₆H₃-CH₂-S(O)₂-NH- |
| B30 | isopropyl | 2-F-4-Me-C₆H₃-CH₂-S(O)₂-NH- |

Fig. 5E

| | | | ID | R¹ | |
|---|---|---|---|---|---|
| ID | R¹ | ⁓N(H)-S(=O)₂-L-R⁷ | | | |
| B31 | isopropyl | 4-Br, 2-F-benzyl-CH₂-S(=O)₂-NH⁓ | B41 | isopropyl | pyridin-3-yl-CH₂-S(=O)₂-NH⁓ |
| B32 | isopropyl | 4-CN, 2-F-benzyl-CH₂-S(=O)₂-NH⁓ | B42 | isopropyl | 5-Cl-thiophen-2-yl-CH₂-S(=O)₂-NH⁓ |
| B33 | isopropyl | 2-Cl, 4-Me-benzyl-CH₂-S(=O)₂-NH⁓ | B43 | isopropyl | 5-Me-thiophen-2-yl-CH₂-S(=O)₂-NH⁓ |
| B34 | isopropyl | 5-Cl-pyridin-2-yl-CH₂-S(=O)₂-NH⁓ | B44 | isopropyl | thiophen-2-yl-CH₂-S(=O)₂-NH⁓ |
| B35 | isopropyl | 5-Me-pyridin-2-yl-CH₂-S(=O)₂-NH⁓ | B45 | isopropyl | 5-Cl-thiophen-3-yl-CH₂-S(=O)₂-NH⁓ |
| B36 | isopropyl | 5-CF₃-pyridin-2-yl-CH₂-S(=O)₂-NH⁓ | B46 | isopropyl | 5-Me-thiophen-3-yl-CH₂-S(=O)₂-NH⁓ |
| B37 | isopropyl | pyridin-2-yl-CH₂-S(=O)₂-NH⁓ | B47 | isopropyl | thiophen-3-yl-CH₂-S(=O)₂-NH⁓ |
| B38 | isopropyl | 6-Cl-pyridin-3-yl-CH₂-S(=O)₂-NH⁓ | C01 | n-propyl | 4-Me-benzyl-CH₂-S(=O)₂-NH⁓ |
| B39 | isopropyl | 6-Me-pyridin-3-yl-CH₂-S(=O)₂-NH⁓ | C02 | n-propyl | 4-Et-benzyl-CH₂-S(=O)₂-NH⁓ |
| B40 | isopropyl | 6-CF₃-pyridin-3-yl-CH₂-S(=O)₂-NH⁓ | C03 | n-propyl | 4-(MeOCH₂)-benzyl-CH₂-S(=O)₂-NH⁓ |

Fig. 5F

| ID | R¹ | structure | ID | R¹ | structure |
|---|---|---|---|---|---|
| C04 | n-propyl | 4-isopropyl-benzyl-SO₂NH- | C15 | n-propyl | 4-vinyl-benzyl-SO₂NH- |
| C05 | n-propyl | 4-n-propyl-benzyl-SO₂NH- | C16 | n-propyl | 4-ethynyl-benzyl-SO₂NH- |
| C06 | n-propyl | 4-Cl-benzyl-SO₂NH- | C17 | n-propyl | 4-isopropenyl-benzyl-SO₂NH- |
| C07 | n-propyl | 4-Br-benzyl-SO₂NH- | C18 | n-propyl | 4-propenyl-benzyl-SO₂NH- |
| C08 | n-propyl | 4-CF₃-benzyl-SO₂NH- | C19 | n-propyl | 4-(MeON=CH)-benzyl-SO₂NH- |
| C09 | n-propyl | 4-OCF₃-benzyl-SO₂NH- | C20 | n-propyl | benzothiazol-6-yl-methyl-SO₂NH- |
| C10 | n-propyl | 4-SCF₃-benzyl-SO₂NH- | C21 | n-propyl | 2,2-difluoro-benzo[1,3]dioxol-5-yl-methyl-SO₂NH- |
| C11 | n-propyl | 4-OMe-benzyl-SO₂NH- | C22 | n-propyl | 2,5-difluoro-benzyl-SO₂NH- |
| C12 | n-propyl | 4-CHF₂-benzyl-SO₂NH- | C23 | n-propyl | 2,3-difluoro-benzyl-SO₂NH- |
| C13 | n-propyl | 4-OCHF₂-benzyl-SO₂NH- | | | |
| C14 | n-propyl | 4-F-benzyl-SO₂NH- | | | |

Fig. 5H

| ID | R¹ | ![structure] |
|---|---|---|
| C42 | n-propyl | 5-chlorothien-2-yl-CH₂-SO₂-NH- |
| C43 | n-propyl | 5-methylthien-2-yl-CH₂-SO₂-NH- |
| C44 | n-propyl | thien-2-yl-CH₂-SO₂-NH- |
| C45 | n-propyl | 5-chlorothien-3-yl-CH₂-SO₂-NH- |
| C46 | n-propyl | 5-methylthien-3-yl-CH₂-SO₂-NH- |
| C47 | n-propyl | thien-3-yl-CH₂-SO₂-NH- |
| D01 | allyl | 4-methylphenyl-CH₂-SO₂-NH- |
| D02 | allyl | 4-ethylphenyl-CH₂-SO₂-NH- |
| D03 | allyl | 4-methoxymethylphenyl-CH₂-SO₂-NH- |
| D04 | allyl | 4-isopropylphenyl-CH₂-SO₂-NH- |

| ID | R¹ | |
|---|---|---|
| D05 | allyl | 4-n-propylphenyl-CH₂-SO₂-NH- |
| D06 | allyl | 4-chlorophenyl-CH₂-SO₂-NH- |
| D07 | allyl | 4-bromophenyl-CH₂-SO₂-NH- |
| D08 | allyl | 4-(CF₃)phenyl-CH₂-SO₂-NH- |
| D09 | allyl | 4-(OCF₃)phenyl-CH₂-SO₂-NH- |
| D10 | allyl | 4-(SCF₃)phenyl-CH₂-SO₂-NH- |
| D11 | allyl | 4-(OMe)phenyl-CH₂-SO₂-NH- |
| D12 | allyl | 4-(CHF₂)phenyl-CH₂-SO₂-NH- |
| D13 | allyl | 4-(OCHF₂)phenyl-CH₂-SO₂-NH- |
| D14 | allyl | 4-fluorophenyl-CH₂-SO₂-NH- |
| D15 | allyl | 4-vinylphenyl-CH₂-SO₂-NH- |

Fig. 5I

| ID | R$^1$ | ![sulfonamide] |
|---|---|---|
| D16 | allyl | 4-ethynylbenzyl sulfonamide |
| D17 | allyl | 4-(prop-1-en-2-yl)benzyl sulfonamide |
| D18 | allyl | 4-(prop-1-en-1-yl)benzyl sulfonamide |
| D19 | allyl | 4-((methoxyimino)methyl)benzyl sulfonamide |
| D20 | allyl | benzo[d]thiazol-5-ylmethyl sulfonamide |
| D21 | allyl | 2,2-difluorobenzo[d][1,3]dioxol-5-ylmethyl sulfonamide |
| D22 | allyl | 2,5-difluorobenzyl sulfonamide |
| D23 | allyl | 2,3-difluorobenzyl sulfonamide |
| D24 | allyl | 3,4-dimethylbenzyl sulfonamide |

| ID | R$^1$ | |
|---|---|---|
| D25 | allyl | 3-fluoro-4-methylbenzyl sulfonamide |
| D26 | allyl | 3-chloro-4-methylbenzyl sulfonamide |
| D27 | allyl | 3,4-dichlorobenzyl sulfonamide |
| D28 | allyl | 4-chloro-3-fluorobenzyl sulfonamide |
| D29 | allyl | 2,4-dimethylbenzyl sulfonamide |
| D30 | allyl | 2-fluoro-4-methylbenzyl sulfonamide |
| D31 | allyl | 4-bromo-2-fluorobenzyl sulfonamide |
| D32 | allyl | 4-cyano-2-fluorobenzyl sulfonamide |

| | | | | | |
|---|---|---|---|---|---|
|  | | | | | |
| ID | R¹ |  | ID | R¹ | |
| D33 | allyl |  | D43 | allyl |  |
| D34 | allyl |  | D44 | allyl |  |
| D35 | allyl |  | D45 | allyl |  |
| D36 | allyl |  | D46 | allyl |  |
| D37 | allyl |  | D47 | allyl |  |
| D38 | allyl |  | E01 | cyclopropyl |  |
| D39 | allyl |  | E02 | cyclopropyl |  |
| D40 | allyl |  | E03 | cyclopropyl |  |
| D41 | allyl |  | E04 | cyclopropyl |  |
| D42 | allyl | | E05 | cyclopropyl |  |

| | | |
|---|---|---|
| |  | |
| ID | R¹ |  |
| E06 | cyclopropyl |  |
| E07 | cyclopropyl |  |
| E08 | cyclopropyl |  |
| E09 | cyclopropyl |  |
| E10 | cyclopropyl |  |
| E11 | cyclopropyl |  |
| E12 | cyclopropyl |  |
| E13 | cyclopropyl |  |
| E14 | cyclopropyl |  |
| E15 | cyclopropyl |  |
| E16 | cyclopropyl |  |

| ID | R¹ | |
|---|---|---|
| E17 | cyclopropyl |  |
| E18 | cyclopropyl |  |
| E19 | cyclopropyl |  |
| E20 | cyclopropyl |  |
| E21 | cyclopropyl |  |
| E22 | cyclopropyl |  |
| E23 | cyclopropyl |  |
| E24 | cyclopropyl |  |
| E25 | cyclopropyl | |

Fig. 5L

| | | | ID | R¹ | |
|---|---|---|---|---|---|
| ID | R¹ | | E35 | cyclopropyl | 5-methyl-pyridin-2-yl-CH₂-S(O)₂-NH- |
| E26 | cyclopropyl | 3-Cl-4-methyl-phenyl-CH₂-S(O)₂-NH- | E36 | cyclopropyl | 5-CF₃-pyridin-2-yl-CH₂-S(O)₂-NH- |
| E27 | cyclopropyl | 3,4-diCl-phenyl-CH₂-S(O)₂-NH- | E37 | cyclopropyl | pyridin-2-yl-CH₂-S(O)₂-NH- |
| E28 | cyclopropyl | 3-F-4-Cl-phenyl-CH₂-S(O)₂-NH- | E38 | cyclopropyl | 6-Cl-pyridin-3-yl-CH₂-S(O)₂-NH- |
| E29 | cyclopropyl | 2,4-dimethyl-phenyl-CH₂-S(O)₂-NH- | E39 | cyclopropyl | 6-methyl-pyridin-3-yl-CH₂-S(O)₂-NH- |
| E30 | cyclopropyl | 2-F-4-methyl-phenyl-CH₂-S(O)₂-NH- | E40 | cyclopropyl | 6-CF₃-pyridin-3-yl-CH₂-S(O)₂-NH- |
| E31 | cyclopropyl | 2-F-4-Br-phenyl-CH₂-S(O)₂-NH- | E41 | cyclopropyl | pyridin-3-yl-CH₂-S(O)₂-NH- |
| E32 | cyclopropyl | 2-F-4-CN-phenyl-CH₂-S(O)₂-NH- | E42 | cyclopropyl | 5-Cl-thien-2-yl-CH₂-S(O)₂-NH- |
| E33 | cyclopropyl | 2-Cl-4-methyl-phenyl-CH₂-S(O)₂-NH- | E43 | cyclopropyl | 5-methyl-thien-2-yl-CH₂-S(O)₂-NH- |
| E34 | cyclopropyl | 5-Cl-pyridin-2-yl-CH₂-S(O)₂-NH- | E44 | cyclopropyl | thien-2-yl-CH₂-S(O)₂-NH- |

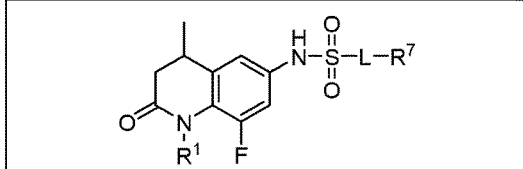

Fig. 5M

| ID | R¹ | (sulfonamide group) | ID | R¹ | (sulfonamide group) |
|---|---|---|---|---|---|
| E45 | cyclopropyl | 5-chlorothiophen-3-ylmethyl sulfonamide | F08 | cyclobutyl | 4-(CF₃)benzyl sulfonamide |
| E46 | cyclopropyl | 5-methylthiophen-3-ylmethyl sulfonamide | F09 | cyclobutyl | 4-(CF₃O)benzyl sulfonamide |
| E47 | cyclopropyl | thiophen-3-ylmethyl sulfonamide | F10 | cyclobutyl | 4-(F₃CS)benzyl sulfonamide |
| F01 | cyclobutyl | 4-methylbenzyl sulfonamide | F11 | cyclobutyl | 4-(MeO)benzyl sulfonamide |
| F02 | cyclobutyl | 4-ethylbenzyl sulfonamide | F12 | cyclobutyl | 4-(HF₂C)benzyl sulfonamide |
| F03 | cyclobutyl | 4-(methoxymethyl)benzyl sulfonamide | F13 | cyclobutyl | 4-(HF₂CO)benzyl sulfonamide |
| F04 | cyclobutyl | 4-isopropylbenzyl sulfonamide | F14 | cyclobutyl | 4-fluorobenzyl sulfonamide |
| F05 | cyclobutyl | 4-propylbenzyl sulfonamide | F15 | cyclobutyl | 4-vinylbenzyl sulfonamide |
| F06 | cyclobutyl | 4-chlorobenzyl sulfonamide | F16 | cyclobutyl | 4-ethynylbenzyl sulfonamide |
| F07 | cyclobutyl | 4-bromobenzyl sulfonamide | F17 | cyclobutyl | 4-(prop-1-en-2-yl)benzyl sulfonamide |
|  |  |  | F18 | cyclobutyl | 4-(prop-1-en-1-yl)benzyl sulfonamide |

Fig. 5N

| ID | R¹ | ![structure] |
|---|---|---|
| F19 | cyclobutyl | 4-(MeON=CH)-C6H4-CH2-S(O)2-NH- |
| F20 | cyclobutyl | benzothiazol-5-yl-CH2-S(O)2-NH- |
| F21 | cyclobutyl | 2,2-difluoro-benzo[1,3]dioxol-5-yl-CH2-S(O)2-NH- |
| F22 | cyclobutyl | 2,5-difluorophenyl-CH2-S(O)2-NH- |
| F23 | cyclobutyl | 2,3-difluorophenyl-CH2-S(O)2-NH- |
| F24 | cyclobutyl | 3,4-dimethylphenyl-CH2-S(O)2-NH- |
| F25 | cyclobutyl | 3-fluoro-4-methylphenyl-CH2-S(O)2-NH- |
| F26 | cyclobutyl | 3-chloro-4-methylphenyl-CH2-S(O)2-NH- |
| F27 | cyclobutyl | 3,4-dichlorophenyl-CH2-S(O)2-NH- |

| ID | R¹ | |
|---|---|---|
| F28 | cyclobutyl | 4-chloro-3-fluorophenyl-CH2-S(O)2-NH- |
| F29 | cyclobutyl | 2,4-dimethylphenyl-CH2-S(O)2-NH- |
| F30 | cyclobutyl | 2-fluoro-4-methylphenyl-CH2-S(O)2-NH- |
| F31 | cyclobutyl | 4-bromo-2-fluorophenyl-CH2-S(O)2-NH- |
| F32 | cyclobutyl | 4-cyano-2-fluorophenyl-CH2-S(O)2-NH- |
| F33 | cyclobutyl | 2-chloro-4-methylphenyl-CH2-S(O)2-NH- |
| F34 | cyclobutyl | 5-chloropyridin-2-yl-CH2-S(O)2-NH- |
| F35 | cyclobutyl | 5-methylpyridin-2-yl-CH2-S(O)2-NH- |
| F36 | cyclobutyl | 5-(trifluoromethyl)pyridin-2-yl-CH2-S(O)2-NH- |

Fig. 5O

| ID | R¹ | (=O)-L-R⁷) |
|---|---|---|
| F37 | cyclobutyl | pyridin-2-ylmethyl sulfonamide |
| F38 | cyclobutyl | (6-chloropyridin-3-yl)methyl sulfonamide |
| F39 | cyclobutyl | (6-methylpyridin-3-yl)methyl sulfonamide |
| F40 | cyclobutyl | (6-trifluoromethylpyridin-3-yl)methyl sulfonamide |
| F41 | cyclobutyl | pyridin-3-ylmethyl sulfonamide |
| F42 | cyclobutyl | (5-chlorothiophen-2-yl)methyl sulfonamide |
| F43 | cyclobutyl | (5-methylthiophen-2-yl)methyl sulfonamide |
| F44 | cyclobutyl | thiophen-2-ylmethyl sulfonamide |
| F45 | cyclobutyl | (5-chlorothiophen-3-yl)methyl sulfonamide |
| F46 | cyclobutyl | (5-methylthiophen-3-yl)methyl sulfonamide |

| ID | R¹ | |
|---|---|---|
| F47 | cyclobutyl | thiophen-3-ylmethyl sulfonamide |
| G01 | 2,2,2-trifluoroethyl | (4-methylphenyl)methyl sulfonamide |
| G02 | 2,2,2-trifluoroethyl | (4-ethylphenyl)methyl sulfonamide |
| G03 | 2,2,2-trifluoroethyl | (4-methoxyphenyl)methyl sulfonamide |
| G04 | 2,2,2-trifluoroethyl | (4-isopropylphenyl)methyl sulfonamide |
| G05 | 2,2,2-trifluoroethyl | (4-propylphenyl)methyl sulfonamide |
| G06 | 2,2,2-trifluoroethyl | (4-chlorophenyl)methyl sulfonamide |
| G07 | 2,2,2-trifluoroethyl | (4-bromophenyl)methyl sulfonamide |
| G08 | 2,2,2-trifluoroethyl | (4-trifluoromethylphenyl)methyl sulfonamide |
| G09 | 2,2,2-trifluoroethyl | (4-trifluoromethoxyphenyl)methyl sulfonamide |
| G10 | 2,2,2-trifluoroethyl | (4-trifluoromethylthiophenyl)methyl sulfonamide |

| ID | R¹ |  | ID | R¹ | |
|---|---|---|---|---|---|
| G11 | 2,2,2-trifluoroethyl |  | G21 | 2,2,2-trifluoroethyl |  |
| G12 | 2,2,2-trifluoroethyl |  | G22 | 2,2,2-trifluoroethyl |  |
| G13 | 2,2,2-trifluoroethyl |  | G23 | 2,2,2-trifluoroethyl |  |
| G14 | 2,2,2-trifluoroethyl |  | G24 | 2,2,2-trifluoroethyl |  |
| G15 | 2,2,2-trifluoroethyl |  | G25 | 2,2,2-trifluoroethyl |  |
| G16 | 2,2,2-trifluoroethyl |  | G26 | 2,2,2-trifluoroethyl |  |
| G17 | 2,2,2-trifluoroethyl |  | G27 | 2,2,2-trifluoroethyl |  |
| G18 | 2,2,2-trifluoroethyl |  | G28 | 2,2,2-trifluoroethyl |  |
| G19 | 2,2,2-trifluoroethyl |  | | | |
| G20 | 2,2,2-trifluoroethyl |  | | | |

Fig. 5Q

| ID | R¹ | ![](N-S-L-R⁷ sulfonamide) | ID | R¹ | |
|---|---|---|---|---|---|
| G29 | 2,2,2-trifluoroethyl | dimethylphenyl-CH₂-SO₂NH- | G38 | 2,2,2-trifluoroethyl | 6-chloropyridin-3-yl-CH₂-SO₂NH- |
| G30 | 2,2,2-trifluoroethyl | 2-fluoro-methylphenyl-CH₂-SO₂NH- | G39 | 2,2,2-trifluoroethyl | 6-methylpyridin-3-yl-CH₂-SO₂NH- |
| G31 | 2,2,2-trifluoroethyl | 4-bromo-2-fluorophenyl-CH₂-SO₂NH- | G40 | 2,2,2-trifluoroethyl | 6-(trifluoromethyl)pyridin-3-yl-CH₂-SO₂NH- |
| G32 | 2,2,2-trifluoroethyl | 4-cyano-2-fluorophenyl-CH₂-SO₂NH- | G41 | 2,2,2-trifluoroethyl | pyridin-3-yl-CH₂-SO₂NH- |
| G33 | 2,2,2-trifluoroethyl | 2-chloro-methylphenyl-CH₂-SO₂NH- | G42 | 2,2,2-trifluoroethyl | 5-chlorothiophen-2-yl-CH₂-SO₂NH- |
| G34 | 2,2,2-trifluoroethyl | 5-chloropyridin-2-yl-CH₂-SO₂NH- | G43 | 2,2,2-trifluoroethyl | 5-methylthiophen-2-yl-CH₂-SO₂NH- |
| G35 | 2,2,2-trifluoroethyl | 5-methylpyridin-2-yl-CH₂-SO₂NH- | G44 | 2,2,2-trifluoroethyl | thiophen-2-yl-CH₂-SO₂NH- |
| G36 | 2,2,2-trifluoroethyl | 5-(trifluoromethyl)pyridin-2-yl-CH₂-SO₂NH- | G45 | 2,2,2-trifluoroethyl | 5-chlorothiophen-3-yl-CH₂-SO₂NH- |
| G37 | 2,2,2-trifluoroethyl | pyridin-2-yl-CH₂-SO₂NH- | G46 | 2,2,2-trifluoroethyl | 5-methylthiophen-3-yl-CH₂-SO₂NH- |
| | | | G47 | 2,2,2-trifluoroethyl | thiophen-3-yl-CH₂-SO₂NH- |

Fig. 5R

| | | | | | |
|---|---|---|---|---|---|
| ID | R¹ | $\overset{H}{N}-\underset{O}{\overset{O}{S}}-L-R^7$ | ID | R¹ | |
| H01 | 2-cyanoethyl | 4-methylbenzyl sulfonamide | H12 | 2-cyanoethyl | 4-(difluoromethyl)benzyl sulfonamide |
| H02 | 2-cyanoethyl | 4-ethylbenzyl sulfonamide | H13 | 2-cyanoethyl | 4-(difluoromethoxy)benzyl sulfonamide |
| H03 | 2-cyanoethyl | 4-methoxymethylbenzyl sulfonamide | H14 | 2-cyanoethyl | 4-fluorobenzyl sulfonamide |
| H04 | 2-cyanoethyl | 4-isopropylbenzyl sulfonamide | H15 | 2-cyanoethyl | 4-vinylbenzyl sulfonamide |
| H05 | 2-cyanoethyl | 4-ethylbenzyl sulfonamide | H16 | 2-cyanoethyl | 4-ethynylbenzyl sulfonamide |
| H06 | 2-cyanoethyl | 4-chlorobenzyl sulfonamide | H17 | 2-cyanoethyl | 4-isopropenylbenzyl sulfonamide |
| H07 | 2-cyanoethyl | 4-bromobenzyl sulfonamide | H18 | 2-cyanoethyl | 4-propenylbenzyl sulfonamide |
| H08 | 2-cyanoethyl | 4-(trifluoromethyl)benzyl sulfonamide | H19 | 2-cyanoethyl | 4-(methoxyiminomethyl)benzyl sulfonamide |
| H09 | 2-cyanoethyl | 4-(trifluoromethoxy)benzyl sulfonamide | H20 | 2-cyanoethyl | benzothiazol-5-ylmethyl sulfonamide |
| H10 | 2-cyanoethyl | 4-(trifluoromethylthio)benzyl sulfonamide | H21 | 2-cyanoethyl | 2,2-difluoro-1,3-benzodioxol-5-ylmethyl sulfonamide |
| H11 | 2-cyanoethyl | 4-methoxybenzyl sulfonamide | | | |

Fig. 5S

| ID | R¹ | ₂-L-R⁷) | ID | R¹ | |
|---|---|---|---|---|---|
| H22 | 2-cyanoethyl | 2,5-difluorobenzyl-SO₂-NH- | H30 | 2-cyanoethyl | 2-fluoro-4-methylbenzyl-SO₂-NH- |
| H23 | 2-cyanoethyl | 2,3-difluorobenzyl-SO₂-NH- | H31 | 2-cyanoethyl | 4-bromo-2-fluorobenzyl-SO₂-NH- |
| H24 | 2-cyanoethyl | 3,4-dimethylbenzyl-SO₂-NH- | H32 | 2-cyanoethyl | 4-cyano-2-fluorobenzyl-SO₂-NH- |
| H25 | 2-cyanoethyl | 3-fluoro-4-methylbenzyl-SO₂-NH- | H33 | 2-cyanoethyl | 2-chloro-4-methylbenzyl-SO₂-NH- |
| H26 | 2-cyanoethyl | 3-chloro-4-methylbenzyl-SO₂-NH- | H34 | 2-cyanoethyl | 5-chloropyridin-2-yl-methyl-SO₂-NH- |
| H27 | 2-cyanoethyl | 3,4-dichlorobenzyl-SO₂-NH- | H35 | 2-cyanoethyl | 5-methylpyridin-2-yl-methyl-SO₂-NH- |
| H28 | 2-cyanoethyl | 4-chloro-3-fluorobenzyl-SO₂-NH- | H36 | 2-cyanoethyl | 5-(trifluoromethyl)pyridin-2-yl-methyl-SO₂-NH- |
| H29 | 2-cyanoethyl | 2,4-dimethylbenzyl-SO₂-NH- | H37 | 2-cyanoethyl | pyridin-2-yl-methyl-SO₂-NH- |
| | | | H38 | 2-cyanoethyl | 6-chloropyridin-3-yl-methyl-SO₂-NH- |

| ID | R¹ |  | ID | R¹ | |
|---|---|---|---|---|---|
| H39 | 2-cyanoethyl |  | I02 | 2-methoxy-2-oxoethyl |  |
| H40 | 2-cyanoethyl |  | I03 | 2-methoxy-2-oxoethyl |  |
| H41 | 2-cyanoethyl |  | I04 | 2-methoxy-2-oxoethyl |  |
| H42 | 2-cyanoethyl |  | I05 | 2-methoxy-2-oxoethyl |  |
| H43 | 2-cyanoethyl |  | I06 | 2-methoxy-2-oxoethyl |  |
| H44 | 2-cyanoethyl |  | I07 | 2-methoxy-2-oxoethyl |  |
| H45 | 2-cyanoethyl |  | I08 | 2-methoxy-2-oxoethyl |  |
| H46 | 2-cyanoethyl |  | I09 | 2-methoxy-2-oxoethyl |  |
| H47 | 2-cyanoethyl |  | I10 | 2-methoxy-2-oxoethyl |  |
| I01 | 2-methoxy-2-oxoethyl |  | I11 | 2-methoxy-2-oxoethyl |  |
| | | | I12 | 2-methoxy-2-oxoethyl |  |

Fig. 5U

| | | | ID | R¹ | |
|---|---|---|---|---|---|
| ID | R¹ | | I23 | 2-methoxy-2-oxoethyl | |
| I13 | 2-methoxy-2-oxoethyl | | I24 | 2-methoxy-2-oxoethyl | |
| I14 | 2-methoxy-2-oxoethyl | | I25 | 2-methoxy-2-oxoethyl | |
| I15 | 2-methoxy-2-oxoethyl | | I26 | 2-methoxy-2-oxoethyl | |
| I16 | 2-methoxy-2-oxoethyl | | I27 | 2-methoxy-2-oxoethyl | |
| I17 | 2-methoxy-2-oxoethyl | | I28 | 2-methoxy-2-oxoethyl | |
| I18 | 2-methoxy-2-oxoethyl | | I29 | 2-methoxy-2-oxoethyl | |
| I19 | 2-methoxy-2-oxoethyl | | I30 | 2-methoxy-2-oxoethyl | |
| I20 | 2-methoxy-2-oxoethyl | | | | |
| I21 | 2-methoxy-2-oxoethyl | | | | |
| I22 | 2-methoxy-2-oxoethyl | | | | |

Fig. 5V

| ID | R¹ | ⟶N(H)-S(O)(O)-L-R⁷ | ID | R¹ | ⟶N(H)-S(O)(O)-L-R⁷ |
|---|---|---|---|---|---|
| I31 | 2-methoxy-2-oxoethyl | 4-bromo-2-fluorobenzyl sulfonamide | I41 | 2-methoxy-2-oxoethyl | pyridin-3-ylmethyl sulfonamide |
| I32 | 2-methoxy-2-oxoethyl | 4-cyano-2-fluorobenzyl sulfonamide | I42 | 2-methoxy-2-oxoethyl | (5-chlorothiophen-2-yl)methyl sulfonamide |
| I33 | 2-methoxy-2-oxoethyl | 2-chloro-4-methylbenzyl sulfonamide | I43 | 2-methoxy-2-oxoethyl | (5-methylthiophen-2-yl)methyl sulfonamide |
| I34 | 2-methoxy-2-oxoethyl | (5-chloropyridin-2-yl)methyl sulfonamide | I44 | 2-methoxy-2-oxoethyl | thiophen-2-ylmethyl sulfonamide |
| I35 | 2-methoxy-2-oxoethyl | (5-methylpyridin-2-yl)methyl sulfonamide | I45 | 2-methoxy-2-oxoethyl | (5-chlorothiophen-3-yl)methyl sulfonamide |
| I36 | 2-methoxy-2-oxoethyl | (5-trifluoromethylpyridin-2-yl)methyl sulfonamide | I46 | 2-methoxy-2-oxoethyl | (5-methylthiophen-3-yl)methyl sulfonamide |
| I37 | 2-methoxy-2-oxoethyl | pyridin-2-ylmethyl sulfonamide | I47 | 2-methoxy-2-oxoethyl | thiophen-3-ylmethyl sulfonamide |
| I38 | 2-methoxy-2-oxoethyl | (6-chloropyridin-3-yl)methyl sulfonamide | J01 | cyclopropyl-methyl | 4-methylbenzyl sulfonamide |
| I39 | 2-methoxy-2-oxoethyl | (6-methylpyridin-3-yl)methyl sulfonamide | J02 | cyclopropyl-methyl | 4-ethylbenzyl sulfonamide |
| I40 | 2-methoxy-2-oxoethyl | (6-trifluoromethylpyridin-3-yl)methyl sulfonamide | J03 | cyclopropyl-methyl | 4-(methoxymethyl)benzyl sulfonamide |

Fig. 5W

| ID | R¹ | 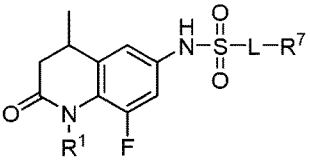 | ID | R¹ | |
|---|---|---|---|---|---|
| J04 | cyclopropyl-methyl | 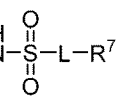 | J15 | cyclopropyl-methyl | 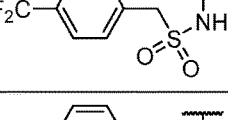 |
| J05 | cyclopropyl-methyl | 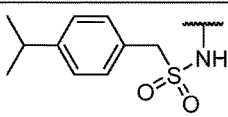 | J16 | cyclopropyl-methyl | 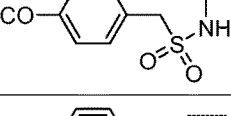 |
| J06 | cyclopropyl-methyl | 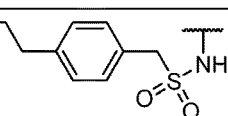 | J17 | cyclopropyl-methyl | 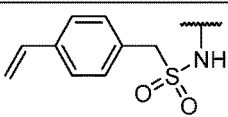 |
| J07 | cyclopropyl-methyl | 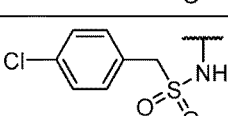 | J18 | cyclopropyl-methyl | 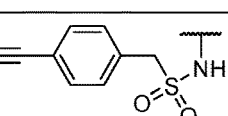 |
| J08 | cyclopropyl-methyl | 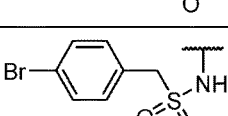 | J19 | cyclopropyl-methyl | 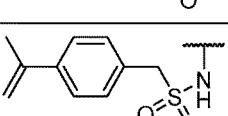 |
| J09 | cyclopropyl-methyl | 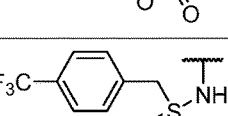 | J20 | cyclopropyl-methyl | 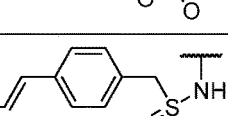 |
| J10 | cyclopropyl-methyl | 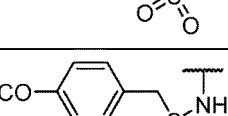 | J21 | cyclopropyl-methyl | 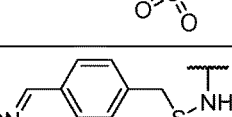 |
| J11 | cyclopropyl-methyl | 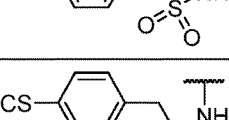 | J22 | cyclopropyl-methyl | 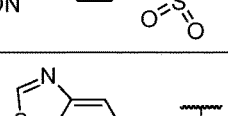 |
| J12 | cyclopropyl-methyl | 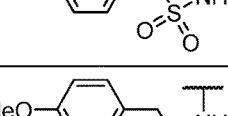 | J23 | cyclopropyl-methyl | 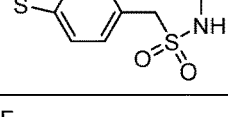 |
| J13 | cyclopropyl-methyl | 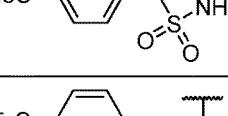 | | | |
| J14 | cyclopropyl-methyl | 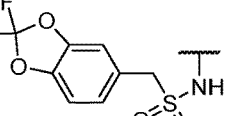 | | | |

Fig. 5X

| ID | R¹ | -L-R⁷) |
|---|---|---|
| J24 | cyclopropyl-methyl | 3,4-dimethylphenyl-CH₂-S(O₂)NH- |
| J25 | cyclopropyl-methyl | 3-F-4-methylphenyl-CH₂-S(O₂)NH- |
| J26 | cyclopropyl-methyl | 3-Cl-4-methylphenyl-CH₂-S(O₂)NH- |
| J27 | cyclopropyl-methyl | 3,4-dichlorophenyl-CH₂-S(O₂)NH- |
| J28 | cyclopropyl-methyl | 3-F-4-Cl-phenyl-CH₂-S(O₂)NH- |
| J29 | cyclopropyl-methyl | 2,4-dimethylphenyl-CH₂-S(O₂)NH- |
| J30 | cyclopropyl-methyl | 2-F-4-methylphenyl-CH₂-S(O₂)NH- |
| J31 | cyclopropyl-methyl | 4-Br-2-F-phenyl-CH₂-S(O₂)NH- |

| ID | R¹ | |
|---|---|---|
| J32 | cyclopropyl-methyl | 3-F-4-CN-phenyl-CH₂-S(O₂)NH- |
| J33 | cyclopropyl-methyl | 2-Cl-4-methylphenyl-CH₂-S(O₂)NH- |
| J34 | cyclopropyl-methyl | 5-Cl-pyridin-2-yl-CH₂-S(O₂)NH- |
| J35 | cyclopropyl-methyl | 5-methyl-pyridin-2-yl-CH₂-S(O₂)NH- |
| J36 | cyclopropyl-methyl | 5-CF₃-pyridin-2-yl-CH₂-S(O₂)NH- |
| J37 | cyclopropyl-methyl | pyridin-2-yl-CH₂-S(O₂)NH- |
| J38 | cyclopropyl-methyl | 6-Cl-pyridin-3-yl-CH₂-S(O₂)NH- |
| J39 | cyclopropyl-methyl | 6-methyl-pyridin-3-yl-CH₂-S(O₂)NH- |
| J40 | cyclopropyl-methyl | 6-CF₃-pyridin-3-yl-CH₂-S(O₂)NH- |
| J41 | cyclopropyl-methyl | pyridin-3-yl-CH₂-S(O₂)NH- |

Fig. 5Y

| ID | R¹ | ![structure] |
|---|---|---|
| J42 | cyclopropyl-methyl | 5-chlorothiophen-2-yl-CH₂-SO₂-NH- |
| J43 | cyclopropyl-methyl | 5-methylthiophen-2-yl-CH₂-SO₂-NH- |
| J44 | cyclopropyl-methyl | thiophen-2-yl-CH₂-SO₂-NH- |
| J45 | cyclopropyl-methyl | 5-chlorothiophen-3-yl-CH₂-SO₂-NH- |
| J46 | cyclopropyl-methyl | 5-methylthiophen-3-yl-CH₂-SO₂-NH- |
| J47 | cyclopropyl-methyl | thiophen-3-yl-CH₂-SO₂-NH- |
| K01 | 2-methoxyethyl | 4-methylphenyl-CH₂-SO₂-NH- |
| K02 | 2-methoxyethyl | 4-ethylphenyl-CH₂-SO₂-NH- |
| K03 | 2-methoxyethyl | 4-(methoxymethyl)phenyl-CH₂-SO₂-NH- |
| K04 | 2-methoxyethyl | 4-isopropylphenyl-CH₂-SO₂-NH- |

| ID | R¹ | structure |
|---|---|---|
| K05 | 2-methoxyethyl | 4-propylphenyl-CH₂-SO₂-NH- |
| K06 | 2-methoxyethyl | 4-chlorophenyl-CH₂-SO₂-NH- |
| K07 | 2-methoxyethyl | 4-bromophenyl-CH₂-SO₂-NH- |
| K08 | 2-methoxyethyl | 4-(trifluoromethyl)phenyl-CH₂-SO₂-NH- |
| K09 | 2-methoxyethyl | 4-(trifluoromethoxy)phenyl-CH₂-SO₂-NH- |
| K10 | 2-methoxyethyl | 4-(trifluoromethylthio)phenyl-CH₂-SO₂-NH- |
| K11 | 2-methoxyethyl | 4-methoxyphenyl-CH₂-SO₂-NH- |
| K12 | 2-methoxyethyl | 4-(difluoromethyl)phenyl-CH₂-SO₂-NH- |
| K13 | 2-methoxyethyl | 4-(difluoromethoxy)phenyl-CH₂-SO₂-NH- |
| K14 | 2-methoxyethyl | 4-fluorophenyl-CH₂-SO₂-NH- |
| K15 | 2-methoxyethyl | 4-vinylphenyl-CH₂-SO₂-NH- |

| ID | R¹ | |
|---|---|---|
| K16 | 2-methoxyethyl |  |
| K17 | 2-methoxyethyl |  |
| K18 | 2-methoxyethyl |  |
| K19 | 2-methoxyethyl |  |
| K20 | 2-methoxyethyl |  |
| K21 | 2-methoxyethyl |  |
| K22 | 2-methoxyethyl |  |
| K23 | 2-methoxyethyl |  |
| K24 | 2-methoxyethyl |  |

| ID | R¹ | |
|---|---|---|
| K25 | 2-methoxyethyl |  |
| K26 | 2-methoxyethyl |  |
| K27 | 2-methoxyethyl |  |
| K28 | 2-methoxyethyl |  |
| K29 | 2-methoxyethyl |  |
| K30 | 2-methoxyethyl |  |
| K31 | 2-methoxyethyl |  |
| K32 | 2-methoxyethyl |  |

Fig. 5AA

| ID | R¹ | (O)-L-R⁷ core with tetrahydroquinolinone, F) |
|---|---|---|
| K33 | 2-methoxyethyl | 2-chloro-4-methylbenzyl sulfonamide |
| K34 | 2-methoxyethyl | (5-chloropyridin-2-yl)methyl sulfonamide |
| K35 | 2-methoxyethyl | (5-methylpyridin-2-yl)methyl sulfonamide |
| K36 | 2-methoxyethyl | (5-trifluoromethylpyridin-2-yl)methyl sulfonamide |
| K37 | 2-methoxyethyl | pyridin-2-ylmethyl sulfonamide |
| K38 | 2-methoxyethyl | (6-chloropyridin-3-yl)methyl sulfonamide |
| K39 | 2-methoxyethyl | (6-methylpyridin-3-yl)methyl sulfonamide |
| K40 | 2-methoxyethyl | (6-trifluoromethylpyridin-3-yl)methyl sulfonamide |
| K41 | 2-methoxyethyl | pyridin-3-ylmethyl sulfonamide |
| K42 | 2-methoxyethyl | (5-chlorothiophen-2-yl)methyl sulfonamide |

| ID | R¹ | |
|---|---|---|
| K43 | 2-methoxyethyl | (5-methylthiophen-2-yl)methyl sulfonamide |
| K44 | 2-methoxyethyl | thiophen-2-ylmethyl sulfonamide |
| K45 | 2-methoxyethyl | (5-chlorothiophen-3-yl)methyl sulfonamide |
| K46 | 2-methoxyethyl | (5-methylthiophen-3-yl)methyl sulfonamide |
| K47 | 2-methoxyethyl | thiophen-3-ylmethyl sulfonamide |
| L01 | 2,2-difluoroethyl | (4-methylphenyl)methyl sulfonamide |
| L02 | 2,2-difluoroethyl | (4-ethylphenyl)methyl sulfonamide |
| L03 | 2,2-difluoroethyl | (4-methoxymethylphenyl)methyl sulfonamide |
| L04 | 2,2-difluoroethyl | (4-isopropylphenyl)methyl sulfonamide |
| L05 | 2,2-difluoroethyl | (4-propylphenyl)methyl sulfonamide |

Fig. 5BB

| ID | R¹ | structure | ID | R¹ | structure |
|---|---|---|---|---|---|
| L06 | 2,2-difluoroethyl | 4-Cl-C6H4-CH2-S(O)2-NH- | L17 | 2,2-difluoroethyl | 4-isopropenyl-C6H4-CH2-S(O)2-NH- |
| L07 | 2,2-difluoroethyl | 4-Br-C6H4-CH2-S(O)2-NH- | L18 | 2,2-difluoroethyl | 4-(1-propenyl)-C6H4-CH2-S(O)2-NH- |
| L08 | 2,2-difluoroethyl | 4-CF3-C6H4-CH2-S(O)2-NH- | L19 | 2,2-difluoroethyl | 4-(MeON=CH)-C6H4-CH2-S(O)2-NH- |
| L09 | 2,2-difluoroethyl | 4-F3CO-C6H4-CH2-S(O)2-NH- | L20 | 2,2-difluoroethyl | benzothiazol-5-yl-CH2-S(O)2-NH- |
| L10 | 2,2-difluoroethyl | 4-F3CS-C6H4-CH2-S(O)2-NH- | L21 | 2,2-difluoroethyl | 2,2-difluoro-1,3-benzodioxol-5-yl-CH2-S(O)2-NH- |
| L11 | 2,2-difluoroethyl | 4-MeO-C6H4-CH2-S(O)2-NH- | L22 | 2,2-difluoroethyl | 2,5-difluorophenyl-CH2-S(O)2-NH- |
| L12 | 2,2-difluoroethyl | 4-HF2C-C6H4-CH2-S(O)2-NH- | L23 | 2,2-difluoroethyl | 2,3-difluorophenyl-CH2-S(O)2-NH- |
| L13 | 2,2-difluoroethyl | 4-HF2CO-C6H4-CH2-S(O)2-NH- | L24 | 2,2-difluoroethyl | 3,4-dimethylphenyl-CH2-S(O)2-NH- |
| L14 | 2,2-difluoroethyl | 4-F-C6H4-CH2-S(O)2-NH- | L25 | 2,2-difluoroethyl | 3-F-4-Me-C6H3-CH2-S(O)2-NH- |
| L15 | 2,2-difluoroethyl | 4-vinyl-C6H4-CH2-S(O)2-NH- | | | |
| L16 | 2,2-difluoroethyl | 4-ethynyl-C6H4-CH2-S(O)2-NH- | | | |

Fig. 5CC

| ID | R¹ | ![structure] |
|---|---|---|
| L26 | 2,2-difluoroethyl | 3-Cl, 4-methyl benzyl sulfonamide |
| L27 | 2,2-difluoroethyl | 3,4-dichloro benzyl sulfonamide |
| L28 | 2,2-difluoroethyl | 3-F, 4-Cl benzyl sulfonamide |
| L29 | 2,2-difluoroethyl | 2,4-dimethyl benzyl sulfonamide |
| L30 | 2,2-difluoroethyl | 2-F, 4-methyl benzyl sulfonamide |
| L31 | 2,2-difluoroethyl | 4-Br, 2-F benzyl sulfonamide |
| L32 | 2,2-difluoroethyl | 4-CN, 2-F benzyl sulfonamide |
| L33 | 2,2-difluoroethyl | 2-Cl, 4-methyl benzyl sulfonamide |
| L34 | 2,2-difluoroethyl | 5-Cl-pyridin-2-yl methyl sulfonamide |

| ID | R¹ | |
|---|---|---|
| L35 | 2,2-difluoroethyl | 5-methyl-pyridin-2-yl methyl sulfonamide |
| L36 | 2,2-difluoroethyl | 5-CF₃-pyridin-2-yl methyl sulfonamide |
| L37 | 2,2-difluoroethyl | pyridin-2-yl methyl sulfonamide |
| L38 | 2,2-difluoroethyl | 6-Cl-pyridin-3-yl methyl sulfonamide |
| L39 | 2,2-difluoroethyl | 6-methyl-pyridin-3-yl methyl sulfonamide |
| L40 | 2,2-difluoroethyl | 6-CF₃-pyridin-3-yl methyl sulfonamide |
| L41 | 2,2-difluoroethyl | pyridin-3-yl methyl sulfonamide |
| L42 | 2,2-difluoroethyl | 5-Cl-thiophen-2-yl methyl sulfonamide |
| L43 | 2,2-difluoroethyl | 5-methyl-thiophen-2-yl methyl sulfonamide |
| L44 | 2,2-difluoroethyl | thiophen-2-yl methyl sulfonamide |

Fig. 5DD

| ID | R¹ | 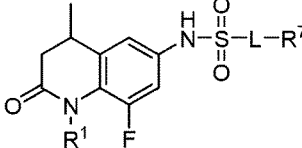 | ID | R¹ | |
|---|---|---|---|---|---|
| L45 | 2,2-difluoroethyl | 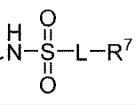 | M08 | methoxy-methyl | 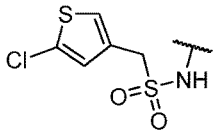 |
| L46 | 2,2-difluoroethyl | 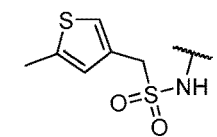 | M09 | methoxy-methyl | 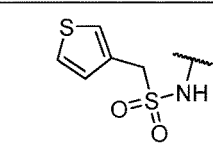 |
| L47 | 2,2-difluoroethyl | 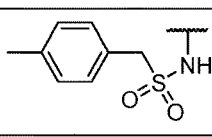 | M10 | methoxy-methyl | 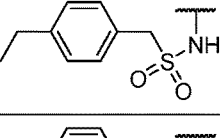 |
| M01 | methoxy-methyl | 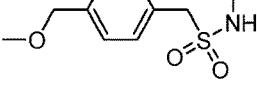 | M11 | methoxy-methyl | 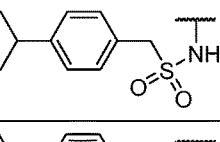 |
| M02 | methoxy-methyl | 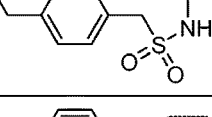 | M12 | methoxy-methyl | 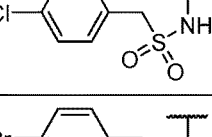 |
| M03 | methoxy-methyl | 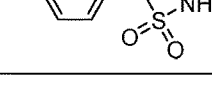 | M13 | methoxy-methyl | 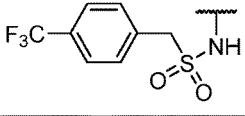 |
| M04 | methoxy-methyl | 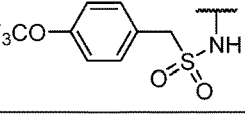 | M14 | methoxy-methyl | 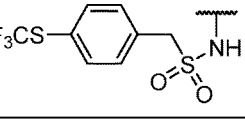 |
| M05 | methoxy-methyl | 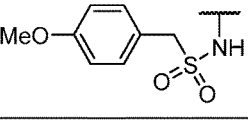 | M15 | methoxy-methyl | 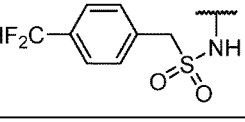 |
| M06 | methoxy-methyl | 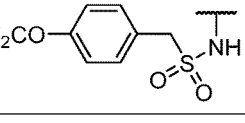 | M16 | methoxy-methyl | 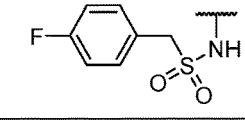 |
| M07 | methoxy-methyl | 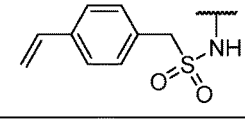 | M17 | methoxy-methyl | 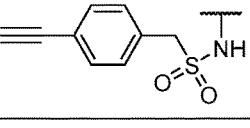 |
| | | | M18 | methoxy-methyl | 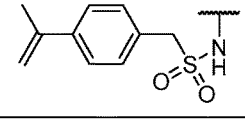 |

| ID | R¹ | ![structure] |
|----|----|----|
| M19 | methoxy-methyl |  |
| M20 | methoxy-methyl |  |
| M21 | methoxy-methyl |  |
| M22 | methoxy-methyl |  |
| M23 | methoxy-methyl |  |
| M24 | methoxy-methyl |  |
| M25 | methoxy-methyl |  |
| M26 | methoxy-methyl |  |
| M27 | methoxy-methyl |  |

| ID | R¹ | |
|----|----|----|
| M28 | methoxy-methyl |  |
| M29 | methoxy-methyl |  |
| M30 | methoxy-methyl |  |
| M31 | methoxy-methyl |  |
| M32 | methoxy-methyl |  |
| M33 | methoxy-methyl |  |
| M34 | methoxy-methyl |  |
| M35 | methoxy-methyl |  |
| M36 | methoxy-methyl |  |

Fig. 5FF

| ID | R¹ | |
|---|---|---|
| M37 | methoxy-methyl | 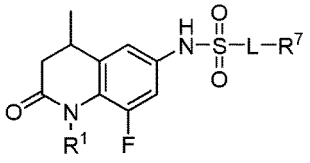 |
| M38 | methoxy-methyl | 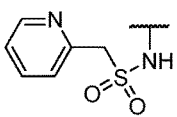 |
| M39 | methoxy-methyl | 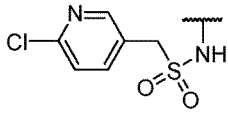 |
| M40 | methoxy-methyl | 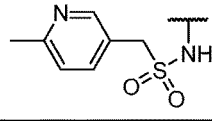 |
| M41 | methoxy-methyl | 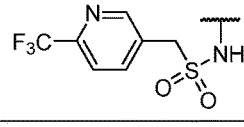 |
| M42 | methoxy-methyl | 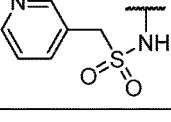 |
| M43 | methoxy-methyl | 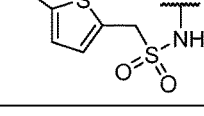 |
| M44 | methoxy-methyl | 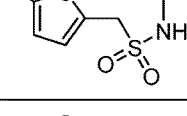 |
| M45 | methoxy-methyl | 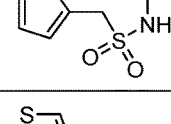 |
| M46 | methoxy-methyl | 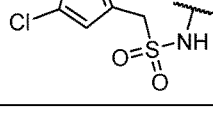 |

| ID | R¹ | |
|---|---|---|
| M47 | methoxy-methyl | 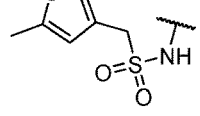 |
| N01 | cyclobutyl-methyl | 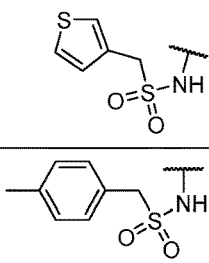 |
| N02 | cyclobutyl-methyl | 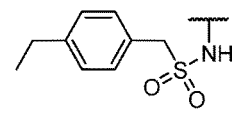 |
| N03 | cyclobutyl-methyl | 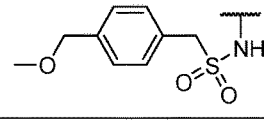 |
| N04 | cyclobutyl-methyl | 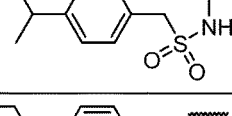 |
| N05 | cyclobutyl-methyl | 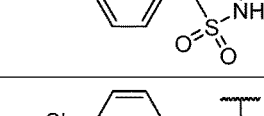 |
| N06 | cyclobutyl-methyl | 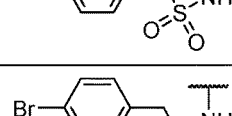 |
| N07 | cyclobutyl-methyl | 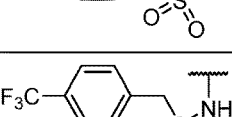 |
| N08 | cyclobutyl-methyl | 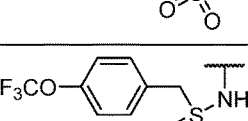 |
| N09 | cyclobutyl-methyl | 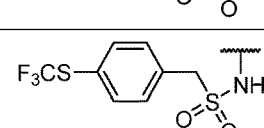 |
| N10 | cyclobutyl-methyl | 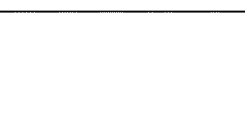 |

Fig. 5GG

| | | | | | |
|---|---|---|---|---|---|
| ID | R¹ | 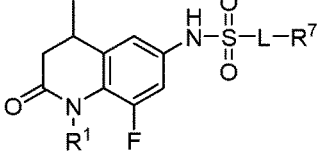 | ID | R¹ | |
| N11 | cyclobutyl-methyl | 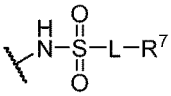 | N21 | cyclobutyl-methyl | 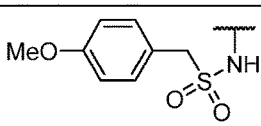 |
| N12 | cyclobutyl-methyl | 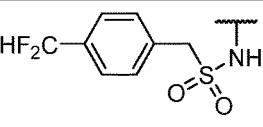 | N22 | cyclobutyl-methyl | 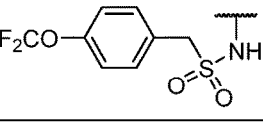 |
| N13 | cyclobutyl-methyl | 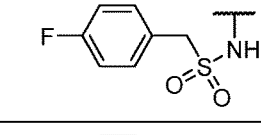 | N23 | cyclobutyl-methyl | 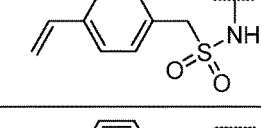 |
| N14 | cyclobutyl-methyl | 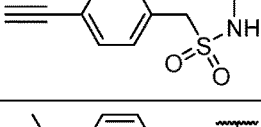 | N24 | cyclobutyl-methyl | 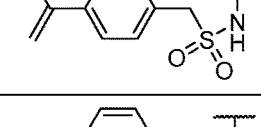 |
| N15 | cyclobutyl-methyl | 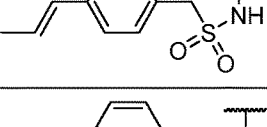 | N25 | cyclobutyl-methyl | 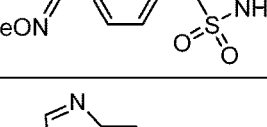 |
| N16 | cyclobutyl-methyl | 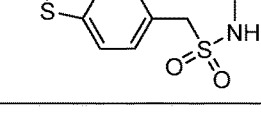 | N26 | cyclobutyl-methyl | 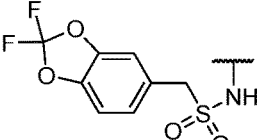 |
| N17 | cyclobutyl-methyl | 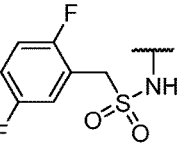 | N27 | cyclobutyl-methyl | 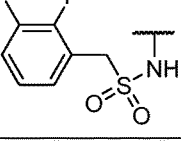 |
| N18 | cyclobutyl-methyl | 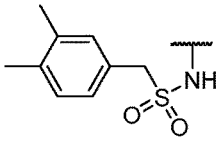 | N28 | cyclobutyl-methyl | 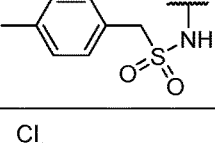 |
| N19 | cyclobutyl-methyl | 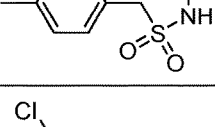 | | | |
| N20 | cyclobutyl-methyl | 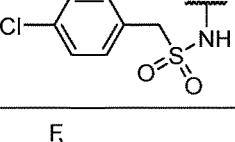 | | | |

Fig. 5HH

| | | | | | |
|---|---|---|---|---|---|
| 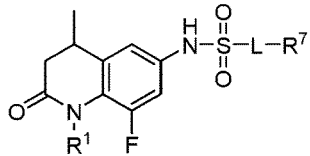 | | | | | |
| ID | R¹ | 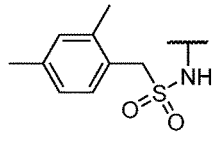 | ID | R¹ | |
| N29 | cyclobutyl-methyl | 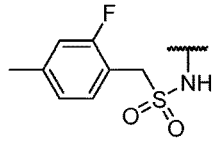 | N38 | cyclobutyl-methyl | 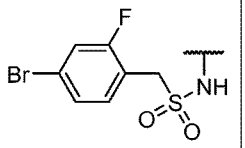 |
| N30 | cyclobutyl-methyl | 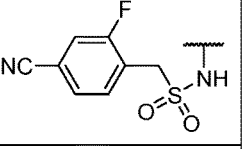 | N39 | cyclobutyl-methyl | 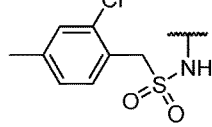 |
| N31 | cyclobutyl-methyl | 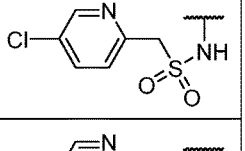 | N40 | cyclobutyl-methyl | 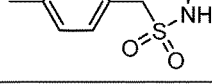 |
| N32 | cyclobutyl-methyl | 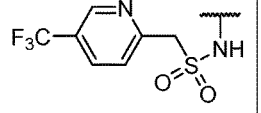 | N41 | cyclobutyl-methyl | 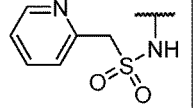 |
| N33 | cyclobutyl-methyl | 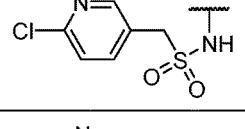 | N42 | cyclobutyl-methyl | 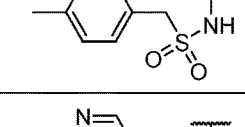 |
| N34 | cyclobutyl-methyl | 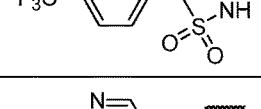 | N43 | cyclobutyl-methyl | 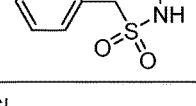 |
| N35 | cyclobutyl-methyl | 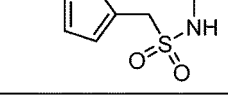 | N44 | cyclobutyl-methyl | 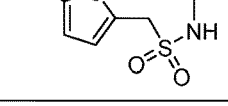 |
| N36 | cyclobutyl-methyl | 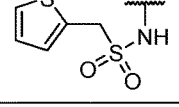 | N45 | cyclobutyl-methyl | 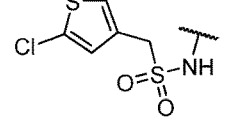 |
| N37 | cyclobutyl-methyl | 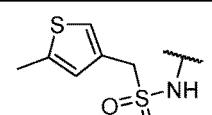 | N46 | cyclobutyl-methyl | 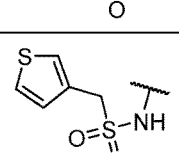 |
| | | | N47 | cyclobutyl-methyl | |

Fig. 5II

| ID | R¹ | ![structure] |
|---|---|---|
| O01 | 3-fluoropropyl | 4-methylphenyl-CH₂-S(=O)₂-NH- |
| O02 | 3-fluoropropyl | 4-ethylphenyl-CH₂-S(=O)₂-NH- |
| O03 | 3-fluoropropyl | 4-methoxymethylphenyl-CH₂-S(=O)₂-NH- |
| O04 | 3-fluoropropyl | 4-isopropylphenyl-CH₂-S(=O)₂-NH- |
| O05 | 3-fluoropropyl | 4-ethylphenyl-CH₂-S(=O)₂-NH- |
| O06 | 3-fluoropropyl | 4-chlorophenyl-CH₂-S(=O)₂-NH- |
| O07 | 3-fluoropropyl | 4-bromophenyl-CH₂-S(=O)₂-NH- |
| O08 | 3-fluoropropyl | 4-(F₃C)phenyl-CH₂-S(=O)₂-NH- |
| O09 | 3-fluoropropyl | 4-(F₃CO)phenyl-CH₂-S(=O)₂-NH- |
| O10 | 3-fluoropropyl | 4-(F₃CS)phenyl-CH₂-S(=O)₂-NH- |
| O11 | 3-fluoropropyl | 4-(MeO)phenyl-CH₂-S(=O)₂-NH- |
| O12 | 3-fluoropropyl | 4-(HF₂C)phenyl-CH₂-S(=O)₂-NH- |
| O13 | 3-fluoropropyl | 4-(HF₂CO)phenyl-CH₂-S(=O)₂-NH- |
| O14 | 3-fluoropropyl | 4-fluorophenyl-CH₂-S(=O)₂-NH- |
| O15 | 3-fluoropropyl | 4-vinylphenyl-CH₂-S(=O)₂-NH- |
| O16 | 3-fluoropropyl | 4-ethynylphenyl-CH₂-S(=O)₂-NH- |
| O17 | 3-fluoropropyl | 4-isopropenylphenyl-CH₂-S(=O)₂-NH- |
| O18 | 3-fluoropropyl | 4-propenylphenyl-CH₂-S(=O)₂-NH- |
| O19 | 3-fluoropropyl | 4-(MeON=CH)phenyl-CH₂-S(=O)₂-NH- |
| O20 | 3-fluoropropyl | benzothiazol-6-yl-CH₂-S(=O)₂-NH- |
| O21 | 3-fluoropropyl | 2,2-difluorobenzo[1,3]dioxol-5-yl-CH₂-S(=O)₂-NH- |

Fig. 5JJ

| ID | R¹ | ⟨NH-S(=O)₂-L-R⁷⟩ | ID | R¹ | |
|---|---|---|---|---|---|
| O22 | 3-fluoropropyl | 2,5-difluorobenzyl sulfonamide | O30 | 3-fluoropropyl | 2-fluoro-4-methylbenzyl sulfonamide |
| O23 | 3-fluoropropyl | 2,3-difluorobenzyl sulfonamide | O31 | 3-fluoropropyl | 4-bromo-2-fluorobenzyl sulfonamide |
| O24 | 3-fluoropropyl | 3,4-dimethylbenzyl sulfonamide | O32 | 3-fluoropropyl | 4-cyano-2-fluorobenzyl sulfonamide |
| O25 | 3-fluoropropyl | 3-fluoro-4-methylbenzyl sulfonamide | O33 | 3-fluoropropyl | 2-chloro-4-methylbenzyl sulfonamide |
| O26 | 3-fluoropropyl | 3-chloro-4-methylbenzyl sulfonamide | O34 | 3-fluoropropyl | (5-chloropyridin-2-yl)methyl sulfonamide |
| O27 | 3-fluoropropyl | 3,4-dichlorobenzyl sulfonamide | O35 | 3-fluoropropyl | (5-methylpyridin-2-yl)methyl sulfonamide |
| O28 | 3-fluoropropyl | 4-chloro-3-fluorobenzyl sulfonamide | O36 | 3-fluoropropyl | (5-trifluoromethylpyridin-2-yl)methyl sulfonamide |
| O29 | 3-fluoropropyl | 2,4-dimethylbenzyl sulfonamide | O37 | 3-fluoropropyl | (pyridin-2-yl)methyl sulfonamide |
| | | | O38 | 3-fluoropropyl | (6-chloropyridin-3-yl)methyl sulfonamide |

Fig. 5KK

| ID | R¹ | ![sulfonamide] |
|----|-----|----------------|
| O39 | 3-fluoropropyl | 6-methylpyridin-3-ylmethyl sulfonamide |
| O40 | 3-fluoropropyl | 6-(trifluoromethyl)pyridin-3-ylmethyl sulfonamide |
| O41 | 3-fluoropropyl | pyridin-3-ylmethyl sulfonamide |
| O42 | 3-fluoropropyl | 5-chlorothiophen-2-ylmethyl sulfonamide |
| O43 | 3-fluoropropyl | 5-methylthiophen-2-ylmethyl sulfonamide |
| O44 | 3-fluoropropyl | thiophen-2-ylmethyl sulfonamide |
| O45 | 3-fluoropropyl | 5-chlorothiophen-3-ylmethyl sulfonamide |
| O46 | 3-fluoropropyl | 5-methylthiophen-3-ylmethyl sulfonamide |
| O47 | 3-fluoropropyl | thiophen-3-ylmethyl sulfonamide |

Me = methyl.

DERIVATIVES OF HALO QUINABACTIN

CROSS-REFERENCE TO RELATED APPLICATIONS

This application claims the benefit under 35 USC 119(e) of U.S. Provisional Application No. 62/210,858, filed Aug. 27, 2015, and U.S. Provisional Application No. 62/291,726, filed Feb. 5, 2016, both of which are incorporated herein by reference in their entirety for all purposes.

FIELD OF THE INVENTION

The present invention relates to novel sulfonamide derivatives, to processes and intermediates for preparing them, to plant growth regulator compositions comprising them and to methods of using them for controlling the growth of plants, improving plant tolerance to abiotic stress (including environmental and chemical stresses), inhibiting seed germination and/or safening a plant against phytotoxic effects of chemicals.

BACKGROUND OF THE INVENTION

Abscisic acid (ABA) is a plant hormone that plays a major role in plant growth, development and response to abiotic stress. ABA causes many of its cellular responses by binding to a soluble family of receptors called PYR/PYL proteins, which contain a ligand-binding pocket for ABA and other agonists. Direct application of ABA to plants has been shown to improve their water use efficiency. However, ABA is difficult and expensive to prepare and itself unstable to environmental conditions and therefor unsuitable for large scale agricultural applications. It is therefore desirable to search for ABA agonists that may be useful for improving plant tolerance to environment stress such as drought, inhibit seed germination, regulate plant growth and improve crop yield.

Park et al. (2009, Science, vol. 324(5930), 1068-1071) reported that ABA agonist pyrabactin activates ABA responses in seeds, but does not trigger significant responses in vegetative tissues. Okamoto et al. (PNAS, 2013, 110(29), 12132-12137; and WO2013/148339) reported a new ABA agonist, quinabactin, which binds to the PYR/PRL receptor proteins and causes an abscisic acid response in vivo. Quinabactin has been shown to induce stomatal closure, suppress of water loss and promote drought tolerance.

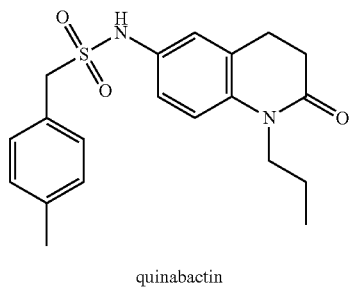

quinabactin

There is a need to identify improved agonists of abscisic acid for improving plant growth and development, and plant tolerance to environmental stresses. The present invention relates to novel analogs of quinabactin that have improved properties. Benefits of the compounds of the present invention include enhanced tolerance to abiotic stress, improved inhibition of seed germination, better regulation of crop growth, improved crop yield, and/or improved physical properties resulting in better plant uptake, water solubility, chemical stability or physical stability.

SUMMARY OF THE INVENTION

The present invention provides novel sulfonamide derivatives, processes and intermediates for preparing them, compositions comprising them and methods of using them.

In one aspect, the invention provides a compound of Formula (I):

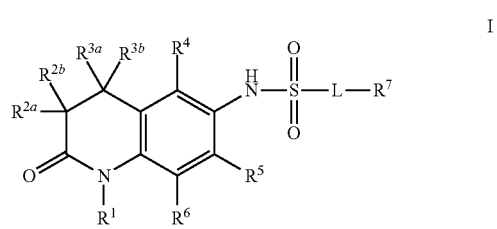

or salts or N-oxides thereof, and isomers, tautomers, enantiomers or diastereomers of these compounds. $R^1$ is selected from hydrogen, alkyl, cyano-alkyl, haloalkyl, alkoxy-alkyl, haloalkyl-alkyl, haloalkoxy-alkyl, cycloalkyl-alkyl, alkenyl, haloalkenyl, alkynyl, haloalkynyl, and heterocycloalkyl; or $R^1$ is selected from alkyl, alkyl-aryl, cycloalkyl, phenyl and heteroaryl, each optionally substituted with one to three $R^x$. Each $R^x$ is independently selected from halogen, cyano, hydroxy, alkyl, haloalkyl, alkoxy, haloalkoxy, alkylsulfanyl, haloalkylsulfanyl, alkylsulfinyl, haloalkylsulfinyl, alkylsulfonyl, haloalkylsulfonyl, cycloalkyl, and alkoxycarbonyl. $R^{2a}$, $R^{2b}$, $R^{3a}$, and $R^{3b}$ are independently selected from hydrogen, halogen, cyano, alkyl, alkenyl, alkynyl, alkoxy, haloalkyl, haloalkoxy and cycloalkyl. Two members selected from $R^{2a}$, $R^{2b}$, $R^{3a}$, and $R^{3b}$, together with the atom to which they are attached, are optionally joined to form a cycloalkyl. $R^4$, $R^5$, and $R^6$ are independently selected from hydrogen, halogen, cyano, alkyl, alkenyl, alkynyl, alkoxy, haloalkyl, haloalkoxy and cycloalkyl. At least one of $R^4$, $R^5$, and $R^6$ is selected from halogen, fluoromethyl, difluoromethyl, trifluoromethyl, cyclopropyl, cyano, and ethynyl. L is selected from alkyl, alkenyl, alkynyl, and alkoxy, each optionally substituted with one to three moieties independently selected from halogen, cyano, alkyl, and alkoxy; or L is a bond. $R^7$ is selected from aryl, heteroaryl, alkyl, cycloalkyl, and heterocycloalkyl, each optionally substituted with one to five $R^y$. Each $R^y$ is independently selected from halogen, cyano, nitro, alkyl, haloalkyl, alkoxy, haloalkoxy, alkylsulfanyl, haloalkylsulfanyl, alkylsulfinyl, haloalkylsulfinyl, alkylsulfonyl, haloalkylsulfonyl, alkenyl, haloalkenyl, alkynyl, haloalkynyl, cycloalkyl, alkoxy-alkyl, —COOH, —COOR$^9$, —CONHR$^9$, —CONR$^{9a}$R$^9$, —NHCOR$^9$, —CH=N—OH, —CH=N—OR$^9$, and —COR$^9$; wherein the alkyl, haloalkyl, alkoxy, haloalkoxy, alkylsulfanyl, haloalkylsulfanyl, alkylsulfinyl, haloalkylsulfinyl, alkylsulfonyl, haloalkylsulfonyl, alkenyl, haloalkenyl, alkynyl, haloalkynyl, cycloalkyl, and alkoxy-alkyl is optionally substituted with one to four $R^z$. $R^9$ and $R^{9a}$ are independently alkyl, each optionally substituted with one to four $R^z$. Each $R^z$ is independently selected from halogen, cyano, nitro, alkyl, haloalkyl, —OH, alkoxy, and haloalkoxy. Two $R^y$ moieties, together with the atom to which they are attached, are optionally joined to form a ring, which is optionally substituted with one to three $R^z$ moieties. When $R^7$ is phenyl, the phenyl is not substituted at the para position (relative to the attachment point to L) with $C_3$-$C_6$ cycloalkyl or substituted $C_3$-$C_6$ cycloalkyl.

In further aspects, the invention provides formulations of these compounds formulated appropriately for administration to plants and methods of using the compounds and formulations.

Other objects, advantages and aspects of the present invention will be apparent from the detailed description below.

BRIEF DESCRIPTION OF THE DRAWINGS

FIG. 1 is a table showing water use data for soybean plants after administration of one of several compounds of the invention or quinabactin at 500 μM.

FIG. 2 is a table showing water use data for soybean plants after administration of a compound of the invention or quinabactin at various concentrations.

FIG. 3 is a table showing water use data for corn plants after administration of a compound of the invention or quinabactin at 500 μM.

FIG. 4 is a table showing water use data for corn plants after administration of the indicated compounds at 500 μM for one day after application.

DETAILED DESCRIPTION OF THE INVENTION

Definitions

Figure 5A:
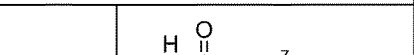
FIG. 5A-FIG. 5KK is a table showing exemplary compounds of the invention.

Before the invention is described in greater detail, it is to be understood that the invention is not limited to particular embodiments described herein as such embodiments may vary. It is also to be understood that the terminology used herein is for the purpose of describing particular embodiments only, and the terminology is not intended to be limiting. The scope of the invention will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number. All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features which may be readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

The following definitions are broadly applicable to each of the embodiments of the present invention set forth herein below. Unless defined otherwise, all technical and scientific terms used herein generally have the same meaning as commonly understood by one of ordinary skill in the art to which this invention belongs. Generally, the nomenclature used herein and the laboratory procedures in analytical chemistry, and organic synthesis are those well-known and commonly employed in the art. Standard techniques, or modifications thereof, are used for chemical syntheses and chemical analyses.

The term "alkyl," by itself or as part of another substituent, means, unless otherwise stated, a straight- or branched-chain, or cyclic hydrocarbon radical, or combination thereof, which is fully saturated and can include mono-, di-, tri- and tetra-valent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. The term "alkyl", as used herein refers to alkyl moieties, which can be mono-, di- or polyvalent species as appropriate to satisfy valence requirements.

The term "alkenyl," by itself or as part of another substituent, means, unless otherwise stated, a straight- or branched-chain, or cyclic alkyl radical, or combination thereof, having one or more carbon-carbon double bonds. Examples of alkenyl groups include, but are not limited to, vinyl, 2-propenyl, crotyl, isopenten-2-yl, butadien-2-yl, 2,4-pentadienyl, 1,4-pentadien-3-yl, and the higher homologs and isomers.

The term "alkynyl," by itself or as part of another substituent, means, unless otherwise stated, a straight- or branched-chain, or cyclic alkyl radical, or combination thereof, having one or more carbon-carbon triple bonds.

Examples of alkynyl groups include, but are not limited to, ethynyl, 1- and 3-propynyl, 3-butynyl, and the higher homologs and isomers.

The term "alkylene," by itself or as part of another substituent, means a divalent radical derived from an alkyl moiety, as exemplified, but not limited, by —CH$_2$CH$_2$CH$_2$CH$_2$— Typically, an alkyl (or alkylene) group will have from 1 to 24 carbon atoms, with those groups having 10 or fewer carbon atoms being preferred in the present invention. For alkylene and heteroalkylene linker groups, it is optional that no orientation of the linker group is implied by the direction in which the formula of the linker group is written. For example, the formula —C(O)$_2$R'— represents —C(O)$_2$R'— and, optionally, —R'C(O)$_2$—. A "lower alkyl" or "lower alkylene" is a shorter chain alkyl or alkylene group, generally having eight, seven, six, five or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight- or branched-chain, or cyclic alkyl radical consisting of the stated number of carbon atoms and at least one heteroatom selected from the group consisting of B, O, N, Si and S, wherein the heteroatom may optionally be oxidized and the nitrogen atom may optionally be quaternized. The heteroatom(s) may be placed at any internal position of the heteroalkyl group or at a terminus, e.g., the position through which the alkyl group is attached to the remainder of the molecule. Examples of "heteroalkyl" groups include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —Si(CH$_3$)$_3$, and —CH$_2$—CH=N—OCH$_3$. Two or more heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent refers to a divalent heteroalkyl radical, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the termini (e.g., alkyleneoxy, alkylenedioxy, alkyleneamino, alkylenediamino, and the like).

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, cycloheptyl, and the like. Examples of heterocycloalkyl include, but are not limited to, 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

In some embodiments, any of the alkyl, alkenyl, alkynyl, alkylene, heteroalkylene, alkoxy, alkylamino, alkylthio, heteroalkyl, cycloalkyl and heterocycloalkyl groups is optionally substituted, e.g., with one or more groups referred to herein as an "alkyl group substituent."

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is meant to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic substituent that can be a single ring or multiple rings (preferably from 1 to 3 rings), which are fused together. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. In some embodiments, any of the aryl and heteroaryl groups is optionally substituted, e.g., with one or more groups referred to herein as an "aryl group substituent."

The term "arylalkyl" includes those radicals in which an aryl group is attached to an alkyl group (e.g., benzyl, phenethyl, and the like).

Substituents for the alkyl and heteroalkyl radicals as well as those groups often referred to as alkylene, heteroalkylene, alkenyl, heteroalkenyl, alkynyl, cycloalkyl, heterocycloalkyl, cycloalkenyl, and heterocycloalkenyl are generically referred to as "alkyl group substituents," and they can be one or more of a variety of groups selected from, but not limited to: —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR"R", —NRSO$_2$R', —CN and —NO$_2$ in a number ranging from zero to (2m'+1), where m' is the total number of carbon atoms in such radical. R', R", R"' and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "substituted alkyl" includes groups with carbon atoms bound to groups other than hydrogen, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." Exemplary substituents are selected from the list of alkyl group substituents and others, for example: halogen, —OR', =O, =NR', =N—OR', —NR'R", —SR', —SiR'R"R'", —OC(O)
R', —C(O)R', —CO$_2$R', —CONR'R", —OC(O)NR'R",
—NR"C(O)R', —NR'—C(O)NR"R'", —NR"C(O)$_2$R',
—NR—C(NR'R"R'")=NR"", —NR—C(NR'R")=NR'",
—S(O)R', —S(O)$_2$R', —S(O)$_2$NR'R", —NRSO$_2$R', —CN
and —NO$_2$, —R', —N$_3$, —CH(Ph)$_2$, fluoro(C$_1$-C$_4$)alkoxy,
and fluoro(C$_1$-C$_4$)alkyl, in a number ranging from zero to the
total number of open valences on the aromatic ring system;
and where R', R", R'" and R"" are preferably independently
selected from hydrogen, substituted or unsubstituted alkyl,
substituted or unsubstituted heteroalkyl, substituted or
unsubstituted aryl and substituted or unsubstituted heteroaryl. When a compound of the invention includes more than one R group, for example, each of the R groups is independently selected as are each R', R", R'" and R"" groups when more than one of these groups is present.

Two of the substituents on an aryl or heteroaryl ring, together with the atom to which they are attached, may optionally be joined to form a ring (e.g., a cycloalkyl or heterocycloalkyl ring) that is fused to the aryl or heteroaryl ring.

Two of the substituents on adjacent atoms of the aryl or heteroaryl ring may optionally be replaced with a substituent of the formula -T-C(O)—(CRR')$_q$-U-, wherein T and U are independently —NR—, —O—, —CRR'— or a single bond, and q is an integer from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_{16}$)alkyl.

As used herein, the term "heteroatom" includes oxygen (O), nitrogen (N), sulfur (S) and silicon (Si).

The symbol "R" is a general abbreviation that represents a substituent group that is selected from H, substituted or unsubstituted alkyl, substituted or unsubstituted heteroalkyl, substituted or unsubstituted aryl, substituted or unsubstituted heteroaryl, and substituted or unsubstituted heterocyclyl groups. R can also refer to alkyl group substituents and aryl group substituents.

The term "salt(s)" includes salts of the compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids, and the like, as well as the salts derived from relatively nontoxic organic acids like acetic, propionic, isobutyric, butyric, maleic, malic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate, and the like, and salts of organic acids like glucuronic or galactunoric acids and the like (see, for example, Berge et al., *Journal of Pharmaceutical Science*, 66: 1-19 (1977)). Certain specific compounds of the present invention contain both basic and acidic functionalities that allow the compounds to be converted into either base or acid addition salts. Hydrates of the salts are also included.

The symbol ⌇, displayed perpendicular to a bond, indicates the point at which the displayed moiety is attached to the remainder of the molecule.

The compounds herein described may have one or more asymmetric centers or planes. Compounds of the present invention containing an asymmetrically substituted atom may be isolated in optically active or racemic forms. It is well known in the art how to prepare optically active forms, such as by resolution of racemic forms (racemates), by asymmetric synthesis, or by synthesis from optically active starting materials. Resolution of the racemates can be accomplished, for example, by conventional methods such as crystallization in the presence of a resolving agent, or chromatography, using, for example a chiral HPLC column. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral (enantiomeric and diastereomeric), and racemic forms, as well as all geometric isomeric forms of a structure are intended, unless the specific stereochemistry or isomeric form is specifically indicated.

The graphic representations of racemic, ambiscalemic and scalemic or enantiomerically pure compounds used herein are taken from Maehr, *J. Chem. Ed.*, 62: 114-120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but not implying any absolute stereochemistry; and wedge outlines and dotted or broken lines denote enantiomerically pure compounds of indeterminate absolute configuration.

The term "charged group" refers to a group that bears a negative charge or a positive charge. The negative charge or positive charge can have a charge number that is an integer selected from 1, 2, 3 or higher or that is a fractional number. Exemplary charged groups include for example —OPO$_3^{2-}$, —OPO$_2^-$, —P$^+$Ph$_3$, —N$^+$R'R"R'", —S$^+$R and —C(O)O$^-$. It is understood that charged groups are accompanied by counterions of opposite charge, whether or not such counterions are expressly represented in the formulae provided herein.

The compounds herein described may have one or more charged groups. For example, the compounds may be zwitterionic, but may be neutral overall. Other embodiments may have one or more charged groups, depending on the pH and other factors. In these embodiments, the compound may be associated with a suitable counter-ion. It is well known in the art how to prepare salts or exchange counter-ions. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Counter-ions may be changed, for example, by ion-exchange techniques such as ion-exchange chromatography. All zwitterions, salts and counter-ions are intended, unless the counter-ion or salt is specifically indicated.

In some embodiments, the definition of terms used herein is according to IUPAC.

According to the present invention, "regulating or improving the growth of a crop" means an improvement in plant vigour, an improvement in plant quality, improved tolerance to stress factors, and/or improved input use efficiency.

An 'improvement in plant vigour' means that certain traits are improved qualitatively or quantitatively when compared with the same trait in a control plant which has been grown under the same conditions in the absence of the method of the invention. Such traits include, but are not limited to, early and/or improved germination, improved emergence, the ability to use less seeds, increased root growth, a more developed root system, increased root nodulation, increased shoot growth, increased tillering, stronger tillers, more productive tillers, increased or improved plant stand, less plant verse (lodging), an increase and/or improvement in plant height, an increase in plant weight (fresh or dry), bigger leaf blades, greener leaf colour, increased pigment content, increased photosynthetic activity, earlier flowering, longer panicles, early grain maturity, increased seed, fruit or pod size, increased pod or ear number, increased seed number per pod or ear, increased seed mass, enhanced seed filling, less dead basal leaves, delay of senescence, improved vitality of the plant, increased levels of amino acids in storage tissues and/or less inputs needed (e.g., less fertiliser, water and/or labour needed). A plant with improved vigour may have an increase in any of the aforementioned traits or any combination or two or more of the aforementioned traits.

An 'improvement in plant quality' means that certain traits are improved qualitatively or quantitatively when compared with the same trait in a control plant which has been grown under the same conditions in the absence of the method of the invention. Such traits include, but are not limited to, improved visual appearance of the plant, reduced ethylene (reduced production and/or inhibition of reception), improved quality of harvested material, e.g., seeds, fruits, leaves, vegetables (such improved quality may manifest as improved visual appearance of the harvested material), improved carbohydrate content (e.g., increased quantities of sugar and/or starch, improved sugar acid ratio, reduction of reducing sugars, increased rate of development of sugar), improved protein content, improved oil content and composition, improved nutritional value, reduction in anti-nutritional compounds, improved organoleptic properties (e.g., improved taste) and/or improved consumer health benefits (e.g., increased levels of vitamins and anti-oxidants)), improved post-harvest characteristics (e.g., enhanced shelf-life and/or storage stability, easier processability, easier extraction of compounds), more homogenous crop development (e.g., synchronised germination, flowering and/or fruiting of plants), and/or improved seed quality (e.g., for use in following seasons). A plant with improved quality may have an increase in any of the aforementioned traits or any combination or two or more of the aforementioned traits.

An 'improved tolerance to stress factors' means that certain traits are improved qualitatively or quantitatively when compared with the same trait in a control plant which has been grown under the same conditions in the absence of the method of the invention. Such traits include, but are not limited to, an increased tolerance and/or resistance to abiotic stress factors which cause sub-optimal growing conditions such as drought (e.g., any stress which leads to a lack of water content in plants, a lack of water uptake potential or a reduction in the water supply to plants), cold exposure, heat exposure, osmotic stress, UV stress, flooding, increased salinity (e.g., in the soil), increased mineral exposure, ozone exposure, high light exposure and/or limited availability of nutrients (e.g., nitrogen and/or phosphorus nutrients). A plant with improved tolerance to stress factors may have an increase in any of the aforementioned traits or any combination or two or more of the aforementioned traits. In the case of drought and nutrient stress, such improved tolerances may be due to, for example, more efficient uptake, use or retention of water and nutrients. In particular, the compounds or compositions of the present invention are useful to improve tolerance to drought stress.

An 'improved input use efficiency' means that the plants are able to grow more effectively using given levels of inputs compared to the grown of control plants which are grown under the same conditions in the absence of the method of the invention. In particular, the inputs include, but are not limited to fertiliser (such as nitrogen, phosphorous, potassium, micronutrients), light and water. A plant with improved input use efficiency may have an improved use of any of the aforementioned inputs or any combination of two or more of the aforementioned inputs.

The term "plants" refers to all physical parts of a plant, including seeds, seedlings, saplings, roots, tubers, stems, stalks, foliage, and fruits.

The term "locus" as used herein means fields in or on which plants are growing, or where seeds of cultivated plants are sown, or where seed will be placed into the soil. It includes soil, seeds, and seedlings, as well as established vegetation.

The term "plant propagation material" denotes all generative parts of a plant, for example seeds or vegetative parts of plants such as cuttings and tubers. It includes seeds in the strict sense, as well as roots, fruits, tubers, bulbs, rhizomes, and parts of plants.

Compounds

In one aspect, the invention provides a compound of Formula (I):

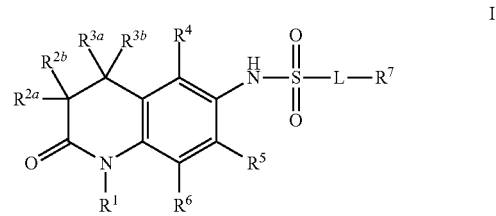

or salts or N-oxides thereof, and isomers, tautomers, enantiomers or diastereomers of these compounds. $R^1$, $R^{2a}$, $R^{2b}$, $R^{3a}$, $R^{3b}$, $R^4$, $R^5$, $R^6$, L, and $R^7$ are as defined herein. Any combination of $R^1$, $R^2$, $R^{2b}$, $R^{3a}$, $R^{3b}$, $R^4$, $R^5$, $R^6$, L, and $R^7$ is encompassed by this disclosure and specifically provided by the invention.

In some embodiments, $R^1$ is selected from hydrogen, alkyl, cyano-alkyl, haloalkyl, alkoxy-alkyl, haloalkyl-alkyl, haloalkoxy-alkyl, cycloalkyl-alkyl, alkenyl, haloalkenyl, alkynyl, haloalkynyl, and heterocycloalkyl. In some embodiments, $R^1$ is selected from hydrogen, $C_1$-$C_6$ alkyl, cyano-$C_1$-$C_6$ alkyl, $C_1$-$C_6$ haloalkyl, $C_1$-$C_3$ alkoxy-$C_1$-$C_6$ alkyl, $C_1$-$C_3$ haloalkyl-$C_1$-$C_6$ alkyl, $C_1$-$C_3$ haloalkoxy-$C_1$-$C_6$ alkyl, $C_3$-$C_4$ cycloalkyl-$C_1$-$C_3$ alkyl, $C_2$-$C_6$ alkenyl, $C_2$-$C_6$ haloalkenyl, $C_2$-$C_6$ alkynyl, $C_2$-$C_6$ haloalkynyl, and $C_4$-$C_5$ heterocycloalkyl. In some embodiments, $R^1$ is selected from hydrogen, $C_1$-$C_6$ alkyl, $C_1$-$C_6$ haloalkyl, $C_1$-$C_3$ alkoxy-$C_1$-$C_3$ alkyl, $C_1$-haloalkoxy-$C_1$-$C_3$ alkyl, $C_3$-$C_4$ cycloalkyl-$C_1$-$C_3$ alkyl, $C_2$-$C_6$ alkenyl and $C_2$-$C_6$ alkynyl. In some embodiments, $R^1$ is $C_1$-$C_6$ (i.e., $C_1$, $C_2$, $C_3$, $C_4$, $C_5$, or $C_6$) alkyl. In some embodiments, the alkyl group is linear or branched. In some embodiments, $R^1$ is $C_1$ alkyl (i.e., methyl). In some embodiments, $R^1$ is $C_2$ alkyl (i.e., ethyl). In some embodiments, $R^1$ is $C_3$ alkyl (i.e., n-propyl or iso-propyl). In some embodiments, $R^1$ is $C_4$ alkyl (i.e., n-butyl, sec-butyl, iso-butyl, or tert-butyl). In some embodiments, $R^1$ is selected from ethyl, n-propyl, and isopropyl. In some embodiments, $R^1$ is selected from ethyl and n-propyl. In some embodiments, $R^1$ is n-propyl. In some embodiments, $R^1$ is $C_3$-$C_4$ (i.e., $C_3$ or $C_4$) cycloalkyl. In some embodiments, $R^1$ is cyclopropyl. In some embodiments, $R^1$ is $C_2$-$C_6$ (i.e., $C_2$, $C_3$, $C_4$, $C_5$, or $C_6$) alkenyl. In some embodiments, $R^1$ is allyl (—$CH_2$—CH=$CH_2$). In some embodiments, $R^1$ is selected from alkyl, alkyl-aryl, cycloalkyl, phenyl and heteroaryl, each optionally substituted with one to three (i.e., one, two, or three) $R^x$. $R^x$ is as defined herein. In some embodiments, $R^1$ is selected from $C_1$-$C_4$ alkyl, $C_1$-$C_4$ alkyl-aryl, $C_3$-$C_5$ cycloalkyl, phenyl and 5- or 6-membered heteroaryl, each optionally substituted with one to three $R^x$. In some embodiments, $R^1$ is selected from $C_3$-$C_4$ cycloalkyl, phenyl and 5- or 6-membered heteroaryl, each optionally substituted with one to three $R^x$. In some embodiments, $R^1$ is selected from $C_3$-$C_4$ cycloalkyl and $C_2$-$C_6$ alkenyl; or $R^1$ is $C_1$-$C_4$ alkyl, optionally substituted with one to three $R^x$ moieties. In some embodiments, $R^1$ is linear or branched $C_1$-$C_4$ alkyl, optionally substituted with one to three $R^x$ moieties. In some embodiments, $R^1$ is selected from alkyl, cyano-alkyl, haloalkyl, hydroxyalkyl, alkoxy-alkyl, cycloalkyl-alkyl, alkoxy-carbonyl-alkyl, cycloalkyl, and alkenyl. In some embodiments, $R^1$ is selected from $C_1$-$C_8$ alkyl, cyano-$C_1$-$C_4$ alkyl, $C_1$-$C_4$ haloalkyl, $C_1$-$C_4$ hydroxyalkyl, $C_1$-$C_4$ alkoxy-$C_1$-$C_4$ alkyl, $C_3$-$C_4$ cycloalkyl-$C_1$-$C_4$ alkyl, ($C_1$-$C_3$ alkoxy)-carbonyl-$C_1$-$C_4$ alkyl, $C_3$-$C_4$ cycloalkyl, and $C_2$-$C_6$ alkenyl. In some embodiments, $R^1$ is selected from ethyl, isopropyl, n-propyl, allyl, cyclopropyl, cyclobutyl, 2,2,2-trifluoroethyl, 2-cyanoethyl, 2-methoxy-2-oxoethyl, cyclopropylmethyl, 2-methoxyethyl, 2,2-difluoroethyl, methoxymethyl, cyclobutylmethyl, and 3-fluoropropyl. In some embodiments, $R^1$ is selected from ethyl, isopropyl, n-propyl, allyl, and cyclopropyl.

In some embodiments, each $R^x$ is independently selected from halogen, cyano, hydroxy, alkyl, haloalkyl, alkoxy, haloalkoxy, alkylsulfanyl, haloalkylsulfanyl, alkylsulfinyl, haloalkylsulfinyl, alkylsulfonyl, haloalkylsulfonyl, cycloalkyl, and alkoxy-carbonyl. In some embodiments, each $R^x$ is independently selected from halogen, cyano, hydroxy, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylsulfanyl, $C_1$-$C_4$ haloalkylsulfanyl, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, $C_3$-$C_4$ cycloalkyl, and ($C_1$-$C_3$ alkoxy)-carbonyl. In some embodiments, each $R^x$ is independently selected from halogen, cyano, $C_1$-$C_3$ alkyl, $C_1$-$C_3$ haloalkyl, $C_1$-$C_3$ alkoxy, $C_1$-$C_3$ haloalkoxy and $C_3$-$C_4$ cycloalkyl. In some embodiments, each $R^x$ is independently selected from halogen, cyano, hydroxy, $C_1$-$C_4$ alkyl, $C_1$-$C_4$ alkoxy, $C_3$-$C_4$ cycloalkyl, and ($C_1$-$C_3$ alkoxy)-carbonyl.

In some embodiments, $R^{2a}$, $R^{2b}$, $R^{3a}$, and $R^{3b}$ are independently selected from hydrogen, halogen, cyano, alkyl, alkenyl, alkynyl, alkoxy, haloalkyl, haloalkoxy and cycloalkyl. In some embodiments, $R^{2a}$, $R^{2b}$, $R^{3a}$, and $R^{3b}$ are independently selected from hydrogen, halogen, cyano, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy and $C_3$-$C_4$ cycloalkyl. In some embodiments, $R^{2a}$, $R^{2b}$, $R^{3a}$, and $R^{3b}$ are independently selected from hydrogen, methyl, ethyl, and halogen. In some embodiments, $R^{2a}$, $R^{2b}$, and $R^{3b}$ are hydrogen; and $R^{3a}$ is selected from hydrogen and methyl. In some embodiments, $R^{2a}$, $R^{2b}$, $R^{3a}$, and $R^{3b}$ are hydrogen. In some embodiments, $R^{2a}$, $R^{2b}$, and $R^{3b}$ are hydrogen; and $R^{3a}$ is methyl. In some embodiments, two members selected from $R^{2a}$, $R^{2b}$, $R^{3a}$, and $R^{3b}$, together with the atom to which they are attached, are optionally joined to form a cycloalkyl. In some embodiments, two members selected from $R^{2a}$, $R^{2b}$, $R^{3a}$, and $R^{3b}$, together with the atom to which they are attached, are optionally joined to form a $C_3$-$C_4$ cycloalkyl. In some embodiments, two members selected from $R^{2a}$, $R^{2b}$, $R^{3a}$, and $R^{3b}$, together with the atom to which they are attached, are joined to form a cyclopropyl.

In some embodiments, $R^4$, $R^5$, and $R^6$ are independently selected from hydrogen, halogen, cyano, alkyl, alkenyl, alkynyl, alkoxy, haloalkyl, haloalkoxy and cycloalkyl. In some embodiments, $R^4$, $R^5$, and $R^6$ are independently selected from hydrogen, halogen, cyano, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy and $C_3$-$C_4$ cycloalkyl. In some embodiments, $R^4$, $R^5$, and $R^6$ are independently selected from hydrogen, halogen, fluoromethyl, difluoromethyl, trifluoromethyl, cyclopropyl, cyano, and ethynyl. In some embodiments, at least one of $R^4$, $R^5$, and $R^6$ is not hydrogen. In some embodiments, at least one of $R^4$, $R^5$, and $R^6$ is not hydrogen or $C_1$-$C_6$ alkyl. In some embodiments, at least one of $R^4$, $R^5$, and $R^6$ is not hydrogen or alkyl. In some embodiments, at least one of $R^4$, $R^5$, and $R^6$ is selected from halogen, fluoromethyl, difluoromethyl, trifluoromethyl, cyclopropyl, cyano, and ethynyl. In some embodiments, at least one of $R^4$, $R^5$, and $R^6$ is selected from halogen, difluoromethyl, trifluoromethyl, cyclopropyl, cyano, and ethynyl. In some embodiments, at least one of $R^4$, $R^5$, and $R^6$ is selected from fluoro, chloro, cyano, ethynyl, and trifluoromethyl. In some embodiments, at least one of $R^4$, $R^5$, and $R^6$ is halogen (i.e., fluoro, chloro, bromo, or iodo). In some embodiments, at least one of $R^4$, $R^5$, and $R^6$ is selected from fluoro and chloro. In some embodiments, at least one of $R^4$, $R^5$, and $R^6$ is fluoro. In some embodiments, $R^4$ and $R^5$ are hydrogen. In some embodiments, $R^6$ is selected from fluoro, chloro, cyano, ethynyl, and trifluoromethyl. In some embodiments, $R^6$ is fluoro. In some embodiments, $R^4$ and $R^5$ are hydrogen; and $R^6$ is selected from fluoro, chloro, cyano, ethynyl, and trifluoromethyl. In some embodiments, $R^4$ and $R^5$ are hydrogen; and $R^6$ is selected from fluoro and chloro. In some embodiments, $R^4$ and $R^5$ are hydrogen; and $R^6$ is fluoro. In some embodiments, $R^4$ and $R^5$ are hydrogen; and $R^6$ is chloro. In some embodiments, when $R^1$ is cyclopropylmethyl, and $R^{2a}$, $R^{2b}$, $R^{3a}$, $R^{3b}$, $R^4$ and $R^5$ are hydrogen, $R^6$ is not fluoro. In some embodiments, when $R^1$ is cyclopropylmethyl, and $R^{2a}$, $R^{2b}$, $R^{3a}$, $R^{3b}$, $R^4$ and $R^6$ are hydrogen, $R^5$ is not fluoro. In some embodiments, when $R^1$ is cyclopropylmethyl, and $R^{2a}$, $R^{2b}$, $R^{3a}$, $R^{3b}$ and $R^6$ are hydrogen, $R^4$ and $R^5$ are not fluoro. In some embodiments, (a) when $R^1$ is cyclopropylmethyl, and $R^{2a}$, $R^{2b}$, $R^{3a}$, $R^{3b}$, $R^4$ and $R^5$ are hydrogen, $R^6$ is not fluoro; (b) when $R^1$ is cyclopropylmethyl, and $R^{2a}$, $R^{2b}$, $R^{3a}$, $R^{3b}$, $R^4$ and $R^6$ are hydrogen, $R^5$ is not fluoro; and (c) when $R^1$ is cyclopropylmethyl, and $R^{2a}$, $R^{2b}$, $R^{3a}$, $R^{3b}$ and $R^6$ are hydrogen, $R^4$ and $R^5$ are not fluoro.

In some embodiments, L is selected from alkyl, alkenyl, alkynyl, and alkoxy, each optionally substituted with one to three moieties independently selected from halogen, cyano, alkyl, and alkoxy. In some embodiments, L is selected from $C_1$-$C_4$ alkyl and $C_2$-$C_4$ alkenyl, each optionally substituted with one to three moieties independently selected from halogen, cyano, $C_1$-$C_4$ alkyl, and $C_1$-$C_4$ alkoxy. In some embodiments, L is $C_1$-$C_2$ alkyl optionally substituted with one or two moieties independently selected from halogen, cyano and $C_1$-$C_2$ alkyl. In some embodiments, L is $C_1$-$C_2$ alkyl. In some embodiments, L is —$CH_2$—. In some embodiments, L is a bond.

In some embodiments, $R^7$ is selected from aryl, heteroaryl, alkyl, cycloalkyl, and heterocycloalkyl, each optionally substituted with one to five (i.e., one, two, three, four, or five) $R^y$ moieties. $R^y$ is defined herein. In some embodiments, $R^7$ is selected from aryl and heteroaryl, each optionally substituted with one to five (e.g., one to three) $R^y$ moieties. In some embodiments, $R^7$ is selected from phenyl and 5-, 6-, 9-, or 10-membered heteroaryl, each optionally substituted with one to three $R^y$. In some embodiments, $R^7$ is selected from phenyl, thienyl (such as 2- and 3-thienyl), pyridyl (such as 2-, 3-, and 4-pyridyl) and benzo[d]thiazolyl (such as benzo[d]thiazol-5-yl), each optionally substituted with one to three $R^y$. In some embodiments, $R^7$ is selected from phenyl, thienyl and pyridyl, each optionally substituted with one or two moieties selected from methyl, ethyl, fluoro, chloro, bromo, cyano, trifluoromethyl, trifluoromethoxy, methoxymethyl, methoxycarbonyl, and nitro. In some embodiments, $R^7$ is phenyl, optionally substituted with one or two moieties selected from methyl, ethyl, fluoro, chloro, bromo, cyano, trifluoromethyl, trifluoromethoxy, methoxymethyl, methoxycarbonyl, and nitro. In some embodiments, $R^7$ is phenyl, optionally substituted with one or two moieties selected from methyl, ethyl, fluoro, chloro, bromo, trifluoromethyl, trifluoromethoxy, methoxymethyl, methoxycarbonyl, and nitro. In some embodiments, $R^7$ is selected from phenyl, thienyl and pyridyl, each optionally substituted with one or two moieties selected from methyl, fluoro, chloro, bromo, cyano, trifluoromethyl, trifluoromethoxy, methoxycarbonyl, and nitro. In some embodiments, $R^7$ is phenyl, optionally substituted with one or two moieties selected from methyl, fluoro, chloro, bromo, cyano, trifluoromethyl, trifluoromethoxy, methoxycarbonyl, and nitro. In some embodiments, $R^7$ is phenyl substituted with one or two moieties selected from $C_1$-$C_4$ alkyl and halogen. In some embodiments, $R^7$ is phenyl substituted with one or two moieties selected from methyl, ethyl, and fluoro. In some embodiments, $R^7$ is

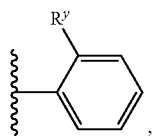, wherein $R^y$ is as defined herein. In some embodiments, $R^7$ is

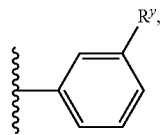

wherein $R^y$ is as defined herein. In some embodiments, $R^7$ is

wherein $R^y$ is as defined herein. In some embodiments, $R^7$ is

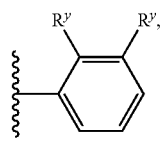

wherein each $R^y$ is independently as defined herein. In some embodiments, $R^7$ is

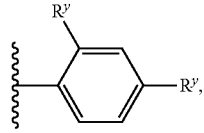

wherein each $R^y$ is independently as defined herein. In some embodiments, $R^7$ is

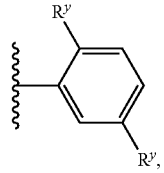

wherein each $R^y$ is independently as defined herein. In some embodiments, $R^7$ is

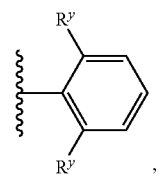, wherein each $R^y$ is independently as defined herein. In some embodiments, $R^7$ is

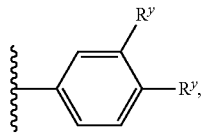

wherein each $R^y$ is independently as defined herein. In some embodiments, $R^7$ is

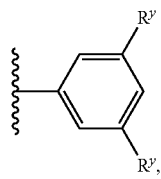

wherein each $R^y$ is independently as defined herein. In some embodiments, $R^7$ is

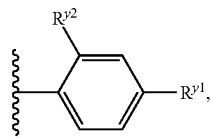

wherein $R^{y1}$ is $C_1$-$C_4$ alkyl, and $R^{y2}$ is hydrogen or halogen. In some embodiments, $R^7$ is

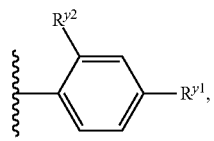

wherein $R^{y1}$ is methyl or ethyl, and $R^{y2}$ is hydrogen or fluoro. In some embodiments, $R^7$ is p-tolyl. In some embodiments, when $R^7$ is phenyl, the phenyl is not substituted at the para position (relative to the attachment point to L) with $C_3$-$C_6$ cycloalkyl or substituted $C_3$-$C_6$ cycloalkyl. In some embodiments, when $R^7$ is phenyl, the phenyl is not substituted at the para position (relative to the attachment point to L) with cycloalkyl or substituted cycloalkyl. In some embodiments, when $R^7$ is phenyl substituted with one to five $R^y$, none of the $R^y$ is a $C_3$-$C_6$ cycloalkyl or substituted $C_3$-$C_6$ cycloalkyl. In some embodiments, when $R^7$ is phenyl substituted with one to five $R^y$, none of the $R^y$ is a cycloalkyl or substituted cycloalkyl.

In some embodiments, each $R^y$ is independently selected from halogen, cyano, nitro, alkyl, haloalkyl, alkoxy, haloalkoxy, alkylsulfanyl, haloalkylsulfanyl, alkylsulfinyl, haloalkylsulfinyl, alkylsulfonyl, haloalkylsulfonyl, alkenyl, haloalkenyl, alkynyl, haloalkynyl, cycloalkyl, alkoxy-alkyl, —COOH, —COOR$^9$, —CONHR$^9$, —CONR$^{9a}$R$^9$, —NHCOR$^9$, —CH=N—OH, —CH=N—OR$^9$, and —COR$^9$; wherein the alkyl, haloalkyl, alkoxy, haloalkoxy, alkylsulfanyl, haloalkylsulfanyl, alkylsulfinyl, haloalkylsulfinyl, alkylsulfonyl, haloalkylsulfonyl, alkenyl, haloalkenyl, alky-nyl, haloalkynyl, cycloalkyl, and alkoxy-alkyl is optionally substituted with one to four (i.e., one, two, three, or four) $R^z$ moieties. $R^9$, $R^{9a}$, and $R^z$ are as defined herein. In some embodiments, each $R^y$ is independently selected from halogen, cyano, nitro, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylsulfanyl, $C_1$-$C_4$ haloalkylsulfanyl, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, $C_1$-$C_4$ alkoxy-$C_1$-$C_4$ alkyl, —COOH, —COOR$^9$, —CONHR$^9$, —CONR$^{9a}$R$^9$, —NHCOR$^9$, —CH=N—OH, —CH=N—OR$^9$, and —COR$^9$; wherein the $C_1$-$C_4$ alkyl, $C_1$-$C_4$ haloalkyl, $C_1$-$C_4$ alkoxy, $C_1$-$C_4$ haloalkoxy, $C_1$-$C_4$ alkylsulfanyl, $C_1$-$C_4$ haloalkylsulfanyl, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and $C_1$-$C_4$ alkoxy-$C_1$-$C_4$ alkyl is optionally substituted with one to four $R^z$. In some embodiments, each $R^y$ is independently selected from halogen, cyano, nitro, $C_1$-$C_4$ alkyl, $C_1$-$C_4$ haloalkyl, $C_1$-$C_4$ haloalkoxy, $C_1$-$C_4$ alkoxy-$C_1$-$C_4$ alkyl, and COOR$^9$. In some embodiments, each $R^y$ is independently selected from halogen, nitro, $C_1$-$C_4$ alkyl, $C_1$-$C_4$ haloalkyl, $C_1$-$C_4$ haloalkoxy, $C_1$-$C_4$ alkoxy-$C_1$-$C_4$ alkyl, and COOR$^9$. In some embodiments, each $R^y$ is independently selected from halogen, cyano, nitro, $C_1$-$C_4$ alkyl, $C_1$-$C_4$ haloalkyl, $C_1$-$C_4$ haloalkoxy, and COOR$^9$. In some embodiments, each $R^y$ is independently selected from methyl, ethyl, fluoro, chloro, bromo, cyano, trifluoromethyl, trifluoromethoxy, methoxymethyl, methoxycarbonyl, and nitro. In some embodiments, each $R^y$ is independently selected from methyl, ethyl, fluoro, chloro, bromo, trifluoromethyl, trifluoromethoxy, methoxymethyl, methoxycarbonyl, and nitro. In some embodiments, each $R^y$ is independently selected from halogen and $C_1$-$C_4$ alkyl. In some embodiments, each $R^y$ is independently selected from fluoro, methyl, and ethyl. In some embodiments, each $R^y$ is independently selected from halogen, cyano, $C_1$-$C_4$ alkyl, $C_1$-$C_4$ haloalkyl, $C_1$-$C_4$ alkoxy, $C_1$-$C_4$ haloalkoxy, $C_1$-$C_4$ haloalkylsulfanyl, $C_2$-$C_6$ alkenyl, $C_2$-$C_6$ alkynyl, $C_1$-$C_4$ alkoxy-$C_1$-$C_4$ alkyl, and —CH=N—OR$^9$; wherein the $C_1$-$C_4$ alkyl is optionally substituted with one to four $R^z$ moieties. In some embodiments, $R^y$ is not cyano. In some embodiments, two $R^y$ moieties, together with the atom to which they are attached, are optionally joined to form a ring (e.g, a carbocycle or heterocycle), which is optionally substituted with one to three $R^z$ moieties. In some embodiments, two $R^y$ moieties, together with the atom to which they are attached, are optionally joined to form a ring selected from a 4-, 5- or 6-membered carbocycle and a 4-, 5- or 6-membered heterocycle, each optionally substituted with one to three $R^z$ moieties. In some embodiments, two $R^y$ moieties, together with the atom to which they are attached, are optionally joined to form a 5-membered heterocycle, which is optionally substituted with one to three $R^z$ moieties.

In some embodiments, $R^9$ and $R^{9a}$ are independently alkyl, each optionally substituted with one to four $R^z$ moieties. $R^z$ is defined herein. In some embodiments, $R^9$ and $R^{9a}$ are independently $C_1$-$C_4$ alkyl, each optionally substituted with one to four $R^z$ moieties.

In some embodiments, $R^9$ is $C_1$-$C_4$ alkyl.

In some embodiments, each $R^z$ is independently selected from halogen, cyano, nitro, alkyl, haloalkyl, —OH, alkoxy, and haloalkoxy. In some embodiments, each $R^z$ is independently selected from halogen, cyano, nitro, $C_1$-$C_4$ alkyl, $C_1$-$C_4$ haloalkyl, —OH, $C_1$-$C_4$ alkoxy, and $C_1$-$C_4$ haloalkoxy. In some embodiments, each $R^z$ is independently selected from halogen and $C_1$-$C_4$ alkyl.
In some embodiments, the
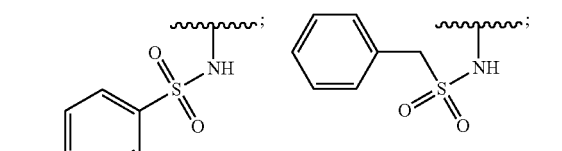
moiety is a member selected from:
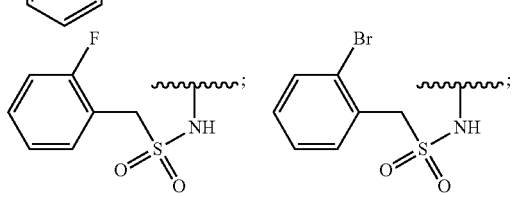
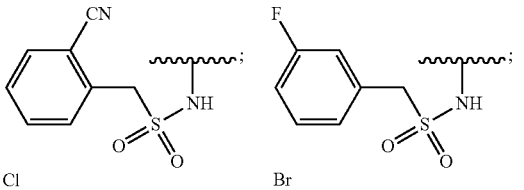
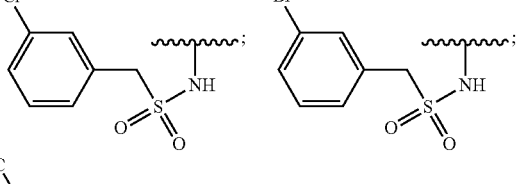
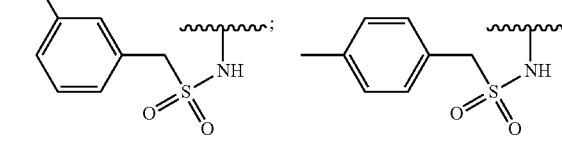
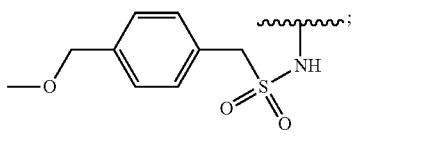
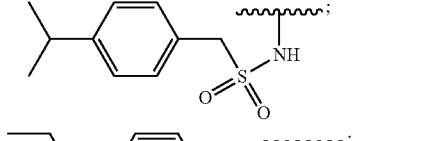
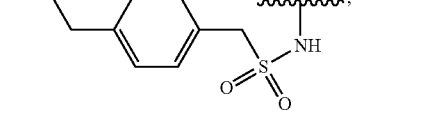
-continued
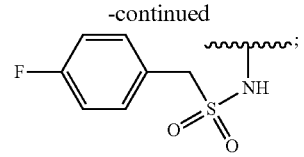
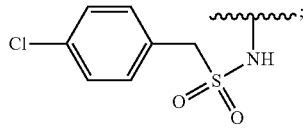
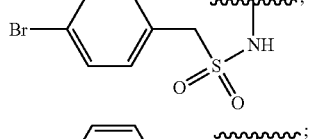
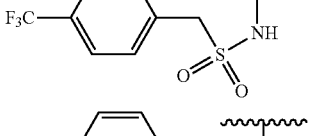
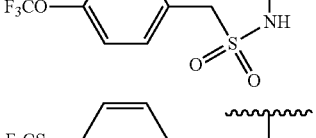
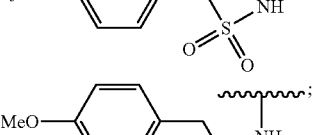
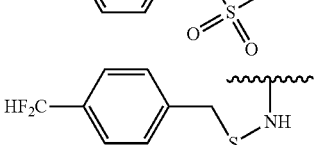
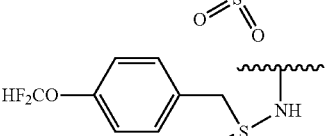
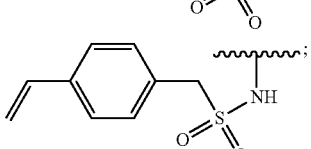
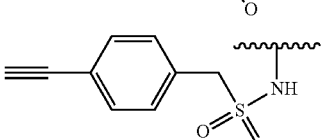
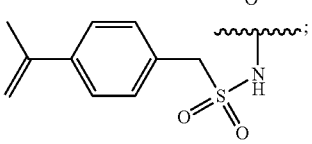
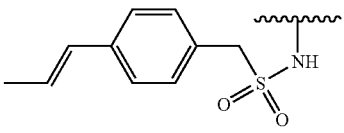

-continued
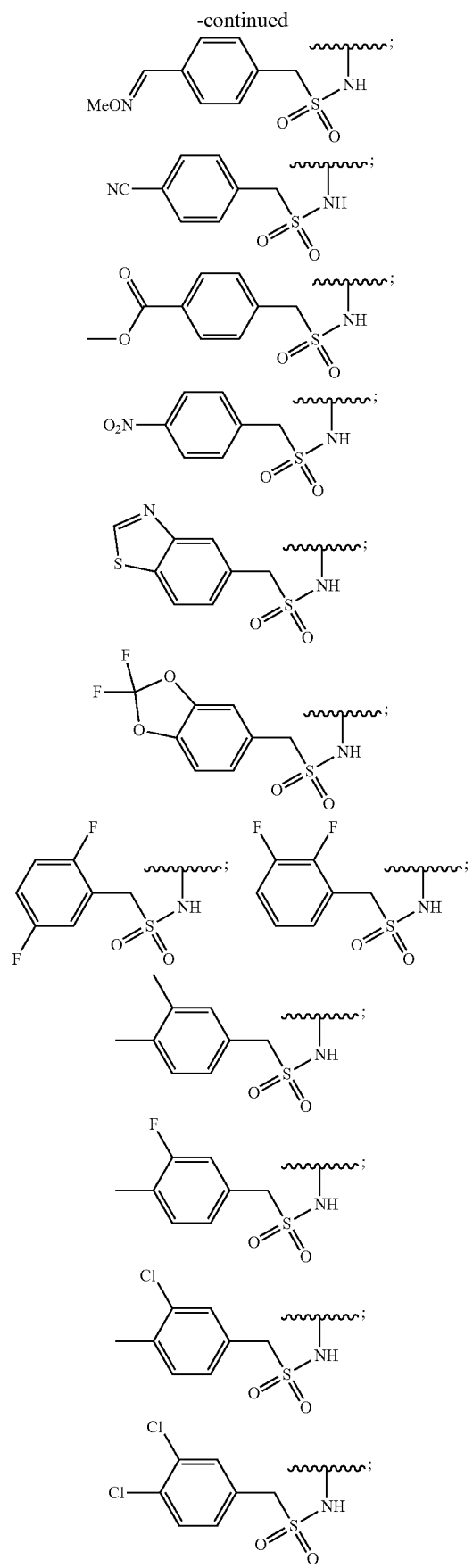
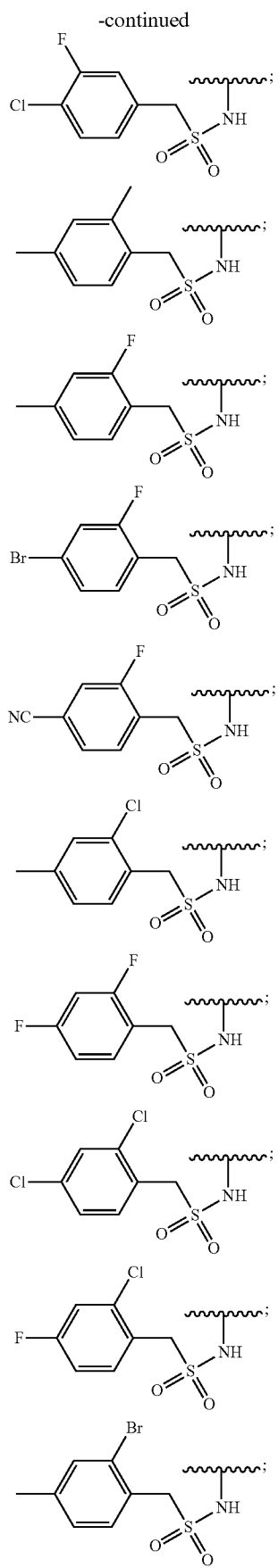

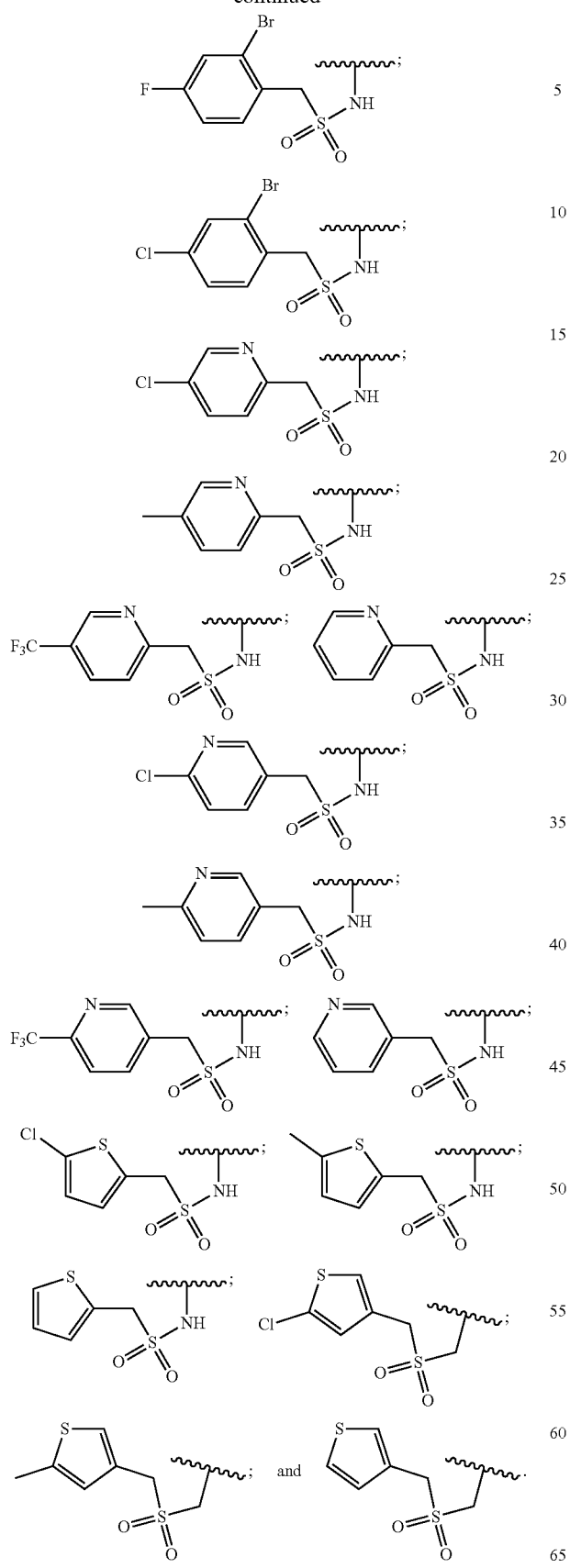
In some embodiments, the
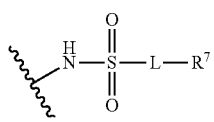
moiety is a member selected from:
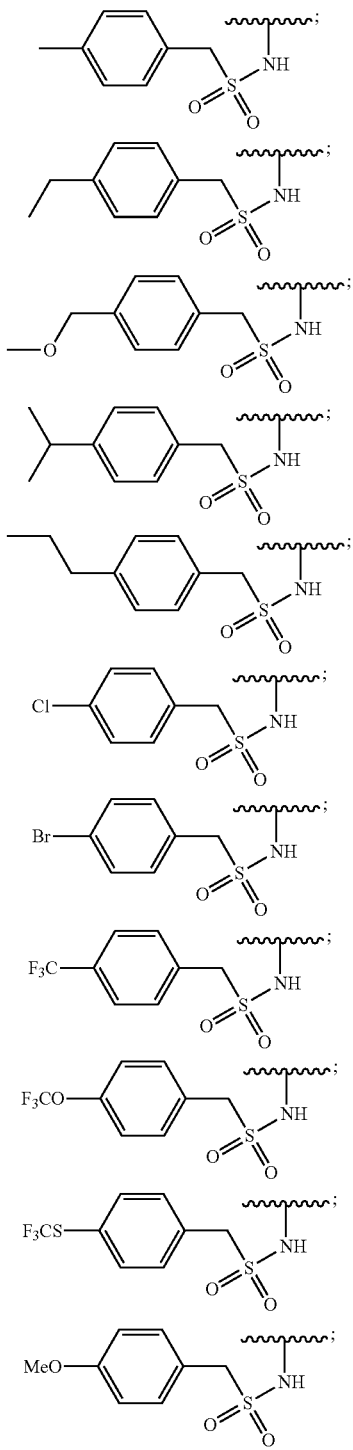

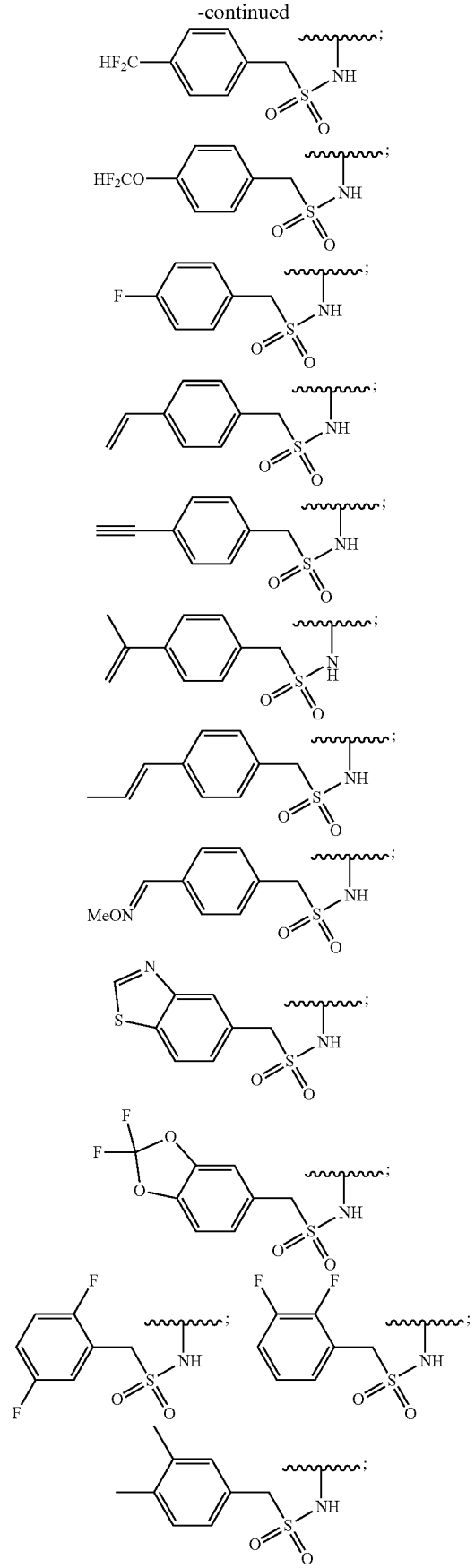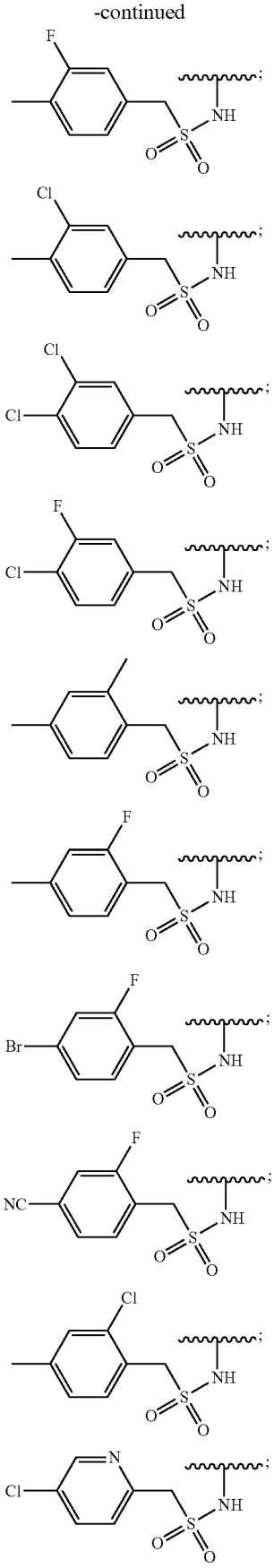

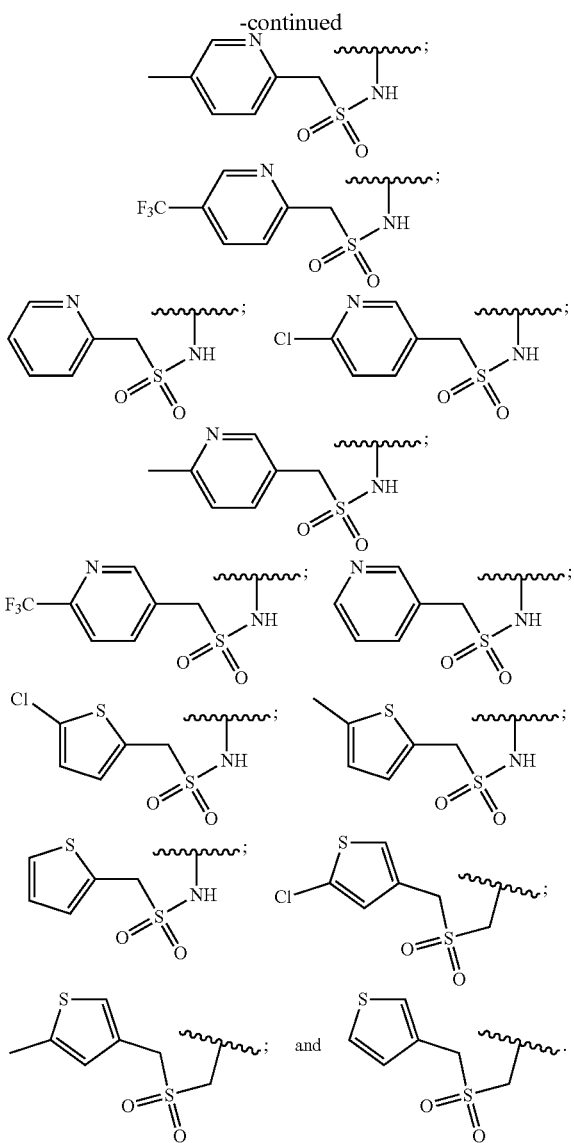

In some embodiments, the

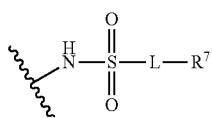

moiety is a member selected from:

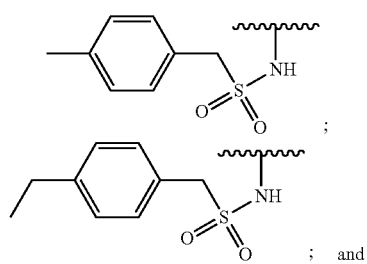

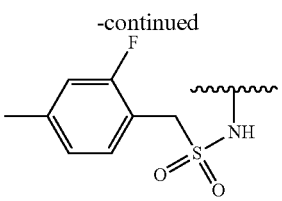

In some embodiments, the invention provides a compound of Formula (I):

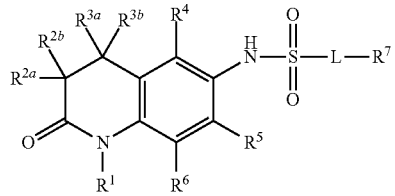

wherein $R^1$ is selected from hydrogen, $C_1$-$C_6$ alkyl, cyano-$C_1$-$C_6$ alkyl, $C_1$-$C_6$ haloalkyl, $C_1$-$C_3$ alkoxy-$C_1$-$C_6$ alkyl, $C_1$-$C_3$ haloalkyl-$C_1$-$C_6$ alkyl, $C_1$-$C_3$ haloalkoxy-$C_1$-$C_6$ alkyl, $C_3$-$C_4$ cycloalkyl-$C_1$-$C_3$ alkyl, $C_2$-$C_6$ alkenyl, $C_2$-$C_6$ haloalkenyl, $C_2$-$C_6$ alkynyl, $C_2$-$C_6$ haloalkynyl, and $C_4$-$C_5$ heterocycloalkyl; or $R^1$ is selected from $C_1$-$C_4$ alkyl, $C_1$-$C_4$ alkyl-aryl, $C_3$-$C_5$ cycloalkyl, phenyl and 5- or 6-membered heteroaryl, each optionally substituted with one to three $R^x$ moieties; each $R^x$ is independently selected from halogen, cyano, hydroxy, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylsulfanyl, $C_1$-$C_4$ haloalkylsulfanyl, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, $C_3$-$C_4$ cycloalkyl, and ($C_1$-$C_3$ alkoxy)-carbonyl; $R^{2a}$, $R^{2b}$, $R^{3a}$, and $R^{3b}$ are independently selected from hydrogen, halogen, cyano, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy and $C_3$-$C_4$ cycloalkyl; or two members selected from $R^{2a}$, $R^{2b}$, $R^{3a}$, and $R^{3b}$, together with the atom to which they are attached, are optionally joined to form a $C_3$-$C_4$ cycloalkyl; $R^4$, $R^5$, and $R^6$ are independently selected from hydrogen, halogen, cyano, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy and $C_3$-$C_4$ cycloalkyl; wherein at least one of $R^4$, $R^5$, and $R^6$ is independently selected from halogen, difluoromethyl, trifluoromethyl, cyclopropyl, cyano, and ethynyl; L is selected from $C_1$-$C_4$ alkyl and $C_2$-$C_4$ alkenyl, each optionally substituted with one to three moieties independently selected from halogen, cyano, $C_1$-$C_4$ alkyl, and $C_1$-$C_4$ alkoxy; or L is a bond; $R^7$ is selected from phenyl and 5-, 6-, 9-, or 10-membered heteroaryl, each optionally substituted with one to three $R^y$ moieties; each $R^y$ is independently selected from halogen, cyano, nitro, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylsulfanyl, $C_1$-$C_4$ haloalkylsulfanyl, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, $C_1$-$C_4$ alkoxy-$C_1$-$C_4$ alkyl, —COOH, —COOR$^9$, —CONHR$^9$, —CONR$^{9a}$R$^9$, —NHCOR$^9$, —CH=N—OH, —CH=N—OR$^9$, and —COR$^9$; wherein said $C_1$-$C_4$ alkyl, $C_1$-$C_4$ haloalkyl, $C_1$-$C_4$ alkoxy, $C_1$-$C_4$ haloalkoxy, $C_1$-$C_4$ alkylsulfanyl, $C_1$-$C_4$ haloalkylsulfanyl, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and $C_1$-$C_4$ alkoxy-$C_1$-$C_4$ alkyl (of $R^y$) is optionally substituted with one to four $R^z$; $R^9$ and $R^{9a}$ are independently $C_1$-$C_4$ alkyl, each optionally substituted with one to four $R^z$ moieties; each $R^z$ is independently selected from halogen, cyano, nitro, $C_1$-$C_4$ alkyl, $C_1$-$C_4$ haloalkyl, —OH, $C_1$-$C_4$ alkoxy, and $C_1$-$C_4$ haloalkoxy; two $R^y$ moieties, together with the atom to which they are attached, are optionally joined to form a ring selected from a 4-, 5- or 6-membered carbocycle and a 4-, 5- or 6-membered heterocycle, each optionally substituted with one to three $R^z$ moieties; with the proviso that when $R^7$ is phenyl, said phenyl is not substituted at the para position (relative to the attachment point to L) with $C_3$-$C_6$ cycloalkyl or substituted $C_3$-$C_6$ cycloalkyl. In some embodiments, the invention provides salts or N-oxides of a compound as defined in this paragraph, and isomers, tautomers, enantiomers or diastereomers of these compounds.

In some embodiments, the invention provides a compound of Formula (I):

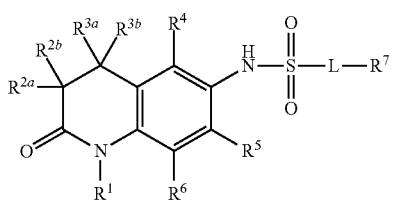

I wherein $R^1$ is selected from $C_1$-$C_6$ alkyl, $C_2$-$C_6$ alkenyl, and $C_3$-$C_4$ cycloalkyl; $R^{2a}$, $R^{2b}$, $R^{3a}$, and $R^{3b}$ are independently selected from hydrogen, methyl, ethyl, and halogen; or two members selected from $R^{2a}$, $R^{2b}$, $R^{3a}$, and $R^{3b}$, together with the atom to which they are attached, are joined to form a cyclopropyl; $R^4$, $R^5$, and $R^6$ are independently selected from hydrogen, halogen, fluoromethyl, difluoromethyl, trifluoromethyl, cyclopropyl, cyano, and ethynyl, wherein at least one of $R^4$, $R^5$, and $R^6$ is not hydrogen; L is selected from a bond and $C_1$-$C_2$ alkyl; $R^7$ is selected from phenyl and 5- or 6-membered heteroaryl, each optionally substituted with one to three $R^y$; each $R^y$ is independently selected from halogen, cyano, nitro, $C_1$-$C_4$ alkyl, $C_1$-$C_4$ haloalkyl, $C_1$-$C_4$ haloalkoxy, $C_1$-$C_4$ alkoxy-$C_1$-$C_4$ alkyl, and $COOR^9$; $R^9$ is $C_1$-$C_4$ alkyl; with the proviso that when $R^7$ is phenyl, said phenyl is not substituted at the para position (relative to the attachment point to L) with $C_3$-$C_4$ cycloalkyl. In some embodiments, the invention provides salts or N-oxides of a compound as defined in this paragraph, and isomers, tautomers, enantiomers or diastereomers of these compounds.

In some embodiments, the invention provides a compound of Formula (Ib):

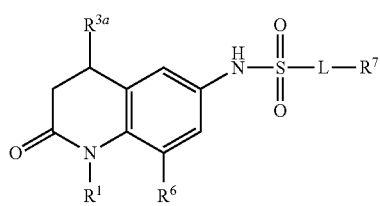

Ib or salts or N-oxides thereof, and isomers, tautomers, enantiomers or diastereomers of these compounds. $R^1$, $R^{3a}$, $R^6$, L, and $R^7$ are as defined herein. Any combination of $R^1$, $R^{3a}$, $R^6$, L, and $R^7$ is encompassed by this disclosure and specifically provided by the invention.

In some embodiments, the invention provides a compound of Formula (Ib):

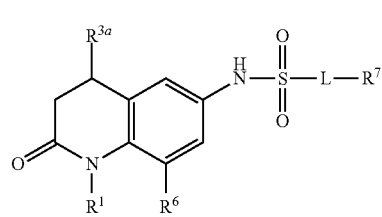

Ib wherein $R^1$ is selected from $C_1$-$C_6$ alkyl, $C_2$-$C_6$ alkenyl, and $C_3$-$C_4$ cycloalkyl; $R^{3a}$ is selected from hydrogen and methyl; $R^6$ is fluoro; L is $C_1$-$C_2$ alkyl; and $R^7$ is phenyl optionally substituted with one to three $R^y$; each $R^y$ is independently selected from halogen, nitro, $C_1$-$C_4$ alkyl, $C_1$-$C_4$ haloalkyl, $C_1$-$C_4$ haloalkoxy, $C_1$-$C_4$ alkoxy-$C_1$-$C_4$ alkyl, and $COOR^9$; $R^9$ is $C_1$-$C_4$ alkyl; with the proviso that the phenyl of $R^7$ is not substituted at the para position (relative to the attachment point to L) with $C_3$-$C_4$ cycloalkyl. In some embodiments, the invention provides salts or N-oxides of a compound as defined in this paragraph, and isomers, tautomers, enantiomers or diastereomers of these compounds.

In some embodiments, the invention provides a compound of Formula (Ia):

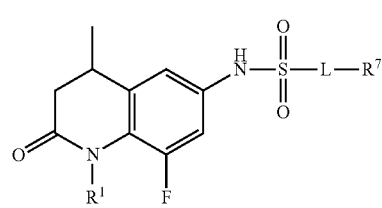

Ia or salts or N-oxides thereof, and isomers, tautomers, enantiomers or diastereomers of these compounds. $R^1$, L, and $R^7$ are as defined herein. Any combination of $R^1$, L, and $R^7$ is encompassed by this disclosure and specifically provided by the invention.

In some embodiments, the invention provides a compound of Formula (Ia):

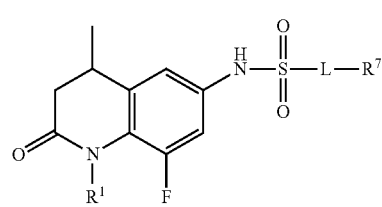

Ia wherein $R^1$ is selected from $C_3$-$C_4$ cycloalkyl and $C_2$-$C_6$ alkenyl; or $R^1$ is $C_1$-$C_4$ alkyl, optionally substituted with one to three $R^x$ moieties; each $R^x$ is independently selected from halogen, cyano, hydroxy, $C_1$-$C_4$ alkyl, $C_1$-$C_4$ alkoxy, $C_3$-$C_4$ cycloalkyl, and (C$_1$-C$_3$ alkoxy)-carbonyl; L is —CH$_2$—; and R$^7$ is selected from aryl and heteroaryl, each optionally substituted with one to three R$^y$ moieties; each R$^y$ is independently selected from halogen, cyano, C$_1$-C$_4$ alkyl, C$_1$-C$_4$ haloalkyl, C$_1$-C$_4$ alkoxy, C$_1$-C$_4$ haloalkoxy, C$_1$-C$_4$ haloalkylsulfanyl, C$_2$-C$_6$ alkenyl, C$_2$-C$_6$ alkynyl, C$_1$-C$_4$ alkoxy-C$_1$-C$_4$ alkyl, and —CH=N—OR$^9$; wherein the C$_1$-C$_4$ alkyl (of R$^y$) is optionally substituted with one to four R$^z$ moieties; R$^9$ is C$_1$-C$_4$ alkyl; each R$^z$ is independently selected from halogen and C$_1$-C$_4$ alkyl; two R$^y$ moieties, together with the atom to which they are attached, are optionally joined to form a 5-membered heterocycle, which is optionally substituted with one to three R$^z$ moieties; with the proviso that when R$^7$ is phenyl, the phenyl (of R$^7$) is not substituted at the para position (relative to the attachment point to L) with C$_3$-C$_4$ cycloalkyl or substituted C$_3$-C$_4$ cycloalkyl. In some embodiments, the invention provides salts or N-oxides of a compound as defined in this paragraph, and isomers, tautomers, enantiomers or diastereomers of these compounds. In some embodiments, R$^1$ is selected from C$_1$-C$_8$ alkyl, cyano-C$_1$-C$_4$ alkyl, C$_1$-C$_4$ haloalkyl, C$_1$-C$_4$ hydroxyalkyl, C$_1$-C$_4$ alkoxy-C$_1$-C$_4$ alkyl, C$_3$-C$_4$ cycloalkyl-C$_1$-C$_4$ alkyl, (C$_1$-C$_3$ alkoxy)-carbonyl-C$_1$-C$_4$ alkyl, C$_3$-C$_4$ cycloalkyl, and C$_2$-C$_6$ alkenyl; L is as defined in this paragraph; and R$^7$ is as defined in this paragraph. In some embodiments, R$^1$ is as defined in this paragraph; L is as defined in this paragraph; and R$^7$ is selected from phenyl, thienyl, pyridyl and benzo[d]thiazolyl, each optionally substituted with one to three R$^y$ moieties as this radical is defined in this paragraph; with the proviso that when R$^7$ is phenyl, the phenyl (of R$^7$) is not substituted at the para position (relative to the attachment point to L) with C$_3$-C$_4$ cycloalkyl or substituted C$_3$-C$_4$ cycloalkyl.

In some embodiments, the invention provides a compound of Formula (Ia):

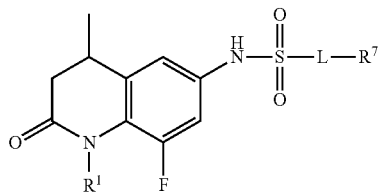

Ia wherein R$^1$ and the

Figure 5A:
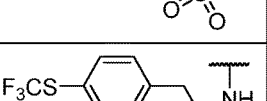
Figure 5A:
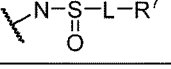
Figure 5A:
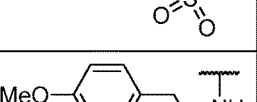
Figure 5A:
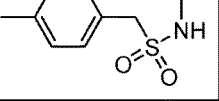
Figure 5A:
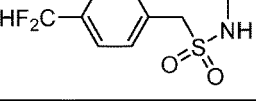
Figure 5A:
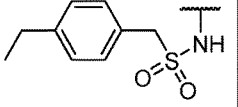
Figure 5A:
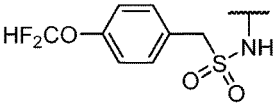
Figure 5A:
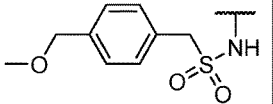
Figure 5A:
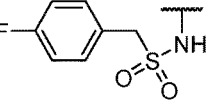
Figure 5A:
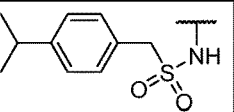
Figure 5A:
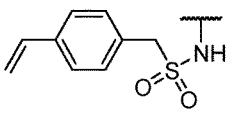
Figure 5A:
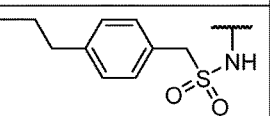
Figure 5A:
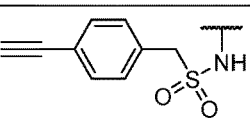
Figure 5A:
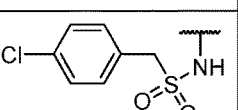
Figure 5A:
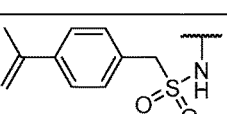
Figure 5A:
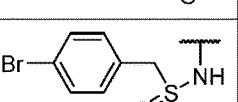
Figure 5A:
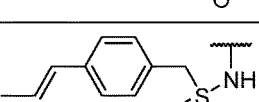
Figure 5A:
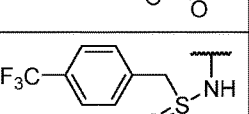
Figure 5A:
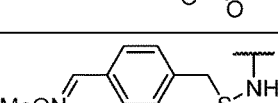
Figure 5A:
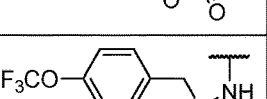
Figure 5B:
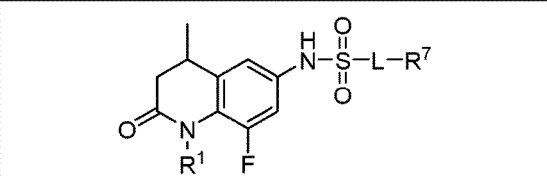
Figure 5B:
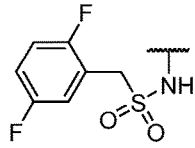
Figure 5B:
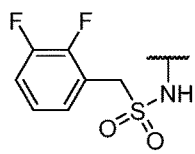
Figure 5B:
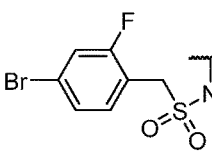
Figure 5B:
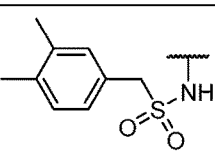
Figure 5B:
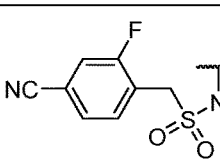
Figure 5B:
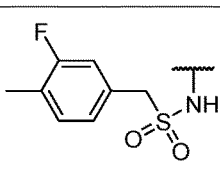
Figure 5B:
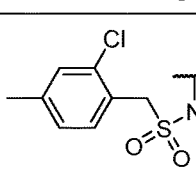
Figure 5B:
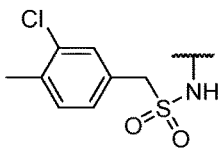
Figure 5B:
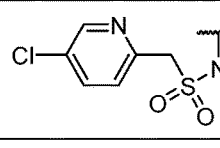
Figure 5B:
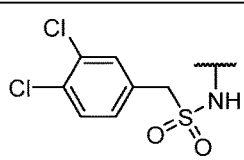
Figure 5B:
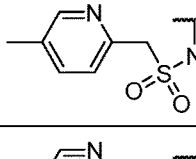
Figure 5B:
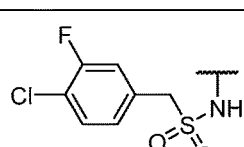
Figure 5B:
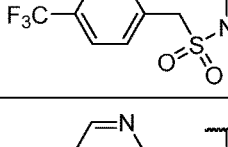
Figure 5B:
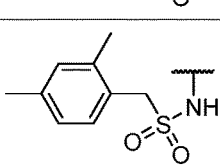
Figure 5B:
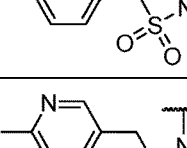
Figure 5B:
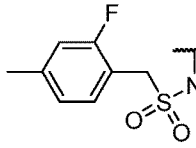
Figure 5B:
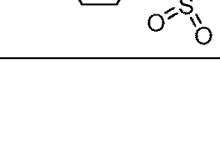
Figure 5C:
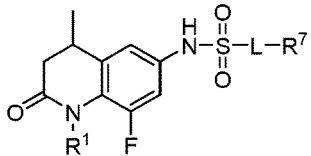
Figure 5C:
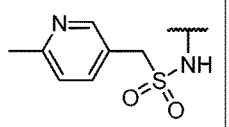
Figure 5C:
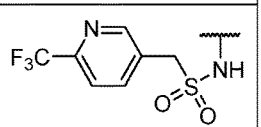
Figure 5C:
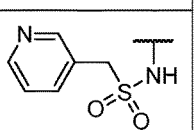
Figure 5C:
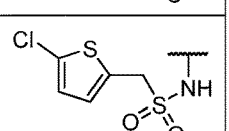
Figure 5C:
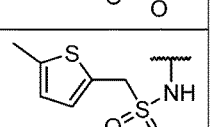
Figure 5C:
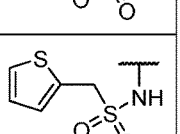
Figure 5C:
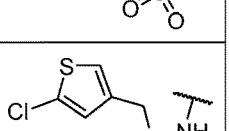
Figure 5C:
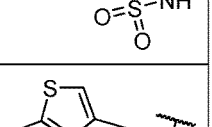
Figure 5C:
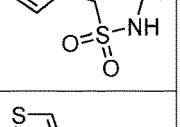
Figure 5C:
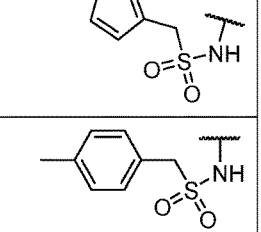
Figure 5C:
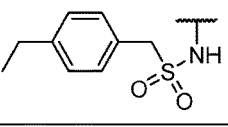
Figure 5C:
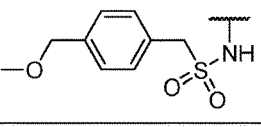
Figure 5C:
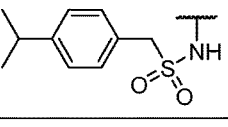
Figure 5C:
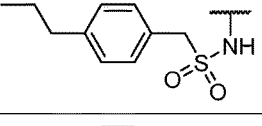
Figure 5C:
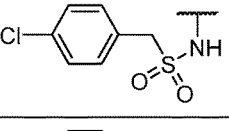
Figure 5C:
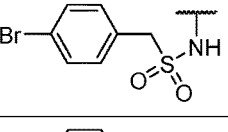
Figure 5C:
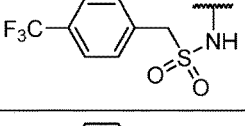
Figure 5C:
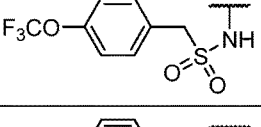
Figure 5C:
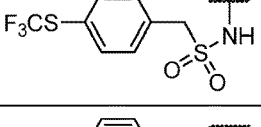
Figure 5C:
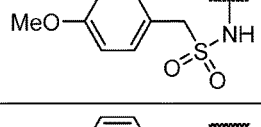
Figure 5C:
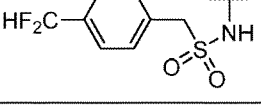
Figure 5G:
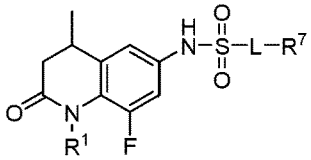
Figure 5J:
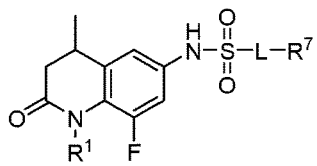
Figure 5J:
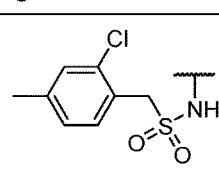
Figure 5J:
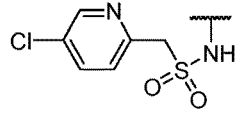
Figure 5J:
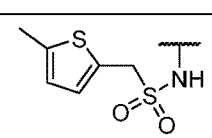
Figure 5J:
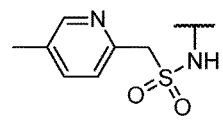
Figure 5J:
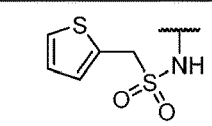
Figure 5J:
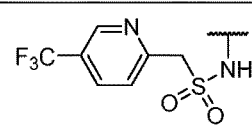
Figure 5J:
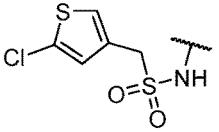
Figure 5J:
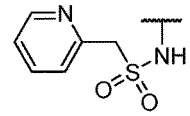
Figure 5J:
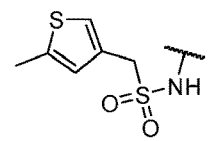
Figure 5J:
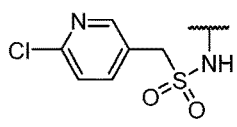
Figure 5J:
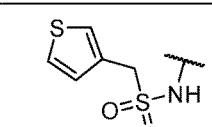
Figure 5J:
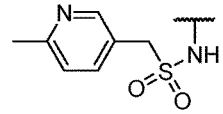
Figure 5J:
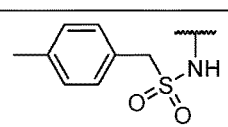
Figure 5J:
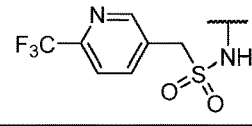
Figure 5J:
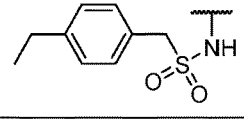
Figure 5J:
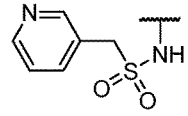
Figure 5J:
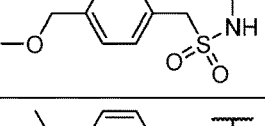
Figure 5J:
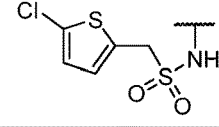
Figure 5J:
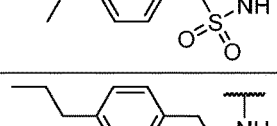
Figure 5J:
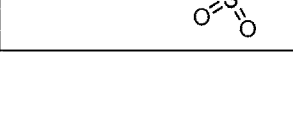
Figure 5K:
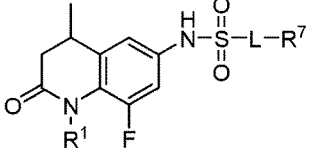
Figure 5K:
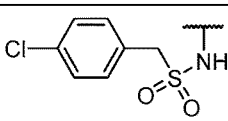
Figure 5K:
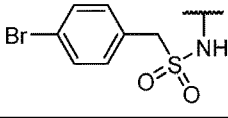
Figure 5K:
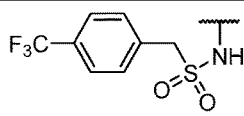
Figure 5K:
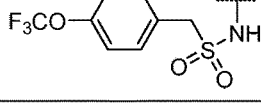
Figure 5K:
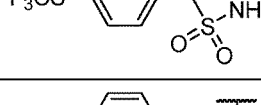
Figure 5K:
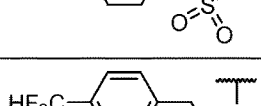
Figure 5K:
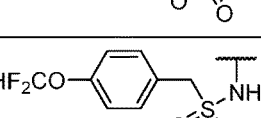
Figure 5K:
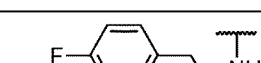
Figure 5K:
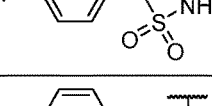
Figure 5K:
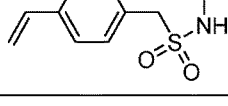
Figure 5K:
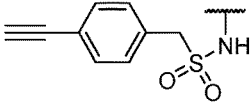
Figure 5K:
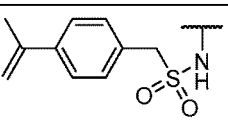
Figure 5K:
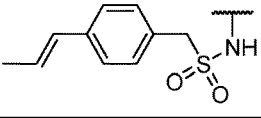
Figure 5K:
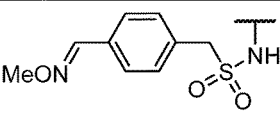
Figure 5K:
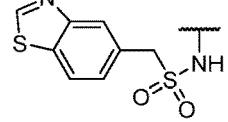
Figure 5K:
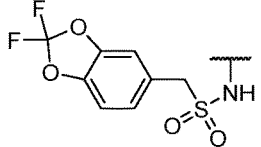
Figure 5K:
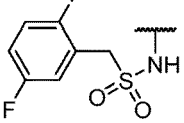
Figure 5K:
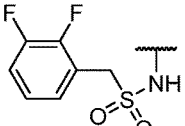
Figure 5K:
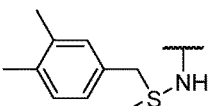
Figure 5K:
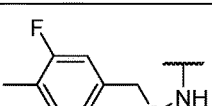
Figure 5P:
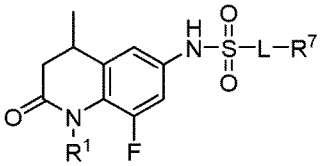
Figure 5P:
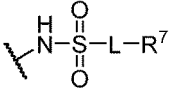
Figure 5P:
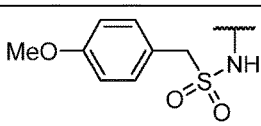
Figure 5P:
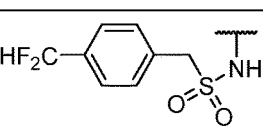
Figure 5P:
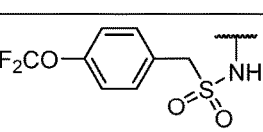
Figure 5P:
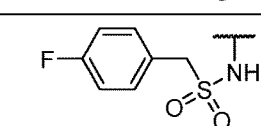
Figure 5P:
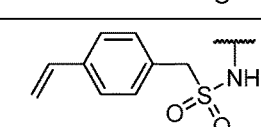
Figure 5P:
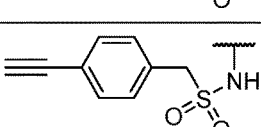
Figure 5P:
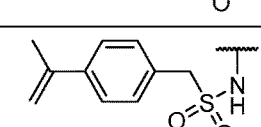
Figure 5P:
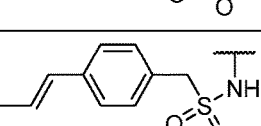
Figure 5P:
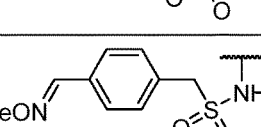
Figure 5P:
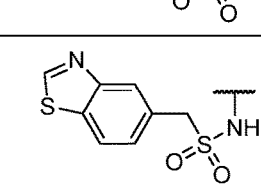
Figure 5P:
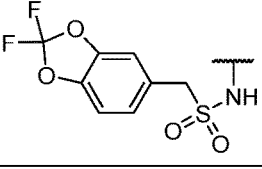
Figure 5P:
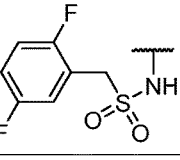
Figure 5P:
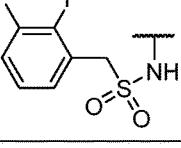
Figure 5P:
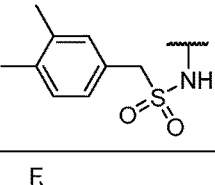
Figure 5P:
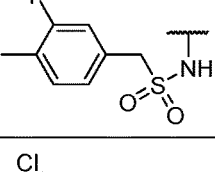
Figure 5P:
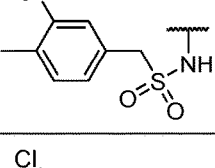
Figure 5P:
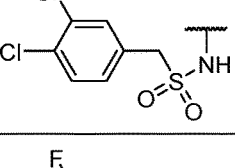
Figure 5T:
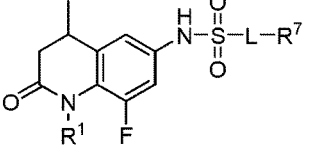
Figure 5T:
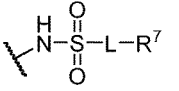
Figure 5T:
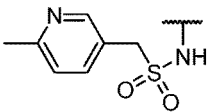
Figure 5T:
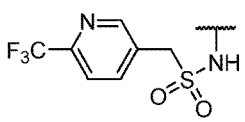
Figure 5T:
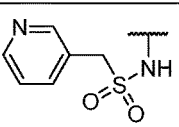
Figure 5T:
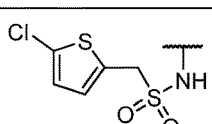
Figure 5T:
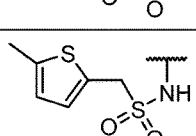
Figure 5T:
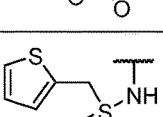
Figure 5T:
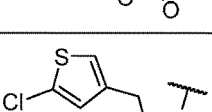
Figure 5T:
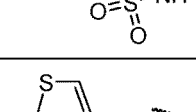
Figure 5T:
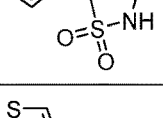
Figure 5T:
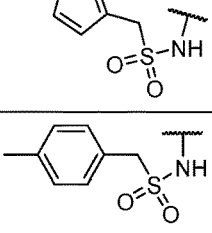
Figure 5T:
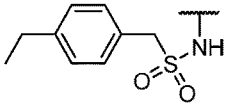
Figure 5T:
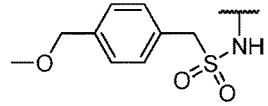
Figure 5T:
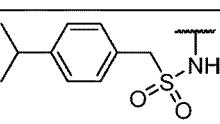
Figure 5T:
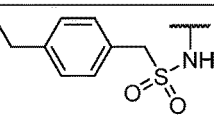
Figure 5T:
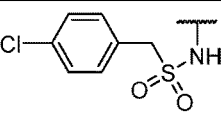
Figure 5T:
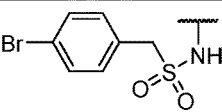
Figure 5T:
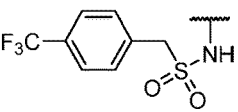
Figure 5T:
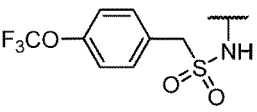
Figure 5T:
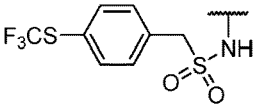
Figure 5T:
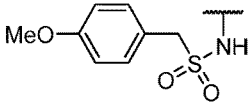
Figure 5Z:
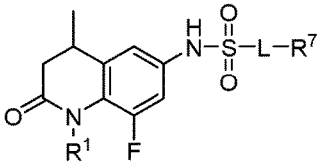
Figure 5Z:
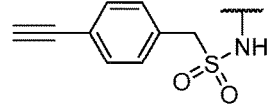
Figure 5Z:
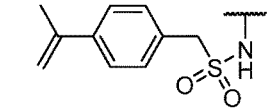
Figure 5Z:
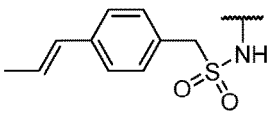
Figure 5Z:
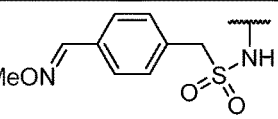
Figure 5Z:
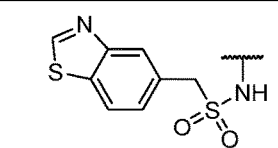
Figure 5Z:
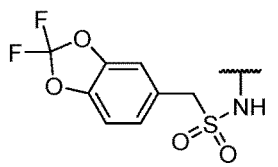
Figure 5Z:
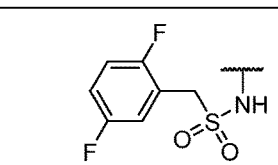
Figure 5Z:
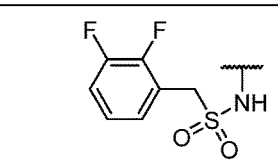
Figure 5Z:
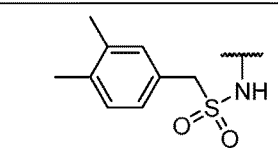
Figure 5Z:
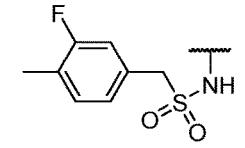
Figure 5Z:
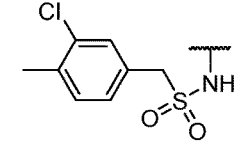
Figure 5Z:
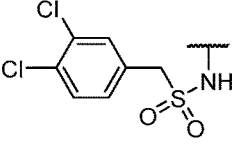
Figure 5Z:
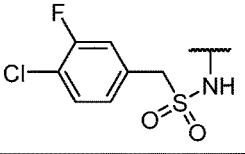
Figure 5Z:
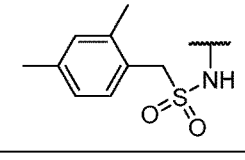
Figure 5Z:
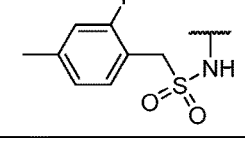
Figure 5Z:
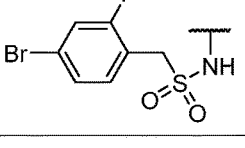
Figure 5E:
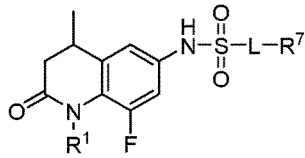
Figure 5E:
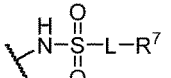
Figure 5E:
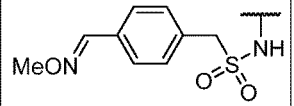
Figure 5E:
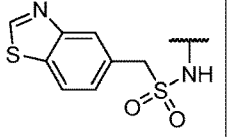
Figure 5E:
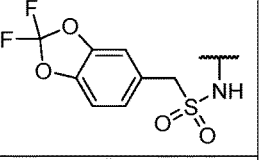
Figure 5E:
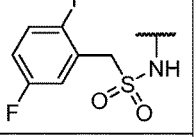
Figure 5E:
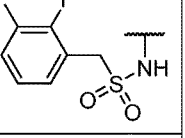
Figure 5E:
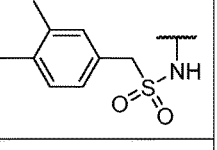
Figure 5E:
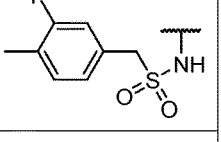
Figure 5E:
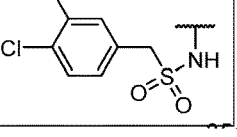
Figure 5E:
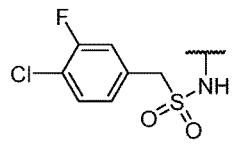
Figure 5E:
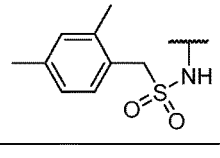
Figure 5E:
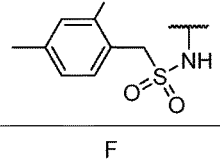
Figure 5E:
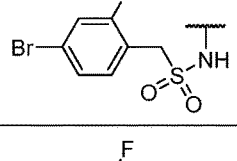
Figure 5E:
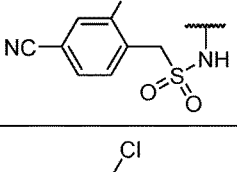
Figure 5E:
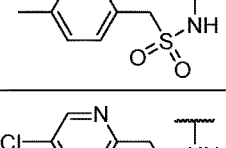
Figure 5E:
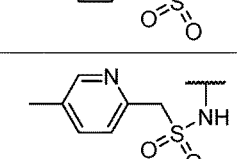
Figure 5E:
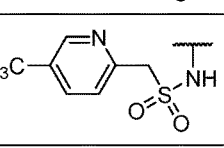

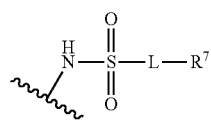

moiety are as defined in FIG. 5; or salts or N-oxides thereof, and isomers, tautomers, enantiomers or diastereomers of these compounds. In some embodiments, the compound is selected from those listed in FIG. 5.

Exemplary compounds of the invention are shown in the Examples and Scheme 1 below, as well as in FIG. 5.

Scheme 1. Exemplary compounds of the invention.

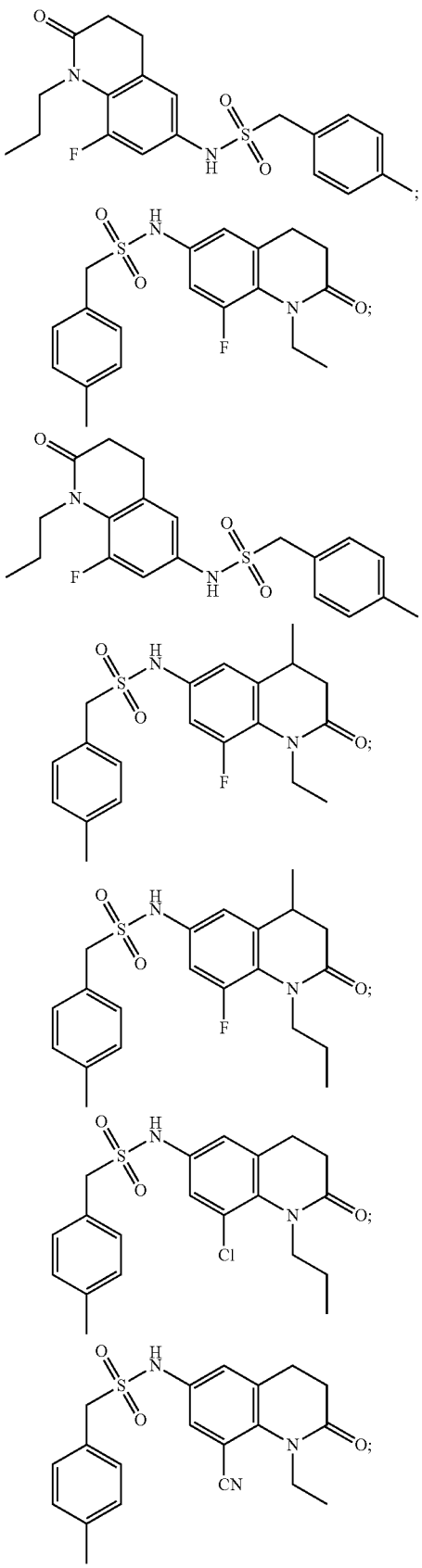

-continued

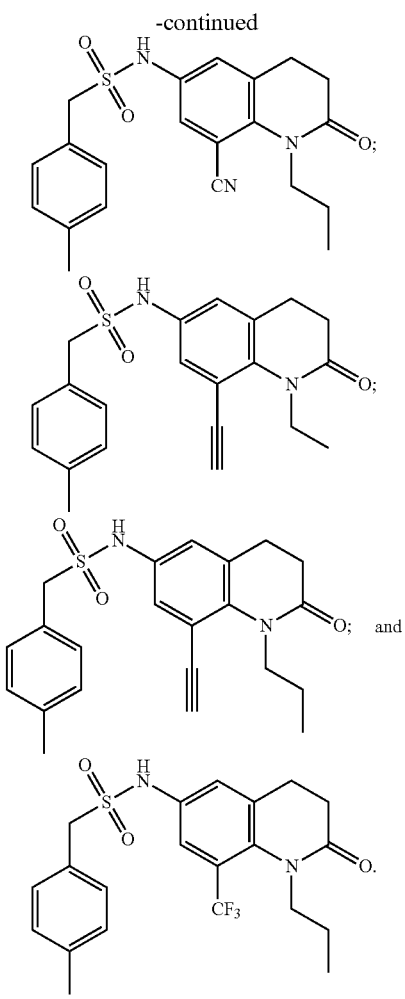

In some embodiments, the compound is selected from those listed in Table 1 (see Example 1), i.e., HQ1 to HQ57. In some embodiments, the compound is selected from HQ35, HQ48, HQ30, HQ29, HQ28, HQ1, HQ2, HQ11, HQ18, and HQ25. In some embodiments, the compound is selected from HQ31, HQ32, HQ33, HQ34, HQ35, HQ36, HQ37, HQ38, HQ39, HQ47, HQ48, HQ49, HQ52, HQ53, HQ57, HQ30, HQ29, HQ18, HQ25, HQ1, and HQ2. In some embodiments, the compound is selected from HQ33, HQ35, HQ48, and HQ52. In some embodiments, the compound is selected from HQ30, HQ35 and HQ48.

Compounds of the invention are generally conventionally synthesized. See, for example, International Application No. PCT/US15/44192; filed Aug. 7, 2015; titled "Plant Growth Regulator Compounds" and WO 2014/210555 A1. The synthetic methods known in the art and described herein can be used to synthesize compounds of the invention, using appropriate precursors.

Compositions and Uses

In one embodiment, the compounds of the present invention are applied in combination with an agriculturally acceptable adjuvant. In particular, there is provided a composition comprising a compound of the present invention and an agriculturally acceptable adjuvant. There may also be mentioned an agrochemical composition comprising a compound of the present invention.

The present invention provides a method of improving the tolerance of a plant to abiotic stress, wherein the method comprises applying to the plant, plant part, plant propagation material, or plant growing locus a compound, composition or mixture according to the present invention.

The present invention provides a method for regulating or improving the growth of a plant, wherein the method comprises applying to the plant, plant part, plant propagation material, or plant growing locus a compound, composition or mixture according to the present invention. In one embodiment, plant growth is regulated or improved when the plant is subject to abiotic stress conditions.

The present invention also provides a method for inhibiting seed germination of a plant, comprising applying to the seed, or a locus containing seeds, a compound, composition or mixture according to the present invention.

The present invention also provides a method for safening a plant against phytotoxic effects of chemicals, comprising applying to the plant, plant part, plant propagation material, or plant growing locus a compound, composition or mixture according to the present invention.

Suitably the compound or composition is applied in an amount sufficient to elicit the desired response.

Other effects of regulating or improving the growth of a crop include a decrease in plant height, or reduction in tillering, which are beneficial features in crops or conditions where it is desirable to have less biomass and fewer tillers.

Any or all of the above crop enhancements may lead to an improved yield by improving e.g., plant physiology, plant growth and development and/or plant architecture. In the context of the present invention 'yield' includes, but is not limited to, (i) an increase in biomass production, grain yield, starch content, oil content and/or protein content, which may result from (a) an increase in the amount produced by the plant per se or (b) an improved ability to harvest plant matter, (ii) an improvement in the composition of the harvested material (e.g., improved sugar acid ratios, improved oil composition, increased nutritional value, reduction of anti-nutritional compounds, increased consumer health benefits) and/or (iii) an increased/facilitated ability to harvest the crop, improved processability of the crop and/or better storage stability/shelf life. Increased yield of an agricultural plant means that, where it is possible to take a quantitative measurement, the yield of a product of the respective plant is increased by a measurable amount over the yield of the same product of the plant produced under the same conditions, but without application of the present invention. According to the present invention, it is preferred that the yield be increased by at least 0.5%, more preferred at least 1%, even more preferred at least 2%, still more preferred at least 4%, preferably 5% or even more.

Any or all of the above crop enhancements may also lead to an improved utilisation of land, i.e. land which was previously unavailable or sub-optimal for cultivation may become available. For example, plants which show an increased ability to survive in drought conditions, may be able to be cultivated in areas of sub-optimal rainfall, e.g., perhaps on the fringe of a desert or even the desert itself.

In one aspect of the present invention, crop enhancements are made in the substantial absence of pressure from pests and/or diseases and/or abiotic stress. In a further aspect of the present invention, improvements in plant vigour, stress tolerance, quality and/or yield are made in the substantial absence of pressure from pests and/or diseases. For example pests and/or diseases may be controlled by a pesticidal treatment that is applied prior to, or at the same time as, the method of the present invention. In a still further aspect of the present invention, improvements in plant vigour, stress tolerance, quality and/or yield are made in the absence of pest and/or disease pressure. In a further embodiment, improvements in plant vigour, quality and/or yield are made in the absence, or substantial absence, of abiotic stress.

The compounds of the present invention can be used alone, but are generally formulated into compositions using formulation adjuvants, such as carriers, solvents and surface-active agents (SFAs). Thus, the present invention further provides a composition comprising a compound of the present invention and an agriculturally acceptable formulation adjuvant. There is also provided a composition consisting essentially of a compound of the present invention and an agriculturally acceptable formulation adjuvant. There is also provided a composition consisting of a compound of the present invention and an agriculturally acceptable formulation adjuvant.

The present invention further provides a plant growth regulator composition comprising a compound of the present invention and an agriculturally acceptable formulation adjuvant. There is also provided a plant growth regulator composition consisting essentially of a compound of the present invention and an agriculturally acceptable formulation adjuvant. There is also provided a plant growth regulator composition consisting of a compound of the present invention and an agriculturally acceptable formulation adjuvant.

The present invention further provides a plant abiotic stress management composition comprising a compound of the present invention and an agriculturally acceptable formulation adjuvant. There is also provided a plant abiotic stress management composition consisting essentially of a compound of the present invention and an agriculturally acceptable formulation adjuvant. There is also provided a plant abiotic stress management composition consisting of a compound of the present invention and an agriculturally acceptable formulation adjuvant.

The present invention further provides a seed germination inhibitor composition comprising a compound of the present invention and an agriculturally acceptable formulation adjuvant. There is also provided a seed germination inhibitor composition consisting essentially of a compound of the present invention and an agriculturally acceptable formulation adjuvant. There is also provided a seed germination inhibitor composition consisting of a compound of the present invention and an agriculturally acceptable formulation adjuvant.

The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

The compositions generally comprise from 0.1 to 99% by weight, especially from 0.1 to 95% by weight, compounds of the present invention and from 1 to 99.9% by weight of a formulation adjuvant which preferably includes from 0 to 25% by weight of a surface-active substance.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultralow volume liquids (UL), emulsifiable concentrates (EC), dispersible concentrates (DC), emulsions (both oil in water (EW) and water in oil (EO)), microemulsions (ME), suspension concentrates (SC), aerosols, capsule suspensions (CS) and seed treatment formulations. The formulation type chosen in any instance will depend upon the particular purpose envisaged and the physical, chemical and biological properties of the compound of the present invention.

Dustable powders (DP) may be prepared by mixing a compound of the present invention with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of the present invention with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of these agents to improve water dispersibility/solubility. The mixture is then ground to a fine powder. Similar compositions may also be granulated to form water soluble granules (SG).

Wettable powders (WP) may be prepared by mixing a compound of the present invention with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of the present invention and one or more powdered solid diluents or carriers, or from preformed blank granules by absorbing a compound of the present invention (or a solution thereof, in a suitable agent) in a porous granular material (such as pumice, attapulgite clays, fuller's earth, kieselguhr, diatomaceous earths or ground corn cobs) or by adsorbing a compound of the present invention (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of the present invention in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of the present invention in an organic solvent (optionally containing one or more wetting agents, one or more emulsifying agents or a mixture of these agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of the present invention either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of the present invention is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of the present invention. SCs may be prepared by ball or bead milling the solid compound of the present invention in a suitable medium, optionally with one or more dispersing agents, to produce a fine particle suspension of the compound. One or more wetting agents may be included in the composition and a suspending agent may be included to reduce the rate at which the particles settle. Alternatively, a compound of the present invention may be dry milled and added to water, containing agents hereinbefore described, to produce the desired end product.

Aerosol formulations comprise a compound of the present invention and a suitable propellant (for example n-butane). A compound of the present invention may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of the present invention and, optionally, a carrier or diluent therefor. The polymeric shell may be produced by either an interfacial polycondensation reaction or by a coacervation procedure. The compositions may provide for controlled release of the compound of the present invention and they may be used for seed treatment. A compound of the present invention may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of the present invention. Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of the present invention).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of the partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

The compound or composition of the present invention may be applied to a plant, part of the plant, plant organ, plant propagation material or a plant growing locus.

The application is generally made by spraying the composition, typically by tractor mounted sprayer for large areas, but other methods such as dusting (for powders), drip or drench can also be used. Alternatively the composition may be applied in furrow or directly to a seed before or at the time of planting.

The compound or composition of the present invention may be applied pre-emergence or post-emergence. Suitably, where the composition is used to regulate the growth of crop plants or enhance the tolerance to abiotic stress, it may be applied post-emergence of the crop. Where the composition is used to inhibit or delay the germination of seeds, it may be applied pre-emergence.

The present invention envisages application of the compounds or compositions of the invention to plant propagation material prior to, during, or after planting, or any combination of these.

Although active ingredients can be applied to plant propagation material in any physiological state, a common approach is to use seeds in a sufficiently durable state to incur no damage during the treatment process. Typically, seed would have been harvested from the field; removed from the plant; and separated from any cob, stalk, outer husk, and surrounding pulp or other non-seed plant material. Seed would preferably also be biologically stable to the extent that treatment would not cause biological damage to the seed. It is believed that treatment can be applied to seed at any time between seed harvest and sowing of seed including during the sowing process.

Methods for applying or treating active ingredients on to plant propagation material or to the locus of planting are known in the art and include dressing, coating, pelleting and soaking as well as nursery tray application, in furrow application, soil drenching, soil injection, drip irrigation, application through sprinklers or central pivot, or incorporation into soil (broad cast or in band). Alternatively or in addition active ingredients may be applied on a suitable substrate sown together with the plant propagation material.

The rates of application of compounds of the present invention may vary within wide limits and depend on the nature of the soil, the method of application (pre- or post-emergence; seed dressing; application to the seed furrow; no tillage application etc.), the crop plant, the prevailing climatic conditions, and other factors governed by the method of application, the time of application and the target crop. For foliar or drench application, the compounds of the present invention according to the invention are generally applied at a rate of from about 1 to about 2000 g/ha, especially from about 5 to about 1000 g/ha. For seed treatment the rate of application is generally from about 0.0005 to about 150 g per 100 kg of seed.

The compounds and compositions of the present invention may be applied to dicotyledonous or monocotyledonous crops.

Crops of useful plants in which the composition according to the invention can be used include perennial and annual crops, such as berry plants for example blackberries, blueberries, cranberries, raspberries and strawberries; cereals for example barley, maize (corn), millet, oats, rice, rye, sorghum triticale and wheat; fibre plants for example cotton, flax, hemp, jute and sisal; field crops for example sugar and fodder beet, coffee, hops, mustard, oilseed rape (canola), poppy, sugar cane, sunflower, tea and tobacco; fruit trees for example apple, apricot, avocado, banana, cherry, citrus, nectarine, peach, pear and plum; grasses for example Bermuda grass, bluegrass, bentgrass, centipede grass, fescue, ryegrass, St. Augustine grass and Zoysia grass; herbs such as basil, borage, chives, coriander, lavender, lovage, mint, oregano, parsley, rosemary, sage and thyme; legumes for example beans, lentils, peas and soya beans; nuts for example almond, cashew, ground nut, hazelnut, peanut, pecan, pistachio and walnut; palms for example oil palm; ornamentals for example flowers, shrubs and trees; other trees, for example cacao, coconut, olive and rubber; vegetables for example asparagus, aubergine, broccoli, cabbage, carrot, cucumber, garlic, lettuce, marrow, melon, okra, onion, pepper, potato, pumpkin, rhubarb, spinach and tomato; and vines for example grapes.

Crops are to be understood as being those which are naturally occurring, obtained by conventional methods of breeding, or obtained by genetic engineering. They include crops which contain so-called output traits (e.g., improved storage stability, higher nutritional value and improved flavour).

Crops are to be understood as also including those crops which have been rendered tolerant to herbicides like bromoxynil or classes of herbicides such as ALS-, EPSPS-, GS-, HPPD- and PPO-inhibitors. An example of a crop that has been rendered tolerant to imidazolinones, e.g., imazamox, by conventional methods of breeding is Clearfield® summer canola. Examples of crops that have been rendered tolerant to herbicides by genetic engineering methods include e.g., glyphosate- and glufosinate-resistant maize varieties commercially available under the trade names RoundupReady®, Herculex I® and LibertyLink®.

Crops are also to be understood as being those which naturally are or have been rendered resistant to harmful insects. This includes plants transformed by the use of recombinant DNA techniques, for example, to be capable of synthesising one or more selectively acting toxins, such as are known, for example, from toxin-producing bacteria. Examples of toxins which can be expressed include δ-endotoxins, vegetative insecticidal proteins (Vip), insecticidal proteins of bacteria colonising nematodes, and toxins produced by scorpions, arachnids, wasps and fungi.

An example of a crop that has been modified to express the *Bacillus thuringiensis* toxin is the Bt maize KnockOut® (Syngenta Seeds). An example of a crop comprising more than one gene that codes for insecticidal resistance and thus expresses more than one toxin is VipCot® (Syngenta Seeds). Crops or seed material thereof can also be resistant to multiple types of pests (so-called stacked transgenic events when created by genetic modification). For example, a plant can have the ability to express an insecticidal protein while at the same time being herbicide tolerant, for example Herculex I® (Dow AgroSciences, Pioneer Hi-Bred International).

Compounds of the present invention may also be used to inhibit or delay the germination of seeds of non-crop plants, for example as part of an integrated weed control program. A delay in germination of weed seeds may provide a crop seedling with a stronger start by reducing competition with weeds.

Alternatively compounds of the present invention may be used to delay the germination of seeds of crop plants, for example to increase the flexibility of timing of planting for the grower.

Normally, in the management of a crop a grower would use one or more other agronomic chemicals or biologicals in addition to the compound or composition of the present invention. There is also provided a mixture comprising a compound or composition of the present invention, and a further active ingredient.

Examples of agronomic chemicals or biologicals include pesticides, such as acaricides, bactericides, fungicides, herbicides, insecticides, nematicides, plant growth regulators, crop enhancing agents, safeners as well as plant nutrients and plant fertilizers. Examples of suitable mixing partners may be found in the Pesticide Manual, 15th edition (published by the British Crop Protection Council). Such mixtures may be applied to a plant, plant propagation material or plant growing locus either simultaneously (for example as a pre-formulated mixture or a tank mix), or sequentially in a suitable timescale. Co-application of pesticides with the present invention has the added benefit of minimising farmer time spent applying products to crops. The combination may also encompass specific plant traits incorporated into the plant using any means, for example conventional breeding or genetic modification.

The present invention also provides the use of a compound of Formula (I):

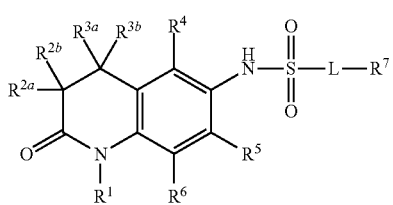

wherein $R^1$, $R^{2a}$, $R^{2b}$, $R^{3a}$, $R^{3b}$, $R^4$, $R^5$, $R^6$, L, and $R^7$ are as defined herein; or salts or N-oxides thereof, and isomers, tautomers, enantiomers or diastereomers of these compounds; or a composition comprising a compound according to Formula (I) and an agriculturally acceptable formulation adjuvant, for improving the tolerance of a plant to abiotic stress, regulating or improving the growth of a plant, inhibiting seed germination and/or safening a plant against phytotoxic effects of chemicals.

There is also provided the use of a compound, composition or mixture of the present invention, for improving the tolerance of a plant to abiotic stress, regulating or improving the growth of a plant, inhibiting seed germination and/or safening a plant against phytotoxic effects of chemicals.

By way of summary, in exemplary embodiments, the present invention provides a compound of Formula (I):

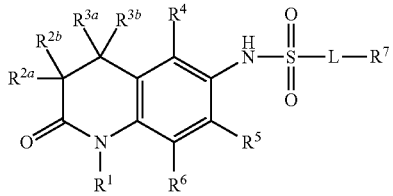

or salts or N-oxides thereof, and isomers, tautomers, enantiomers or diastereomers of these compounds. $R^1$ is selected from hydrogen, alkyl, cyano-alkyl, haloalkyl, alkoxy-alkyl, haloalkyl-alkyl, haloalkoxy-alkyl, cycloalkyl-alkyl, alkenyl, haloalkenyl, alkynyl, haloalkynyl, and heterocycloalkyl; or $R^1$ is selected from alkyl, alkyl-aryl, cycloalkyl, phenyl and heteroaryl, each optionally substituted with one to three independently selected $R^x$ moieties. Each $R^x$ is independently selected from halogen, cyano, hydroxy, alkyl, haloalkyl, alkoxy, haloalkoxy, alkylsulfanyl, haloalkylsulfanyl, alkylsulfinyl, haloalkylsulfinyl, alkylsulfonyl, haloalkylsulfonyl, cycloalkyl, and alkoxy-carbonyl. $R^{2a}$, $R^{2b}$, $R^{3a}$, and $R^{3b}$ are independently selected from hydrogen, halogen, cyano, alkyl, alkenyl, alkynyl, alkoxy, haloalkyl, haloalkoxy and cycloalkyl. Two members selected from $R^{2a}$, $R^{2b}$, $R^{3a}$, and $R^{3b}$, together with the atom to which they are attached, are optionally joined to form a cycloalkyl. $R^4$, $R^5$, and $R^6$ are independently selected from hydrogen, halogen, cyano, alkyl, alkenyl, alkynyl, alkoxy, haloalkyl, haloalkoxy and cycloalkyl. At least one of $R^4$, $R^5$, and $R^6$ is independently selected from halogen, fluoromethyl, difluoromethyl, trifluoromethyl, cyclopropyl, cyano, and ethynyl. L is selected from alkyl, alkenyl, alkynyl, and alkoxy, each optionally substituted with one to three moieties independently selected from halogen, cyano, alkyl, and alkoxy; or L is a bond. $R^7$ is selected from aryl, heteroaryl, alkyl, cycloalkyl, and heterocycloalkyl, each optionally substituted with one to five independently selected $R^y$ moieties. Each $R^y$ is independently selected from halogen, cyano, nitro, alkyl, haloalkyl, alkoxy, haloalkoxy, alkylsulfanyl, haloalkylsulfanyl, alkylsulfinyl, haloalkylsulfinyl, alkylsulfonyl, haloalkylsulfonyl, alkenyl, haloalkenyl, alkynyl, haloalkynyl, cycloalkyl, alkoxy-alkyl, —COOH, —COOR$^9$, —CONHR$^9$, —CONR$^{9a}$R$^9$, —NHCOR$^9$, —CH=N—OH, —CH=N—OR$^9$, and —COR$^9$; wherein the alkyl, haloalkyl, alkoxy, haloalkoxy, alkylsulfanyl, haloalkylsulfanyl, alkylsulfinyl, haloalkylsulfinyl, alkylsulfonyl, haloalkylsulfonyl, alkenyl, haloalkenyl, alkynyl, haloalkynyl, cycloalkyl, and alkoxy-alkyl is optionally substituted with one to four independently selected $R^z$ moieties. $R^9$ and $R^{9a}$ are independently alkyl, each optionally substituted with one to four independently selected $R^z$ moieties. Each $R^z$ is independently selected from halogen, cyano, nitro, alkyl, haloalkyl, —OH, alkoxy, and haloalkoxy. Two independently selected $R^y$ moieties, together with the atom to which they are attached, are optionally joined to form a ring, which is optionally substituted with one to three independently selected $R^z$ moieties. When $R^7$ is phenyl, the phenyl is not substituted at the para position (relative to the attachment point to L) with $C_3$-$C_6$ cycloalkyl or substituted $C_3$-$C_6$ cycloalkyl.

In various embodiments, the invention provides a compound according to the preceding paragraph, wherein each $R^x$ is independently selected from halogen, cyano, hydroxy, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylsulfanyl, $C_1$-$C_4$ haloalkylsulfanyl, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, $C_3$-$C_4$ cycloalkyl, and ($C_1$-$C_3$ alkoxy)-carbonyl.

In an exemplary embodiment, the invention provides a compound according to any preceding paragraph, wherein each $R^x$ is independently selected from halogen, cyano, $C_1$-$C_3$ alkyl, $C_1$-$C_3$ haloalkyl, $C_1$-$C_3$ alkoxy, $C_1$-$C_3$ haloalkoxy and $C_3$-$C_4$ cycloalkyl.

The invention further provides compounds according to any preceding paragraph, wherein $R^1$ is selected from hydrogen, $C_1$-$C_6$ alkyl, cyano-$C_1$-$C_6$ alkyl, $C_1$-$C_6$ haloalkyl, $C_1$-$C_3$ alkoxy-$C_1$-$C_6$ alkyl, $C_1$-$C_3$ haloalkyl-$C_1$-$C_6$ alkyl, $C_1$-$C_3$ haloalkoxy-$C_1$-$C_6$ alkyl, $C_3$-$C_4$ cycloalkyl-$C_1$-$C_3$ alkyl, $C_2$-$C_6$ alkenyl, $C_2$-$C_6$ haloalkenyl, $C_2$-$C_6$ alkynyl, $C_2$-$C_6$ haloalkynyl, and $C_4$-$C_5$ heterocycloalkyl; or $R^1$ is selected from $C_1$-$C_4$ alkyl, $C_1$-$C_4$ alkyl-aryl, $C_3$-$C_5$ cycloalkyl, phenyl and 5- or 6-membered heteroaryl, each optionally substituted with one to three $R^x$.

In various embodiments, the invention provides a compound according to any preceding paragraph, wherein $R^1$ is selected from $C_3$-$C_4$ cycloalkyl, phenyl and 5- or 6-membered heteroaryl, each optionally substituted with one to three $R^x$; or $R^1$ is selected from hydrogen, $C_1$-$C_6$ alkyl, $C_1$-$C_6$ haloalkyl, $C_1$-$C_3$ alkoxy-$C_1$-$C_3$ alkyl, $C_1$-haloalkoxy-$C_1$-$C_3$ alkyl, $C_3$-$C_4$ cycloalkyl-$C_1$-$C_3$ alkyl, $C_2$-$C_6$ alkenyl and $C_2$-$C_6$ alkynyl.

Also provided in representative embodiments is a compound according to any preceding paragraph, wherein $R^1$ is selected from $C_1$-$C_6$ alkyl, $C_2$-$C_6$ alkenyl, and $C_3$-$C_4$ cycloalkyl.

Exemplary embodiments of the invention provide a compound according to any preceding paragraph, wherein $R^1$ is selected from ethyl, n-propyl, isopropyl, allyl, and cyclopropyl.

Also provided in representative embodiments is a compound according to any preceding paragraph, wherein $R^{2a}$, $R^{2b}$, $R^{3a}$, and $R^{3b}$ are independently selected from hydrogen, halogen, cyano, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy and $C_3$-$C_4$ cycloalkyl; or two members selected from $R^{2a}$, $R^{2b}$, $R^{3a}$, and $R^{3b}$, together with the atom to which they are attached, are optionally joined to form a $C_3$-$C_4$ cycloalkyl.

The invention further provides a compound according to any preceding paragraph, wherein $R^{2a}$, $R^{2b}$, $R^{3a}$, and $R^{3b}$ are independently selected from hydrogen, methyl, ethyl, and halogen; or two members selected from $R^{2a}$, $R^{2b}$, $R^{3a}$, and $R^{3b}$, together with the atom to which they are attached, are joined to form a cyclopropyl.

A compound according to any preceding paragraph, wherein $R^{2a}$, $R^{2b}$, and $R^{3b}$ are hydrogen; and $R^{3a}$ is selected from hydrogen and methyl.

In exemplary compounds according to any preceding paragraph, $R^4$, $R^5$, and $R^6$ are independently selected from hydrogen, halogen, cyano, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy and $C_3$-$C_4$ cycloalkyl. At least one of $R^4$, $R^5$, and $R^6$ is selected from halogen, difluoromethyl, trifluoromethyl, cyclopropyl, cyano, and ethynyl.

A compound according to any preceding paragraph, wherein $R^4$, $R^5$, and $R^6$ are independently selected from hydrogen, halogen, fluoromethyl, difluoromethyl, trifluoromethyl, cyclopropyl, cyano, and ethynyl, wherein at least one of $R^4$, $R^5$, and $R^6$ is not hydrogen.

The invention also provides a compound according to any preceding paragraph, wherein $R^4$ and $R^5$ are hydrogen.

In various embodiments, the invention provides a compound according to any preceding paragraph, wherein $R^6$ is selected from fluoro, chloro, cyano, ethynyl, and trifluoromethyl.

There is also provided a compound according to any preceding paragraph, wherein L is selected from $C_1$-$C_4$ alkyl and $C_2$-$C_4$ alkenyl, each optionally substituted with one to three moieties independently selected from halogen, cyano, $C_1$-$C_4$ alkyl, and $C_1$-$C_4$ alkoxy; or L is a bond.

A compound according to any preceding paragraph, wherein L is $C_1$-$C_2$ alkyl optionally substituted with one or two moieties independently selected from halogen, cyano and $C_1$-$C_2$ alkyl.

Representative compounds according to any preceding paragraph, include and L moiety which is selected from $C_1$-$C_2$ alkyl.

An exemplary embodiments provides a compound according to any preceding paragraph, wherein L is —$CH_2$—.

In various embodiments, the invention provides compound according to any preceding paragraph, wherein each $R^z$ is independently selected from halogen, cyano, nitro, $C_1$-$C_4$ alkyl, $C_1$-$C_4$ haloalkyl, —OH, $C_1$-$C_4$ alkoxy, and $C_1$-$C_4$ haloalkoxy.

Also provided is a compound according to any preceding paragraph, wherein each $R^y$ is independently selected from halogen, cyano, nitro, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylsulfanyl, $C_1$-$C_4$ haloalkylsulfanyl, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, $C_1$-$C_4$ alkoxy-$C_1$-$C_4$ alkyl, —COOH, —$COOR^9$, —$CONHR^9$, —$CONR^{9a}R^9$, —$NHCOR^9$, —CH=N—OH, —CH=N—$OR^9$, and —$COR^9$; wherein the $C_1$-$C_4$ alkyl, $C_1$-$C_4$ haloalkyl, $C_1$-$C_4$ alkoxy, $C_1$-$C_4$ haloalkoxy, $C_1$-$C_4$ alkylsulfanyl, $C_1$-$C_4$ haloalkylsulfanyl, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and $C_1$-$C_4$ alkoxy-$C_1$-$C_4$ alkyl is optionally substituted with one to four $R^z$ moieties. $R^9$ and $R^{9a}$ are independently $C_1$-$C_4$ alkyl, each optionally substituted with one to four $R^z$ moieties.

In a representative embodiments, there is provided a compound according to any preceding paragraph, wherein when $R^7$ is phenyl substituted with one to five $R^y$ moieties and none of the $R^y$ moieties is a $C_3$-$C_6$ cycloalkyl or substituted $C_3$-$C_6$ cycloalkyl.

A compound according to any preceding paragraph, wherein $R^7$ is selected from phenyl, thienyl and pyridyl, each optionally substituted with one to three $R^y$. Each $R^y$ is independently selected from halogen, cyano, nitro, $C_1$-$C_4$ alkyl, $C_1$-$C_4$ haloalkyl, $C_1$-$C_4$ haloalkoxy, $C_1$-$C_4$ alkoxy-$C_1$-$C_4$ alkyl, and $COOR^9$.

There is also provided a compound according to any preceding paragraph, wherein $R^7$ is selected from phenyl, thienyl and pyridyl, each optionally substituted with one or two moieties selected from methyl, ethyl, fluoro, chloro, bromo, cyano, trifluoromethyl, trifluoromethoxy, methoxymethyl, methoxycarbonyl, and nitro.

The invention further provides a compound according to any preceding paragraph, wherein the compound is of Formula (Ia):

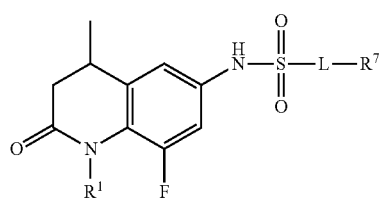

Ia $R^1$ is selected from $C_3$-$C_4$ cycloalkyl and $C_2$-$C_6$ alkenyl; or $R^1$ is $C_1$-$C_4$ alkyl, optionally substituted with one to three independently selected $R^x$ moieties. Each $R^x$ is independently selected from halogen, cyano, hydroxy, $C_1$-$C_4$ alkyl, $C_1$-$C_4$ alkoxy, $C_3$-$C_4$ cycloalkyl, and ($C_1$-$C_3$ alkoxy)-carbonyl. L is —$CH_2$—. $R^7$ is selected from aryl and heteroaryl, each optionally substituted with one to three independently selected $R^y$ moieties. Each $R^y$ is independently selected from halogen, cyano, $C_1$-$C_4$ alkyl, $C_1$-$C_4$ haloalkyl, $C_1$-$C_4$ alkoxy, $C_1$-$C_4$ haloalkoxy, $C_1$-$C_4$ haloalkylsulfanyl, $C_2$-$C_6$ alkenyl, $C_2$-$C_6$ alkynyl, $C_1$-$C_4$ alkoxy-$C_1$-$C_4$ alkyl, and —CH=N—$OR^9$; wherein the $C_1$-$C_4$ alkyl is optionally substituted with one to four independently selected $R^z$ moieties. $R^9$ is $C_1$-$C_4$ alkyl. Each $R^z$ is independently selected from halogen and $C_1$-$C_4$ alkyl. Two independently selected $R^y$ moieties, together with the atom to which they are attached, are optionally joined to form a 5-membered heterocycle, which is optionally substituted with one to three independently selected $R^z$ moieties. When $R^7$ is phenyl, the phenyl is not substituted at the para position (relative to the attachment point to L) with $C_3$-$C_4$ cycloalkyl or substituted $C_3$-$C_4$ cycloalkyl.

The invention also provides a composition comprising a compound as defined in any preceding paragraph, and an agriculturally acceptable formulation adjuvant.

There is also provided a mixture comprising a compound as defined in any preceding paragraph, and a further active ingredient.

The invention also provides methods. In one embodiment, there is provided a method for improving the tolerance of a plant to abiotic stress, wherein the method comprises applying to the plant, plant part, plant propagation material, or plant growing locus a compound according to any preceding paragraph, a composition according to any preceding paragraph, or a mixture according to any preceding paragraph.

There is also provided a method for inhibiting seed germination of a plant, wherein the method comprises applying to the seed or a locus containing seeds a compound according to any preceding paragraph, a composition according to any preceding paragraph, or a mixture according to any preceding paragraph.

In various embodiments, there is provided a method for regulating or improving the growth of a plant, wherein the method comprises applying to the plant, plant part, plant propagation material, or plant growing locus a compound according to any preceding paragraph, a composition according to any preceding paragraph, or a mixture according to any preceding paragraph.

Also provided is a method for safening a plant against phytotoxic effects of chemicals, comprising applying to the plant, plant part, plant propagation material, or plant growing locus a compound, according to any preceding paragraph, a composition according to any preceding paragraph, or a mixture according to any preceding paragraph.

The invention also provides for the use of a compound of Formula (I):

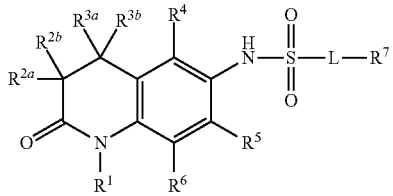

as defined in any preceding paragraph, or salts or N-oxides thereof, and isomers, tautomers, enantiomers or diastereomers of these compounds; or a composition comprising a compound according to Formula (I) and an agriculturally acceptable formulation adjuvant, for improving the tolerance of a plant to abiotic stress, regulating or improving the growth of a plant, inhibiting seed germination and/or safening a plant against phytotoxic effects of chemicals.

The materials and methods of the present invention are further illustrated by the examples which follow. These examples are offered to illustrate, but not to limit the claimed invention.

EXAMPLES

Example 1: Syntheses

Preparation of N-(1-ethyl-8-fluoro-4-methyl-2-oxo-3,4-dihydroquinolin-6-yl)-1-(p-tolyl)methanesulfonamide (HQ30)

1) 8-fluoro-4-methyl-3,4-dihydro-1H-quinolin-2-one

An autoclave was charged with 8-fluoro-4-methyl-quinolin-2-ol (1.77 g), 10% Pd/C (0.177 g) and ethanol (25 mL). The reaction mixture was hydrogenated at 80° C. under 50 bar of $H_2$ for 16 h. The reaction mixture was then carefully filtered through a pad of Celite® to give 8-fluoro-4-methyl-3,4-dihydro-1H-quinolin-2-one as a clourless solid (1.70 g, 96%); $^1$H NMR (400 MHz, CHLOROFORM-d) δ ppm 7.49-7.91 (br, 1H) 6.77-7.07 (m, 3H) 3.19 (sxt, 1H) 2.75 (dd, 1H) 2.46 (dd, 1H) 1.29 (d, 3H).

2) 1-ethyl-8-fluoro-4-methyl-3,4-dihydroquinolin-2-one

8-Fluoro-4-methyl-3,4-dihydro-1H-quinolin-2-one (1.70 g) was dissolved in DMF (19 mL) and potassium carbonate (2.65 g, equiv) was added followed by bromoethane (1.42 mL, equiv.). The suspension was heated to 50° C. overnight. Another equivalent of potassium carbonate and bromoethane were added and the solution was heated for another 3 h at 50° C. The reaction mixture was poured into ice/water and extracted twice with ethyl acetate. The combined organic layer were washed with brine and concentrated. The crude oil was purified by column chromatography to give 1-ethyl-8-fluoro-4-methyl-3,4-dihydroquinolin-2-one (1.50 g, 76%); 1H NMR (400 MHz, CHLOROFORM-d) δ ppm 1.15-1.34 (m, 6H) 2.43 (dd, 1H) 2.67 (dd, 1H) 2.93-3.16 (m, 1H) 3.88-4.23 (m, 2H) 6.89-7.12 (m, 3H).

3) 1-ethyl-8-fluoro-4-methyl-6-nitro-3,4-dihydroquinolin-2-one

Sodium nitrate (0.164 mg) was dissolved in trifluoroacetic acid (4 mL) and 1-ethyl-8-fluoro-4-methyl-3,4-dihydroquinolin-2-one (200 mg) was added. The solution was heated carefully at 50° C. for 1 h. The solution was poured into ice, neutralized with potassium carbonate and extracted two times with ethyl acetate. The combined organic layers were washed with saturated $NaHCO_3$, brine and concentrated. The resulting oil crystalized upon standing to give 1-ethyl-8-fluoro-4-methyl-6-nitro-3,4-dihydroquinolin-2-one (230 mg, 95%); 1H NMR (400 MHz, CHLOROFORM-d) δ ppm 1.24-1.30 (m, 3H) 1.34 (d, 3H) 2.50 (dd, 1H) 2.73 (dd, 1H) 3.04-3.26 (m, 1H) 3.95-4.22 (m, 2H) 7.88-8.01 (m, 2H).

4) 1-ethyl-8-fluoro-4-methyl-6-amino-3,4-dihydro-quinolin-2-one

1-Ethyl-8-fluoro-4-methyl-6-nitro-3,4-dihydroquinolin-2-one (1.73 g) was suspended in a mixture of ethanol/water (17 mL/8.5 mL) and ammonium chloride (3.67 g) was added followed by iron powder (1.15 g). The solution was heated to 100° C. for 45 min. The reaction mixture was cooled down, filtered through a pad of celite and the filtrate was washed with brine and concentrated. The resulting oil was purified by column chromatography to give 1-ethyl-8-fluoro-4-methyl-6-amino-3,4-dihydroquinolin-2-one as a yellow oil (1.50 g, 98%); 1H NMR (400 MHz, CHLORO- FORM-d) δ ppm 1.22 (m, 6H) 2.37 (dd, 1H) 2.61 (dd, 1H) 2.81-3.02 (m, 1H) 3.66 (br. s., 2H) 3.87-4.08 (m, 2H) 6.22-6.42 (m, 2H).

5) N-(1-ethyl-8-fluoro-4-methyl-2-oxo-3,4-dihydro-quinolin-6-yl)-1-(p-tolyl)methanesulfonamide (HQ30)

1-Ethyl-8-fluoro-4-methyl-6-amino-3,4-dihydroquinolin-2-one (111 mg) was dissolved in ethyl acetate (3 mL) and cooled to 0° C. Hunig's base (0.131 mL) was added followed by p-tolylmethanesulfonyl chloride (113 mg). The reaction mixture was stirred at 0° C. for 40 min and water was added. The reaction mixture was extracted two times with ethyl acetate. The combined organic layers were washed with saturated $NaHCO_3$, brine and concentrated. The resulting compound was purified by column chromatography to give N-(1-ethyl-8-fluoro-4-methyl-2-oxo-3,4-dihydroquinolin-6-yl)-1-(p-tolyl)methanesulfonamide which was further recrystallized from dichloromethane/diisopropyl ether (86 mg, 44%); 1H NMR (400 MHz, CHLOROFORM-d) δ ppm 1.18-1.29 (m, 6H) 2.35 (s, 3H) 2.41 (dd, J=15.22, 7.15 Hz, 1H) 2.65 (dd, J=15.22, 4.95 Hz, 1H) 2.83-3.05 (m, 1H) 3.90-4.12 (m, 2H) 4.32 (s, 2H) 6.50 (s, 1H) 6.68 (s, 1H) 6.83 (dd, J=13.94, 2.20 Hz, 1H) 7.12-7.23 (m, 4H).

Preparation of N-(8-cyano-1-ethyl-2-oxo-3,4-dihydroquinolin-6-yl)-1-(p-tolyl)methanesulfonamide (Compound HQ41)

1) 8-cyano-3,4-dihydro-1H-quinolin-2-one

8-Chloro-3,4-dihydro-1H-quinolin-2-one (0.500 g, 2.75 mmol) was dissolved in dioxane (2.5 mL) and water (2.5 mL). Potassium acetate (0.034 g, 0.344 mmol), tBuBrettPhos Pd G3 (0.235 g, 0.275 mmol), tButBrettPhos (0.133 g, 0.275 mmol) and potassium hexacyanoferrate(II) trihydrate (0.507 g, 1.37 mmol) in water (0.5 mL) were added. The reaction mixture was degassed with $N_2$, and heated to 100° C. and stirred for 90 min. Water was added and the reaction mixture was extracted with ethyl acetate (3×20 mL). The combined organic layers were washed with brin, dired amd concentrated. The crude mixture was purified by flash chromatography to give 8-cyano-3,4-dihydro-1H-quinolin-2-one (0.317 g, 67%); $^1$H NMR (CHLOROFORM-d) δ: 7.81 (br s, 1H), 7.45 (d, 1H), 7.39 (d, 1H), 7.05 (t, 1H), 2.99-3.06 (t, 2H), 2.66-2.72 (t, 2H).

2) 8-cyano-1-propyl-3,4-dihydro-quinolin-2-one

The compound was prepared using a similar procedure as 1-ethyl-8-fluoro-4-methyl-3,4-dihydroquinolin-2-one starting from 8-cyano-3,4-dihydro-1H-quinolin-2-one (0.310 g, 1.80 mmol) and propyl bromide (0.447 g, 3.60 mmol). The compound was obtained as a pale oil (0.350 g, 90%); $^1$H NMR (CHLOROFORM-d) δ: 7.55 (d, 1H), 7.40 (d, 1H), 7.09 (t, 1H), 4.28-4.35 (q, 2H), 2.84-2.93 (t, 2H), 2.60-2.68 (t, 2H), 1.69 (sxm, 2H), 0.90 (t, 3H).

3) 8-cyano-6-nitro-1-propyl-3,4-dihydro-quinolin-2-one

The compound was prepared using a similar procedure as 1-ethyl-8-fluoro-4-methyl-6-nitro-3,4-dihydroquinolin-2-one starting from 8-cyano-1-propyl-3,4-dihydro-quinolin-2-one (0.190 g, 0.89 mmol)(123 mg, 54%); $^1$H NMR (CHLOROFORM-d) δ: 8.44 (s, 1H), 8.23 (s, 1H), 4.33 (q, 3H), 3.03 (t, 2H), 2.71 (t, 2H), 1.61-1.79 (m, 3H), 0.92 (t, 3H)

4) 6-amino-2-oxo-1-propyl-3,4-dihydroquinoline-8-carbonitrile

The compound was prepared using a similar procedure as 1-ethyl-8-fluoro-4-methyl-6-amino-3,4-dihydroquinolin-2-one starting from 8-cyano-6-nitro-1-propyl-3,4-dihydro-quinolin-2-one (0.123 g, 0.47 mmol)(44 mg, 44%); $^1$H NMR (CHLOROFORM-d) δ: 6.79 (d, 1H), 6.72 (d, 1H), 4.22 (q, 2H), 2.85 (t, 2H), 2.55 (t, 2H), 0.86 (t, 3H).

5) N-(1-ethyl-8-fluoro-4-methyl-2-oxo-3,4-dihydro-quinolin-6-yl)-1-(p-tolyl)methanesulfonamide (HQ41)

The compound was prepared using a similar procedure as 1-ethyl-8-fluoro-4-methyl-6-amino-3,4-dihydroquinolin-2-one starting from 6-amino-2-oxo-1-propyl-3,4-dihydroquinoline-8-carbonitrile (0.044 g)(21 mg, 27%); $^1$H NMR (CHLOROFORM-d) δ: 7.14-7.23 (m, 4H), 7.04-7.11 (m, 3H), 4.35 (s, 2H), 4.22-4.28 (m, 2H), 2.79 (m, 2H), 2.57-2.62 (m, 2H), 2.35 (s, 2H), 1.67 (sxm, 2H), 1.43 (s, 3H), 0.90 (m, 3H).

Preparation of N-(1-ethyl-7-fluoro-4-methyl-2-oxo-3,4-dihydroquinolin-6-yl)-1-(p-tolyl)methanesulfonamide (Compound HQ47)

1) 6-bromo 7-fluoro-3,4-dihydro-1H-quinolin-2-one 7-fluoro-3,4-dihydroquinolin-2(1H)-one (1.00 g, 5.75 mmol) was dissolved in DMF (12 mL) and cooled to 0° C. N-Bromosuccinimide (1.14 g, 6.33 mmol) was added in small portions, reaction mixture was warmed up to rt and stirred for 4 h. The reaction mixture was poured into water and the white solid was filtered, washed with water, and dried. The crude solid was purified by flash chromatography to give 6-bromo-7-fluoro-3,4-dihydroquinolin-2(1H)-one (1.28 g, 92%); 1H NMR (CHLOROFORM-d) δ: 9.21 (br s, 1H), 7.29-7.37 (m, 1H), 6.67 (d, 1H), 2.95 (br m, 2H), 2.65 (m, 2H).

2) 6-bromo-7-fluoro-1-propyl-3,4-dihydroquinolin-2-one

6-Bromo-7-fluoro-3,4-dihydroquinolin-2(1H)-one (0.250 g, 1.024 mmol) was dissolved in DMF (5 mL) and potassium carbonate (0.212 g, 1.53 mmol) was added followed by 1-bromopropane (0.188 mL, 2.05 mmol). The reaction mixture was heated to 60° C. 1-Bromopropane (0.188 ml, 2.05 mmol) was added again and the reaction was stirred for another 90 min at 60° C. After cooling down to room temperature, the reaction mixture was poured on ice-cold water and it was extracted twice with ethyl acetate. The combined organic layers were washed twice with water and with brine, dried over $Na_2SO_4$ and the solvent was evaporated to give the crude product which was further purified by flash chromatography to give 6-bromo-7-fluoro-1-propyl-3,4-dihydroquinolin-2-one (0.242 g, 82%) as a colourless solid. $^1$H NMR (CHLOROFORM-d) δ: 7.31 (d, 1H), 6.77 (d, 1H), 3.78-3.88 (m, 2H), 2.85 (m, 2H), 2.59-2.68 (m, 2H), 1.65 (sxm, 2H), 0.96 (m, 3H).

3) N-(7-fluoro-2-oxo-1-propyl-3,4-dihydroquinolin-6-yl)-1-(p-tolyl)methanesulfonamide 6-Bromo-7-fluoro-1-propyl-3,4-dihydroquinolin-2-one (0.120 g, 0.414 mmol), p-tolylmethanesulfonamide (0.123 g, 0.630 mmol) and potassium carbonate (0.117 g, 0.838 mmol) were suspended in toluene (1.7 mL) and the solution was purged with argon. tBuBrettPhosPd G3 (Aldrich, 7.1 mg, 0.0084 mmol) was added and the reaction mixture was placed in a 90° C. preheated oil bath and stirred for 4 h. More tBuBrettPhosPdG3 (21 mg, 0.06 eq.) were added and the reaction mixture was heated for another 2 h. After cooling to room temperature, the reaction mixture was diluted with ethyl acetate and water/brine. The aqueous layer was extracted twice with ethyl acetate, the organic layers were combined, dried over $Na_2SO_4$ and the solvent was evaporated to give a brown gum which was purified by flash chromatography to give N-(7-fluoro-2-oxo-1-propyl-3,4-dihydroquinolin-6-yl)-1-(p-tolyl)methanesulfonamide (112 mg, 68%) as a white solid. $^1$H NMR (CHLOROFORM-d) δ: 7.15-7.25 (m, 5H), 6.75 (d, 1H), 6.29 (s, 1H), 4.33 (s, 2H), 3.79-3.88 (m, 2H), 2.78-2.85 (m, 2H), 2.60-2.66 (m, 2H), 2.35 (s, 3H), 1.66 (sxm, 2H), 0.98 (m, 3H).

Compounds HQ1-HQ57 (see Table 1) were prepared using a similar method starting from commercial 8-fluoro-3,4-dihydro-1H-quinolin-2-one, 8-chloro-3,4-dihydro-1H-quinolin-2-one, 8-bromo-3,4-dihydro-1H-quinolin-2-one, 7-fluoro-3,4-dihydro-TH-quinolin-2-one, 5-fluoro-3,4-dihydro-TH-quinolin-2-one and sulfonyl chlorides or sulfonyl amides.

TABLE 1

Synthesized Compounds

| Structure | Compound | RT | Mass | Method |
|---|---|---|---|---|
| 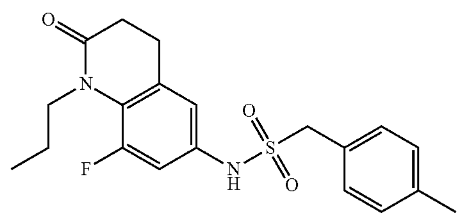 [SMILES: CCCN1C(=O)CCc2cc(NS(=O)(=O)Cc3ccc(C)cc3)cc(F)c21] | HQ1 | 0.97 | 391 | A |
| 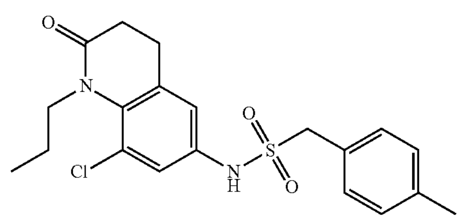 [SMILES: CCCN1C(=O)CCc2cc(NS(=O)(=O)Cc3ccc(C)cc3)cc(Cl)c21] | HQ2 | 0.99 | 407/409 | A |
| 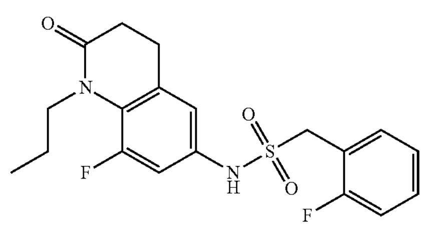 [SMILES: CCCN1C(=O)CCc2cc(NS(=O)(=O)Cc3ccccc3F)cc(F)c21] | HQ3 | 1.45 | 395.32 | B |
| 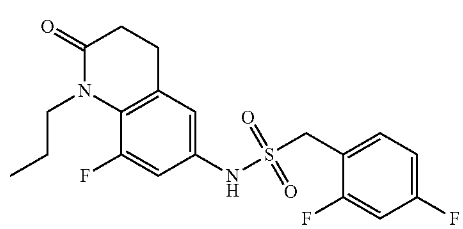 [SMILES: CCCN1C(=O)CCc2cc(NS(=O)(=O)Cc3ccc(F)cc3F)cc(F)c21] | HQ4 | 1.48 | 413.3 | B |
| 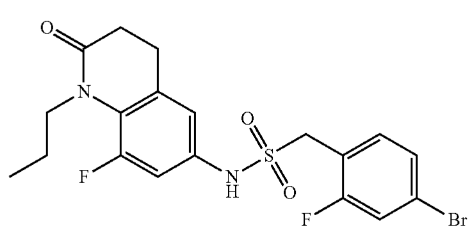 [SMILES: CCCN1C(=O)CCc2cc(NS(=O)(=O)Cc3ccc(Br)cc3F)cc(F)c21] | HQ5 | 1.6 | 473.28 | B |

TABLE 1-continued
Synthesized Compounds
| Structure | Compound | RT | Mass | Method |
|---|---|---|---|---|
| 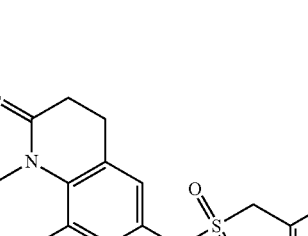 | HQ6 | 1.47 | 413.32 | B |
| 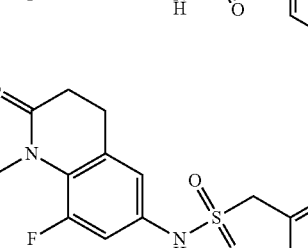 | HQ7 | 1.48 | 413.31 | B |
| 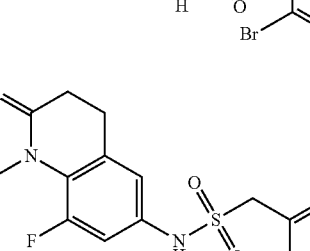 | HQ8 | 1.58 | 473.28 | B |
| 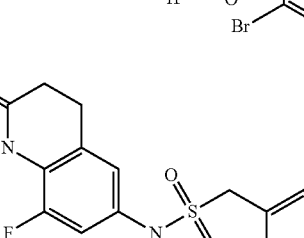 | HQ9 | 1.68 | 489.28 | B |
| 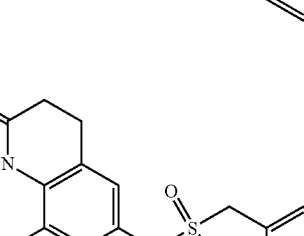 | HQ10 | 1.35 | 402.32 | B |
| 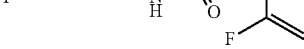 | HQ11 | 1.39 | 420.32 | B |

TABLE 1-continued

Synthesized Compounds

| Structure | Compound | RT | Mass | Method |
|---|---|---|---|---|
| 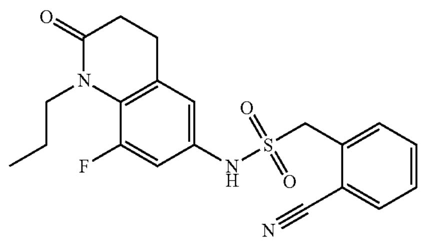 [SMILES: CCCN1C(=O)CCc2cc(NS(=O)(=O)Cc3ccccc3C#N)cc(F)c21] | HQ12 | 1.36 | 402.3 | B |
| 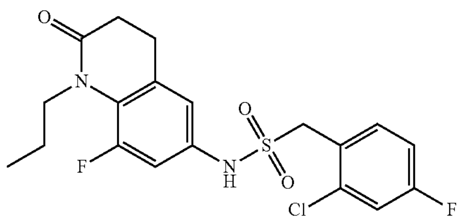 [SMILES: CCCN1C(=O)CCc2cc(NS(=O)(=O)Cc3ccc(F)cc3Cl)cc(F)c21] | HQ13 | 1.52 | 429.31 | B |
| 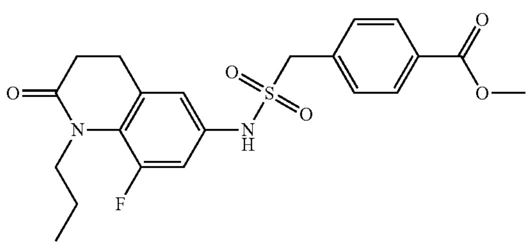 [SMILES: CCCN1C(=O)CCc2cc(NS(=O)(=O)Cc3ccc(C(=O)OC)cc3)cc(F)c21] | HQ14 | 1.43 | 435.36 | B |
| 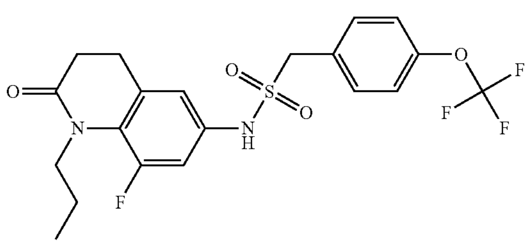 [SMILES: CCCN1C(=O)CCc2cc(NS(=O)(=O)Cc3ccc(OC(F)(F)F)cc3)cc(F)c21] | HQ15 | 1.66 | 461.36 | B |
| 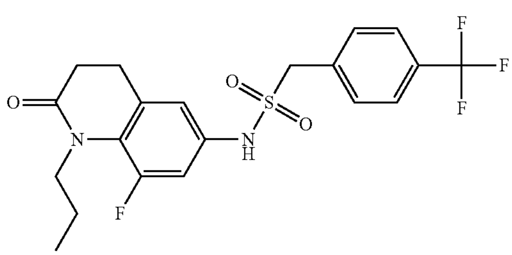 [SMILES: CCCN1C(=O)CCc2cc(NS(=O)(=O)Cc3ccc(C(F)(F)F)cc3)cc(F)c21] | HQ16 | 1.62 | 445.36 | B |
| 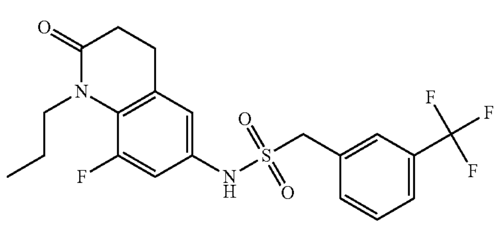 [SMILES: CCCN1C(=O)CCc2cc(NS(=O)(=O)Cc3cccc(C(F)(F)F)c3)cc(F)c21] | HQ17 | 1.6 | 445.36 | B |

TABLE 1-continued

Synthesized Compounds

| Structure | Compound | RT | Mass | Method |
|---|---|---|---|---|
| 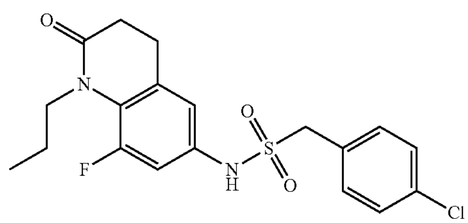 [SMILES: CCCN1C(=O)CCc2cc(NS(=O)(=O)Cc3ccc(Cl)cc3)cc(F)c21] | HQ18 | 1.56 | 411.3 | B |
| 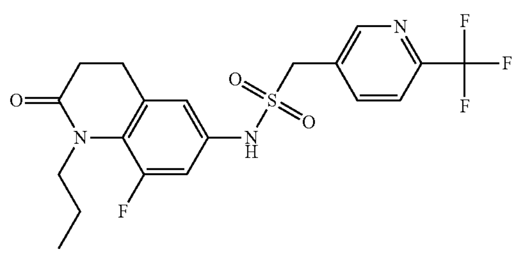 [SMILES: CCCN1C(=O)CCc2cc(NS(=O)(=O)Cc3ccc(C(F)(F)F)nc3)cc(F)c21] | HQ19 | 1.44 | 446.35 | B |
| 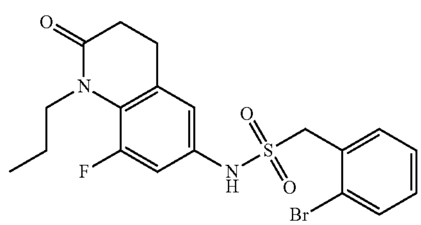 [SMILES: CCCN1C(=O)CCc2cc(NS(=O)(=O)Cc3ccccc3Br)cc(F)c21] | HQ20 | 1.54 | 455.26 | B |
| 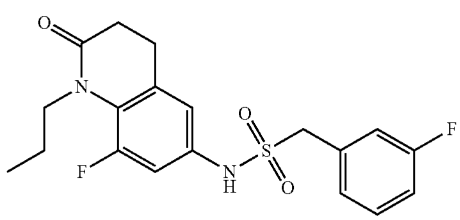 [SMILES: CCCN1C(=O)CCc2cc(NS(=O)(=O)Cc3cccc(F)c3)cc(F)c21] | HQ21 | 1.46 | 395.31 | B |
| 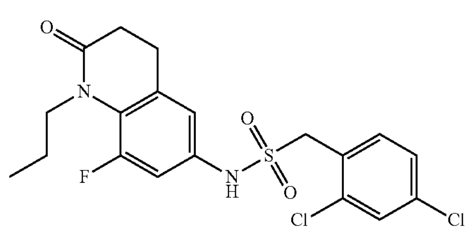 [SMILES: CCCN1C(=O)CCc2cc(NS(=O)(=O)Cc3ccc(Cl)cc3Cl)cc(F)c21] | HQ22 | 1.66 | 445.27 | B |
| 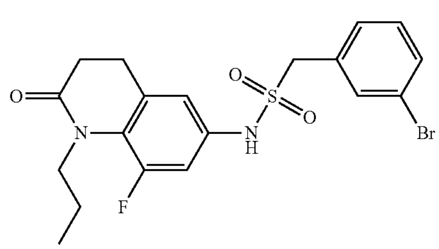 [SMILES: CCCN1C(=O)CCc2cc(NS(=O)(=O)Cc3cccc(Br)c3)cc(F)c21] | HQ23 | 1.57 | 455.28 | B |

TABLE 1-continued

Synthesized Compounds

| Structure | Compound | RT | Mass | Method |
|---|---|---|---|---|
| 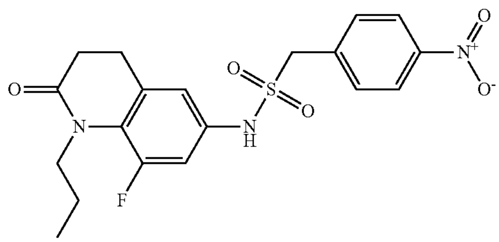 [SMILES: CCCN1C(=O)CCc2cc(NS(=O)(=O)Cc3ccc([N+](=O)[O-])cc3)cc(F)c21] | HQ24 | 1.43 | 422.34 | B |
| 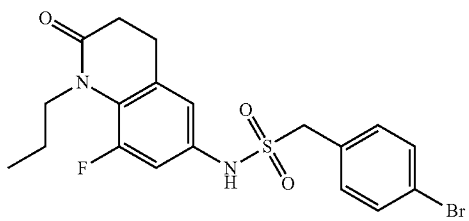 [SMILES: CCCN1C(=O)CCc2cc(NS(=O)(=O)Cc3ccc(Br)cc3)cc(F)c21] | HQ25 | 1.58 | 455.31 | B |
| 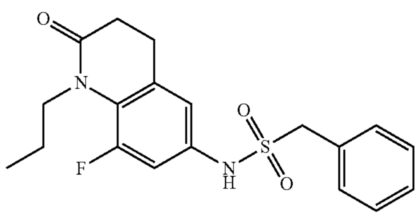 [SMILES: CCCN1C(=O)CCc2cc(NS(=O)(=O)Cc3ccccc3)cc(F)c21] | HQ26 | 1.44 | 377.31 | B |
| 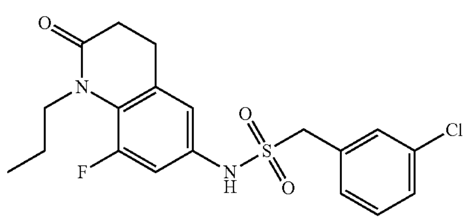 [SMILES: CCCN1C(=O)CCc2cc(NS(=O)(=O)Cc3cccc(Cl)c3)cc(F)c21] | HQ27 | 1.54 | 411.29 | B |
| 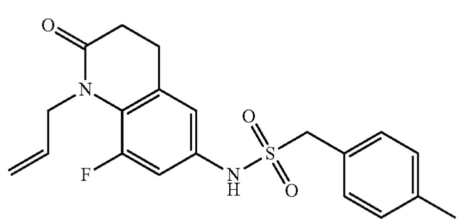 [SMILES: C=CCN1C(=O)CCc2cc(NS(=O)(=O)Cc3ccc(C)cc3)cc(F)c21] | HQ28 | 0.94 | 388 | A |
| 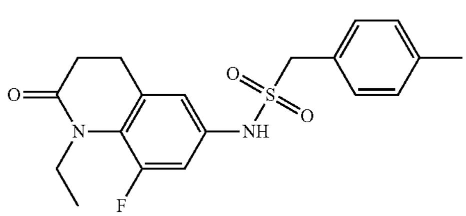 [SMILES: CCN1C(=O)CCc2cc(NS(=O)(=O)Cc3ccc(C)cc3)cc(F)c21] | HQ29 | 0.93 | 376 | A |
| 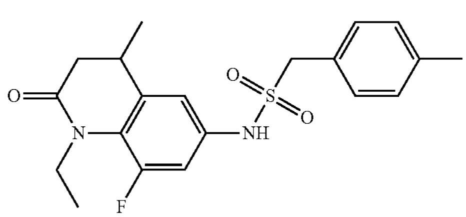 [SMILES: CCN1C(=O)CC(C)c2cc(NS(=O)(=O)Cc3ccc(C)cc3)cc(F)c21] | HQ30 | 0.96 | 391 | A |

TABLE 1-continued

| Synthesized Compounds | | | | |
|---|---|---|---|---|
| Structure | Compound | RT | Mass | Method |
| | HQ31 | 1.50 | 403 | B |
| | HQ32 | 1.59 | 405 | B |
| | HQ33 | 1.61 | 417 | B |
| | HQ34 | 1.69 | 419 | B |
| | HQ35 | 1.58 | 405 | B |
| | HQ36 | 1.40 | 433 | B |
| | HQ37 | 1.48 | 435 | B |

TABLE 1-continued

Synthesized Compounds

| Structure | Compound | RT | Mass | Method |
|---|---|---|---|---|
| 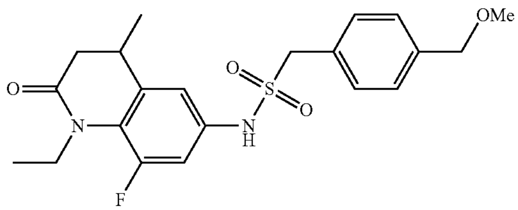 [SMILES: CCN1C(=O)CC(C)c2cc(NS(=O)(=O)Cc3ccc(COC)cc3)cc(F)c21] | HQ38 | 1.36 | 421 | B |
| 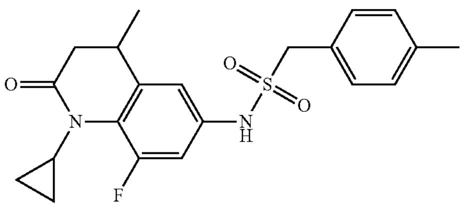 [SMILES: Cc1ccc(CS(=O)(=O)Nc2cc(F)c3c(c2)C(C)CC(=O)N3C2CC2)cc1] | HQ39 | 0.95 | 403 | A |
| 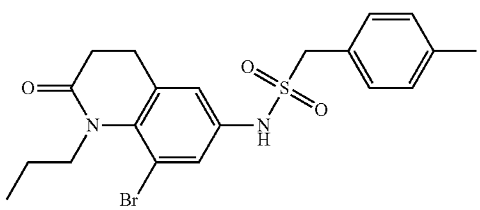 [SMILES: CCCN1C(=O)CCc2cc(NS(=O)(=O)Cc3ccc(C)cc3)cc(Br)c21] | HQ40 | 1.00 | 451/453 | A |
| 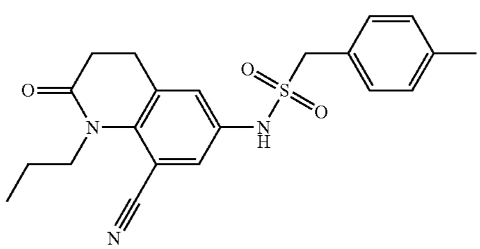 [SMILES: CCCN1C(=O)CCc2cc(NS(=O)(=O)Cc3ccc(C)cc3)cc(C#N)c21] | HQ41 | 0.95 | 398 | A |
| 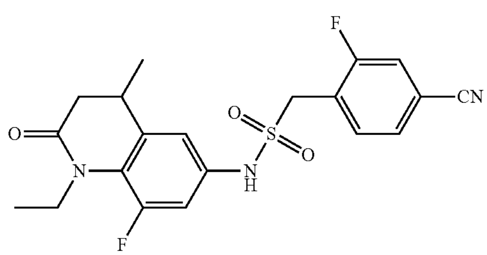 [SMILES: CCN1C(=O)CC(C)c2cc(NS(=O)(=O)Cc3ccc(C#N)cc3F)cc(F)c21] | HQ42 | 0.90 | 420 | A |
| 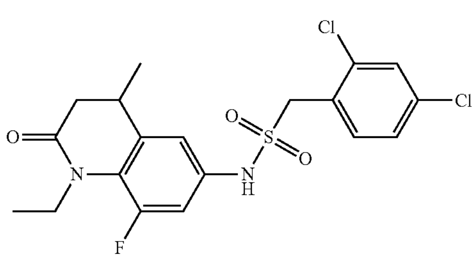 [SMILES: CCN1C(=O)CC(C)c2cc(NS(=O)(=O)Cc3ccc(Cl)cc3Cl)cc(F)c21] | HQ43 | 1.03 | 445/447 | A |

TABLE 1-continued

Synthesized Compounds

| Structure | Compound | RT | Mass | Method |
|---|---|---|---|---|
| 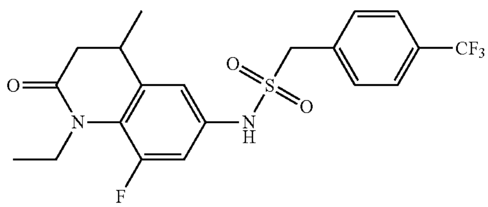 [SMILES: CCN1C(=O)CC(C)c2cc(NS(=O)(=O)Cc3ccc(C(F)(F)F)cc3)cc(F)c21] | HQ44 | 1.01 | 445 | A |
| 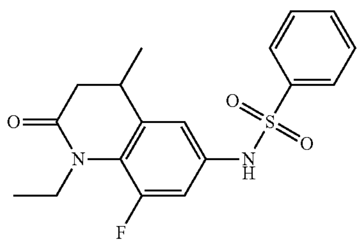 [SMILES: CCN1C(=O)CC(C)c2cc(NS(=O)(=O)c3ccccc3)cc(F)c21] | HQ45 | 0.91 | 363 | A |
| 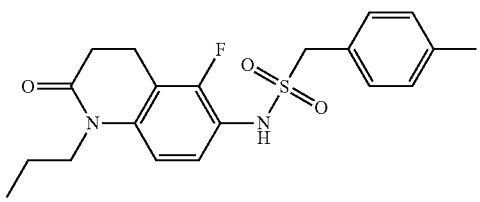 [SMILES: CCCN1C(=O)CCc2c1ccc(NS(=O)(=O)Cc1ccc(C)cc1)c2F] | HQ46 | 0.97 | 391 | A |
| 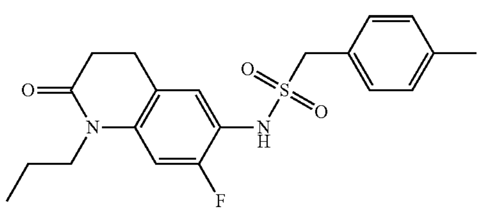 [SMILES: CCCN1C(=O)CCc2cc(NS(=O)(=O)Cc3ccc(C)cc3)c(F)cc21] | HQ47 | 0.97 | 391 | A |
| 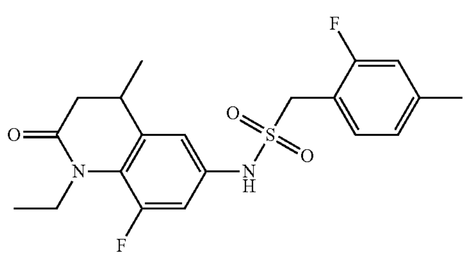 | HQ48 | 0.99 | 409 | A |
| 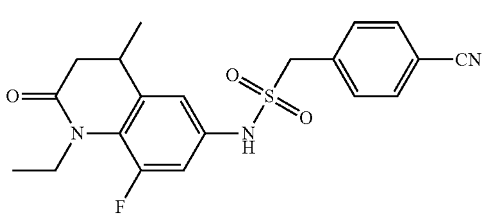 [SMILES: CCN1C(=O)CC(C)c2cc(NS(=O)(=O)Cc3ccc(C#N)cc3)cc(F)c21] | HQ49 | 0.88 | 402 | A |

TABLE 1-continued

Synthesized Compounds

| Structure | Compound | RT | Mass | Method |
|---|---|---|---|---|
| 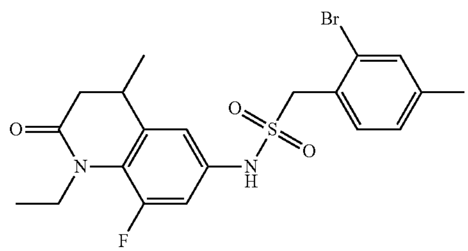 [SMILES: CCN1C(=O)CC(C)c2cc(NS(=O)(=O)Cc3ccc(C)cc3Br)cc(F)c21] | HQ50 | 1.04 | 469/471 | A |
| 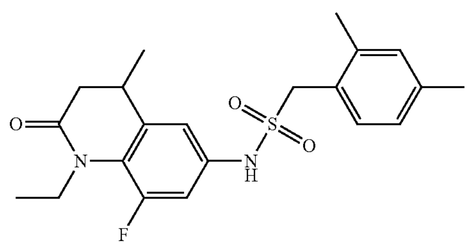 [SMILES: CCN1C(=O)CC(C)c2cc(NS(=O)(=O)Cc3ccc(C)cc3C)cc(F)c21] | HQ51 | 1.03 | 405 | A |
| 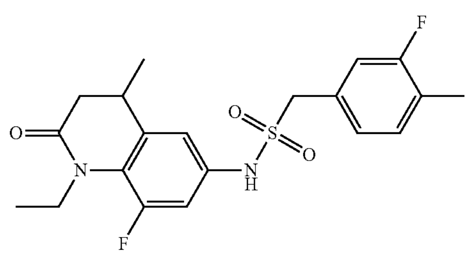 [SMILES: CCN1C(=O)CC(C)c2cc(NS(=O)(=O)Cc3ccc(C)c(F)c3)cc(F)c21] | HQ52 | 0.99 | 409 | A |
| 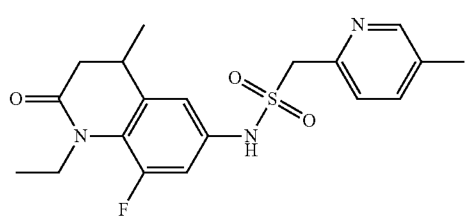 [SMILES: CCN1C(=O)CC(C)c2cc(NS(=O)(=O)Cc3ccc(C)cn3)cc(F)c21] | HQ53 | 0.84 | 392 | A |
| 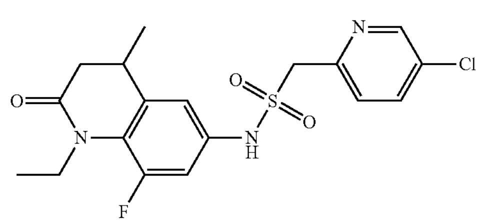 | HQ54 | 0.90 | 410/412 | A |
| 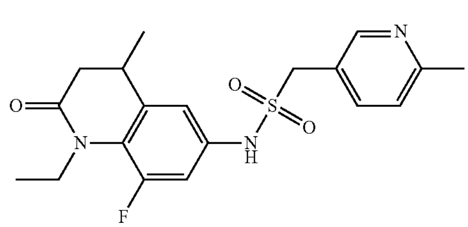 [SMILES: CCN1C(=O)CC(C)c2cc(NS(=O)(=O)Cc3ccc(C)nc3)cc(F)c21] | HQ55 | 0.73 | 392 | A |

TABLE 1-continued

Synthesized Compounds

| Structure | Compound | RT | Mass | Method |
|---|---|---|---|---|
| (structure) | HQ56 | 0.88 | 410/412 | A |
| (structure) | HQ57 | 0.99 | 417/419 | A |

Method—A:

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 μm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 0% B, 100% A; 1.2-1.5 min 100% B; Flow (ml/min) 0.85.

Method—B:

Spectra were recorded on a Mass Spectrometer from Waters SQD 2 equipped with an electrospray source (Polarity: positive ions, Capillary: 3.5 kV, Cone range: 30 V, Extractor: 3.00 V, Source Temperature: 150° C., Desolvation Temperature: 400° C., Cone Gas Flow: 60 L/Hr, Desolvation Gas Flow: 700 L/Hr, Mass range: 140 to 800 Da) and an Acquity UPLC from Waters: Binary pump, heated column compartment and diode-array detector. Solvent degasser, binary pump, heated column compartment and diode-array detector. Column: Waters UPLC HSS T3, 1.8 micron, 30×2.1 mm, Temp: 60° C., DAD Wavelength range (nm): 210 to 400, Solvent Gradient: A=water+5% MeOH+0.1% HCOOH, B=Acetonitrile+0.1% HCOOH; gradient: 0 min 100% A; 2.5 min 100% B; 2.8 min 100% B; 3.0 min 100% A; Flow (ml/min) 0.75.

Example 2: In-Vitro Activity

The protein HAB1, a type 2 protein phosphatase (PP2C), is inhibited by PYR/PYL proteins in dependence of abscisic acid or other agonists. The potency of an agonist correlates with the level of inhibition of the PP2C, and therefore the $IC_{50}$ (receptor-HAB1) can be used to compare the relative activity of different chemical analogues. Since inhibition of PP2C correlates to inhibition of seed-germination and increase in plant water-use efficiency, it serves as a powerful tool to quantify biological potential of a chemical acting as an analogue of abscisic acid.

HAB1 and PYL proteins were expressed and purified as described in Park et al. ((2009) Science 324(5930):1068-1071), with minor modifications. GST-HAB1 was produced by expression in BL21[DE3]pLysS host cells with an expression clone containing the HAB1 cDNA cloned into pGex-2T. Transformed E. coli cells were pre-cultured overnight, transferred to LB medium and cultured at 30° C. to culture A600 of ~0.5 OD units. The culture was then cooled on ice and $MnCl_2$ added to 4 mM and IPTG added to 0.3 mM. After 16 hours incubation at 15° C., cells were harvested and recombinant proteins were purified on glutathione agarose as described in Park et al. To obtain 6×His-PYL receptor fusion proteins, we used expression constructs previously described by Okamoto et al. 2013, (PNAS 110 (29): 12132-12137).

PP2C activity assays using recombinant receptors and PP2Cs were carried out as follows: purified proteins were pre-incubated in 160 μl assay buffer containing (100 mM Tris-HCl-pH7.9, 100 mM NaCl, 3 μg bovine serum albumin and 0.1% 2-mercaptoethanol), 1 mM $MnCl_2$ with carrier solvent (DMSO), quinabactin or quinabactin analogs (compounds of the present invention) for 30 minutes at room temperature. Reactions were started by adding 40 μL of a reaction solution containing 25 mM 4-nitrophenyl phosphate in assay buffer, after which absorbance measurements were immediately collected (405 nm) using a Wallac plate reader. Reactions contained 100 nM HAB1 PP2C and 200 nM receptor and 200 nM test compound. Inhibition is indicated by reduced PP2C activity, which is expressed as a percentage of the control PP2C activity values that were obtained from assays containing carrier solvent instead but no test compound. For $IC_{50}$ calculations, compounds at concentrations ranging from 1 μM to 4 nM were used in assays conducted in triplicate and the acquired dose response data was fitted to a log (inhibitor) versus response-(variable slope) model using non-linear regression to infer the $IC_{50}$s, using Graph Pad Prism 6.0.

TABLE 2

% Inhibition of PYR/PYL-HAB1 at 200 nM.

| Compound | PYR1 | PYL1 | PYL2 |
| --- | --- | --- | --- |
| Quinabactin | 22 | 23 | 44 |
| HQ1 | 14.7 | 11.8 | 28.0 |
| HQ2 | 37.9 | 20.3 | 38.9 |
| HQ3 | 65.7 | 46.7 | 78.3 |
| HQ4 | 61.5 | 46.1 | 69.3 |
| HQ5 | 42.9 | 18.2 | 51.8 |
| HQ6 | 57.9 | 35.1 | 57.4 |
| HQ7 | 53.9 | 31.0 | 67.4 |
| HQ8 | 107.1 | 87.4 | 92.0 |
| HQ9 | 104.7 | 86.9 | 92.2 |
| HQ10 | 39.8 | 44.3 | 77.2 |
| HQ11 | 28.8 | 27.9 | 73.5 |
| HQ12 | 106.3 | 82.4 | 94.5 |
| HQ13 | 110.0 | 88.2 | 94.1 |
| HQ14 | 62.6 | 78.9 | 91.8 |
| HQ15 | 54.8 | 47.6 | 70.1 |
| HQ16 | 52.0 | 38.5 | 53.9 |
| HQ17 | 104.0 | 88.1 | 88.2 |
| HQ18 | 35.0 | 34.2 | 46.7 |
| HQ19 | 82.7 | 73.4 | 82.3 |
| HQ20 | 97.4 | 84.7 | 94.1 |
| HQ21 | 62.4 | 48.2 | 63.7 |
| HQ22 | 91.5 | 70.6 | 86.3 |
| HQ23 | 90.8 | 85.7 | 87.8 |
| HQ24 | 69.0 | 53.2 | 76.5 |
| HQ25 | 33.8 | 20.8 | 42.8 |
| HQ26 | 63.6 | 51.4 | 74.8 |
| HQ27 | 90.0 | 79.8 | 88.0 |

TABLE 3

Inhibition of PYR1-HAB1 and PYL2-HAB1

| Compound | PYR1 IC50 (nM) | PYL2 IC50 (nM) |
| --- | --- | --- |
| Quinabactin | 104 | 262 |
| HQ30 | 39.6 | 11 |
| HQ29 | 17.2 | 83 |
| HQ28 | 62.3 | 401 |
| HQ1 | 37.5 | 42 |
| HQ2 | 47.7 | 74 |
| HQ11 | 61.2 | 317 |
| HQ18 | 63.3 | 102 |
| HQ25 | 75.0 | 77 |
| HQ31 | 164 | 52 |
| HQ32 | 408 | 40 |
| HQ33 | 204 | 61 |
| HQ34 | 462 | 26 |
| HQ35 | 37 | 12 |
| HQ36 | 126 | 32 |
| HQ37 | 227 | 33 |
| HQ38 | 103 | 26 |
| HQ39 | 1262 | 77 |
| HQ40 | 165 | 239 |
| HQ41 | 967 | 1453 |
| HQ42 | 589 | 247 |
| HQ43 | >10000 | 2006 |
| HQ44 | 2374 | 250 |
| HQ45 | >10000 | 7727 |
| HQ46 | 694 | 1461 |
| HQ47 | 172 | 182 |
| HQ48 | 56 | 23 |
| HQ49 | 405 | 112 |
| HQ50 | >10000 | 4466 |
| HQ51 | >10000 | 930 |
| HQ52 | 444 | 46 |
| HQ53 | 153 | 160 |
| HQ54 | 512 | 234 |
| HQ55 | >10000 | 1599 |
| HQ56 | 1253 | 486 |
| HQ57 | 953 | 94 |

Example 3: In-Vivo Activity

Plant Water Use in Soybean

Compounds were tested for their effect on reducing plant water use as follows. Each compound was dissolved in a blank emulsifiable concentrate (EC) formulation that was then diluted to the desired concentration with water containing additional surfactant (EXTRAVON 1 g/20 L). The compounds were applied by foliar spray to 12 day old soybean plants (variety S20-G7) grown in controlled environment plant growth chambers. Plant water use during the day was assessed by repeated weighing of the pots in which the plants were grown before and after application of the compounds at the indicated times (expressed in days after application (DAA)). The water use data before application was used to correct any differences in water use arising due to non-treatment effects (e.g. due to differences in plant size). The untransformed water use values were subjected to an analysis of covariance, fitting the effect of treatment and using the baseline water use 1 day before application as a covariate.

The results are expressed compared to negative control treatment (diluted EC formulation without active ingredient but with EXTRAVON 1 g/20 L).

Application of the chemicals (0 DAA) takes place approximately between 08:00 and 09:30 a.m. WU is measured within day time (chamber light is on 06:00 to 20:00) at these timepoints: 0 DAA a.m. (10:30-12:50), 0 DAA p.m. (14:00-19:50), 1 DAA a.m. (7:30-12:50), 1 DAA p.m. (14:00-19:50), 2 DAA a.m. (07:30-12:50) and 2 DAA p.m. (14:00-19:50). The culmulative total WU 0-2 DAA is calculated by summing the WU data mentioned above.

The percent of increase or decrease of water use (WU) during day time compared to a negative control treatment (blank formulation) are shown. 0=identical to negative control; −8.5=8.5% decrease in water use compared to negative control treatment. Average WU values of 6 pots (each with three plants) per treatment are shown.

FIG. 1 is a table showing water use data for soybean plants after administration of the indicated compounds at 500 μM.

FIG. 2 is a table showing water use data for soybean plants after administration of compound HQ1 or quinabactin at various concentrations.

Plant Water Use in Corn

Compounds were tested for their effect on reducing plant water use as follows. The compounds were applied by foliar spray to 12 day old corn plants (variety NK OCTET) grown in controlled environment plant growth chambers. All compounds were applied using an emulsifiable concentrate (EC) formulation that was diluted to the desired concentrations with water containing 0.4% of the adjuvant rape seed methyl ester. Plant water use during the day was assessed by repeated weighing of the pots in which the plants were grown before and after application of the compounds at the indicated times (expressed in days after application (DAA)). The water use data before application was used to correct any differences in water use arising due to non-treatment effects (e.g. due to differences in plant size). The untransformed water use values were subjected to an analysis of covariance, fitting the effect of treatment and using the baseline water use 1 day before application as a covariate.

Application of the chemicals (0 DAA) takes place approximately between 08:00 and 09:30 a.m. WU is measured within day time (chamber light is on 06:00 to 20:00) at these timepoints: 0 DAA a.m. (10:30-12:50), 0 DAA p.m. (14:00-19:50), 1 DAA a.m. (07:30-12:50), 1 DAA p.m. (14:00-19:50), 2 DAA a.m. (07:30-12:50) and 2 DAA p.m. (14:00-19:50). The culmulative total WU (0-2.5 DAA) is calculated by summing the WU data mentioned above.

The percent of increase or decrease of water use (WU) during day time compared to a negative control treatment (blank formulation) are shown. 0=identical to negative control; −8.5=8.5% decrease in water use compared to negative control treatment. Average WU values of 6 pots (each with three plants) per treatment are shown.

FIG. 3 is a table showing water use data for corn plants after administration of the indicated compounds at 500 μM.

FIG. 4 is a table showing water use data for corn plants after administration of the indicated compounds at 500 μM for one day after application. Application of the chemicals (0 DAA) takes place approximately between 08:00 and 09:30 a.m. WU is measured within day time (chamber light is on 06:00 to 20:00) at these timepoints: 0 DAA a.m. (10:30-12:50), 0 DAA p.m. (14:00-19:50).

It is understood that the examples and embodiments described herein are for illustrative purposes only and that various modifications or changes in light thereof will be suggested to persons skilled in the art and are included within the spirit and purview of this application and are considered within the scope of the appended claims. All publications, patents, and patent applications cited herein are hereby incorporated by reference in their entirety for all purposes.

What is claimed is:

1. A compound selected from:

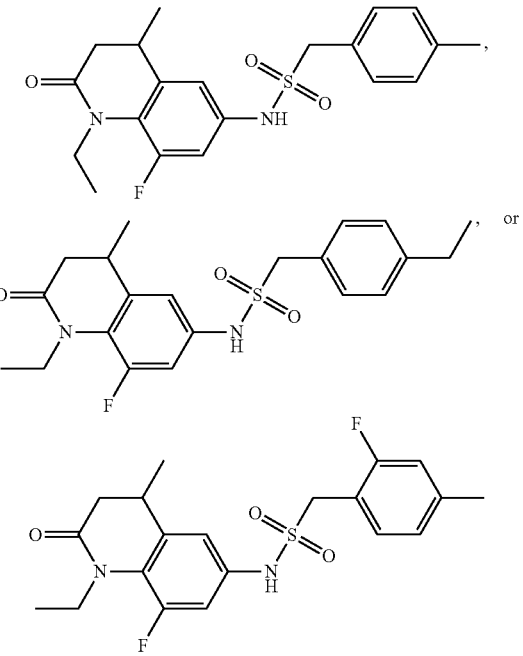

or salts thereof.

* * * * *